US012766188B2

(12) United States Patent
Basile

(10) Patent No.: US 12,766,188 B2
(45) Date of Patent: Oct. 20, 2026

(54) USES OF IL-12 AS A REPLACEMENT IMMUNOTHERAPEUTIC

(71) Applicant: Karyopharm Therapeutics Inc., Newton, MA (US)

(72) Inventor: Lena A. Basile, Pasadena, CA (US)

(73) Assignee: Karyopharm Therapeutics Inc., Newton, MA (US)

( * ) Notice: Subject to any disclaimer, the term of this patent is extended or adjusted under 35 U.S.C. 154(b) by 1698 days.

(21) Appl. No.: 16/318,670

(22) PCT Filed: Jul. 18, 2017

(86) PCT No.: PCT/US2017/042600
§ 371 (c)(1),
(2) Date: Jan. 17, 2019

(87) PCT Pub. No.: WO2018/017571
PCT Pub. Date: Jan. 25, 2018

(65) Prior Publication Data

US 2024/0181010 A1 Jun. 6, 2024

Related U.S. Application Data

(60) Provisional application No. 62/363,648, filed on Jul. 18, 2016.

(51) Int. Cl.

| | |
|---|---|
| ***A61K 38/20*** | (2006.01) |
| ***A61K 9/00*** | (2006.01) |
| ***A61K 9/08*** | (2006.01) |
| ***A61K 47/02*** | (2006.01) |
| ***A61K 47/10*** | (2017.01) |
| ***A61P 7/06*** | (2006.01) |

(52) U.S. Cl.
CPC .......... *A61K 38/208* (2013.01); *A61K 9/0019* (2013.01); *A61K 9/08* (2013.01); *A61K 47/02* (2013.01); *A61K 47/10* (2013.01); *A61P 7/06* (2018.01)

(58) Field of Classification Search
CPC .................................................... A61K 38/208
See application file for complete search history.

(56) References Cited

U.S. PATENT DOCUMENTS

2014/0369958 A1* 12/2014 Basile .................... A61P 13/12
424/85.2
2016/0120949 A1 5/2016 Basile

FOREIGN PATENT DOCUMENTS

WO WO-9625171 A1 * 8/1996 .......... A61K 38/208
WO WO-2012174056 A1 * 12/2012 .......... A61K 38/208
WO WO-2013016634 A1 * 1/2013 .......... A61K 38/208

OTHER PUBLICATIONS

Neumedicines Inc. NM-IL-12 in Cutaneous T-Cell Lymphoma (CTCL) Undergoing Total Skin Electron Beam Therapy (TSEBT). Available from: https://clinicaltrials.gov/study/NCT02542124?intr=nm-il-12&rank=3&tab=history&a=1. NLM identifier. NCT 02542124. First posted Sep. 3, 2015. (Year: 2015).*
Yoshimatsu et al. IL-12 inhibits TNF-α induced osteoclastogenesis via a T cell-independent mechanism in vivo. Bone 45 (2009) 1010-1016) (Year: 2009).*
Carrero et al. Cytokine dysregulation in chronic kidney disease: How can we treat it? Blood Purification 2008; 26:291-299 (Year: 2008).*
Wang et al. Analysis of Aqueous Humor Cytokines in Exudative Age-related Macular Degeneration and Diabetic Macular Edema. Journal of the Korean Ophthalmological Society 2023;64(6):482-489 (Year: 2023).*
PCT International Search Report and Written Opinion, PCT Application No. PCT/US17/42600, Sep. 26, 2017.
Basile et al., "HemaMax (TM), a Recombinant Human Interleukin-12, Is a Potent Mitigator of Acute Radiation Injury in Mice and Non-Human Primates," PLOS One 7(2): e30434 (2012).
Gluzman-Poltorak et al., "Randomized comparison of single dose of recombinant human IL-12 versus placebo for restoration of hematopoiesis and improved survival in rhesus monkeys exposed to lethal radiation," Journal of Hematology and Oncology 7(1) (2014).
International Search Report and Written Opinion for International Application No. PCT/US17/42600 dated Sep. 26, 2017.
Arjamaa et al., "Regulatory role of HIF-1α in the pathogenesis of age-related macular degeneration (AMD)", Ageing Research Reviews, vol. 8, Issue 4, pp. 349-358, Oct. 2009.
Carrero et al., "Cytokine dysregulation in chronic kidney disease: How can we treat it?" Blood Purification, 26(3), 291-299 (2008).
Wang et al., "Analysis of Aqueous Humor Cytokines in Exudative Age-related Macular Degeneration and Diabetic Macular Edema." Journal of the Korean Ophthalmological Society 64(6), 482-489 (2023).
Zhou et al., "Interleukin-12 inhibits pathological neovascularization in mouse model of oxygen-induced retinopathy" Scientific Reports, vol. 6: 28140.

* cited by examiner

*Primary Examiner* — Vanessa L. Ford
*Assistant Examiner* — Sandra Carter
(74) *Attorney, Agent, or Firm* — FOLEY HOAG LLP

(57) ABSTRACT

Aspects and embodiments of the present disclosure provide therapeutic methods comprising interleukin 12 (IL-12) as a replacement immunotherapeutic. The method comprises administering a physiological dose of exogenous IL-12 to a subject.

17 Claims, 35 Drawing Sheets

NM-IL-12: A Stem Cell, Hematopoietic and Immune Cell Factor

*IL-12Rβ2 expression in medullary, but not cortical, tubules comprising the nephron, in Humans and Rhesus monkeys*

*Mag: x400*

*Hematological changes with 12μg NM-IL-12 (48 subjects) or Placebo (12 subjects) in healthy human volunteers*

A

B

A B C D

USES OF IL-12 AS A REPLACEMENT IMMUNOTHERAPEUTIC

CROSS-REFERENCE TO RELATED APPLICATIONS

This application is the U.S. National Phase of International Application No. PCT/US17/42600, filed on Jul. 18, 2017, which claims the priority benefit of U.S. provisional patent application No. 62/363,648, filed on Jul. 18, 2016, the entire contents of which are incorporated herein by reference.

FIELD

The present disclosure relates generally to methods and compositions utilizing IL-12 in replacement immunotherapy.

BACKGROUND

The following includes information that may be useful in understanding various aspects and embodiments of the present disclosure. It is not an admission that any of the information provided herein is prior art, or relevant, to the presently described or claimed inventions, or that any publication or document that is specifically or implicitly referenced is prior art.

Interleukin-12 (IL-12) is a heterodimeric cytokine, comprising both p40 and p35 subunits, that is well-known for its role in immunity. In numerous reports spanning about two decades, IL-12 has been shown to have an essential role in the interaction between the innate and adaptive arms of immunity by regulating inflammatory responses, innate resistance to infection, and adaptive immunity. Endogenous IL-12 is required for resistance to many pathogens and to transplantable and chemically induced tumors. The hallmark effect of IL-12 in immunity is its ability to stimulate the production of interferon-gamma (IFN-gamma) from natural killer (NK) cells, macrophages and T cells. Further, several in vitro studies in the early to mid-nineties reported that IL-12 is capable of stimulating hematopoiesis synergistically with other cytokines. The hematopoiesis-promoting activity of IL-12 appears to be due to a direct action on bone marrow stem cells as these studies used highly purified progenitors or even single cells. The role of IFN-gamma in the hematopoietic activity of IL-12 is not clear as several studies have linked both the promotion and suppression of hematopoiesis to IFN-gamma.

IL-12 is shown to have a radioprotective function when used before or shortly after exposure to total body radiation. IL-12 protects bone marrow from and sensitizes intestinal tract to ionizing radiation. IL-12 facilitates both the recovery of endogenous hematopoiesis and the engraftment of stem cells after ionizing radiation.

IL-12 is a well-characterized cytokine. In 1989, IL-12 was independently identified as natural killer-stimulating factor (NKSF) by Genetics Institute, Inc. and The Wistar Institute of Anatomy and Biology. In 1990, IL-12 was independently identified as a cytotoxic lymphocyte maturation factor (CLMF) by Hoffmann-La Roche, Inc. In 1991, IL-12 cDNA was cloned and named Interleukin-12 by Genetics Institute, Inc. In 1993, IL-12's central role in regulating and bridging innate and adaptive immunity was discovered. In 1995, IL-12's anti-angiogenic properties were discovered. In 1996, the IL-12 receptor was characterized by Hoffmann-La Roche, Inc. From 1993-2002, the antitumor and antimetastatic activities of IL-12 were extensively shown in murine models including melanomas, mammary carcinomas, colon carcinoma, renal carcinoma, and sarcoma. From 1997-2004, IL-12 mainly monotherapy was investigated in cancer patients. With exception to CTCL, AIDS-related Kaposi sarcoma, NHL, and melanoma, efficacy was minimal as a single agent. Reasons for limited clinical efficacy in cancer patients was due to the high and repeat dose regimens utilized, leading to tachyphylaxis (desensitization).

From 2003-2007, Neumedicines Inc. discovered that a single, low dose of IL-12 facilitates recovery of endogenous hematopoiesis after lethal ionizing radiation in mice. From 2005-2008, Neumedicines Inc. demonstrated both pro-hematopoiesis and antitumor activity (the hematopoietic immunotherapeutic effect) in myelosuppressed, tumor-bearing, murine model systems. From 2008-present, a Neumedicines-BARDA collaboration was initiated to develop IL-12 as a radiation medical countermeasure. From 2009-2014, Neumedicines Inc. demonstrated efficacy (hematopoietic effect) of IL-12 as a radiation medical countermeasure in monkeys, and demonstrated safety in healthy volunteers.

There is a need in the art for methods of treating various disease and wounds with an underlying immunosuppression, which are related in that they result in suppression of expression of endogenous IL-12.

SUMMARY OF THE INVENTION

The present disclosure provides methods of administering IL-12 as a replacement immunotherapeutic comprising (a) identifying a subject in need, wherein the subject is suffering from a disease or wound resulting in suppression of endogenous IL-12 expression; and (b) administering one or more physiological doses of exogenous IL-12 to the subject. The suppression of endogenous IL-12 expression can result in suppression of suppress key immune cells, including antigen presenting cells and dendritic cells.

In one aspect of the invention, prior to administration of one or more physiological doses of exogenous IL-12, a patient population to be treated has IL-12 expression levels of less than about 5 pg/ml or less than about 1 pg/ml. Generally patients to be treated will have less than 1 pg/ml of expression of IL-12 levels or will have expression levels below the lower limit of detection (LLOD), In one embodiment of the invention, administration of a physiological dose of exogenous IL-12 restores endogenous IL-12 pleiotropic immune and hematopoietic effects, including pleiotropic reparative, anti-infective and anti-tumor responses correlated with endogenous IL-12 expression. Further, administration of a physiological dose of exogenous IL-12 can result in improving outcomes for subjects with chronic disease and wounds.

In another embodiment of the invention, the exogenous physiological dose of IL-12 yields a range of NM-IL-12 in peripheral blood that is greater than about 5 picogram per ml and less than about 200 picograms per ml, as measured by a standard ELISA for IL-12 p70. The measureable levels of IL-12 in the peripheral blood of a subject can also show an concomitant increase in IFN-gamma in peripheral blood, and moreover, the concomitant levels of IFN-gamma following dosing can be in a range of about 20 pg/ml up to about 1000 pg/ml.

Further, the exogenous physiological dose of IL-12 can be greater than about 1 μg and less than about 20 μg, greater than about 8 μg and up to about 15 μg, or greater than about 10 μg and up to about 12 μg.

In yet another embodiment, during a course of treatment for a disease or wound, the subject can be given two physiological dose levels of IL-12: a treatment dose and a maintenance dose. The two types of doses can be the same or different. For example, the treatment dose of IL-12 can be greater than about 1 μg and less than about 20 μg; and/or the maintenance dose of IL-12 can be greater than about 1 μg and less than about 10 μg. Further, the treatment doses of IL-12 can be given about every 2 weeks, about every 3 weeks, or about every 4 weeks; and/or the maintenance doses of IL-12 can be given about every 1 month, about every 2 months, or about every 3 months.

The one or more physiological doses of IL-12 can be administered by any pharmaceutically acceptable means, including but not limited to topically, subcutaneously, intravenously, intraperitoneally, intramuscularly, epidurally, or parenterally.

The NM-IL-12 can be a recombinant human IL-12, e.g., rHuIL-12.

In one embodiment of the invention, the subject has chronic kidney disease and the administration of exogenous IL-12 results in repair and regeneration of the kidney, thereby slowing progression of CKD. The slowing of progression of CKD can be demonstrated by, for example, one or more in the subject of the following: a decrease in creatinine, a decrease in blood urea nitrogen (BUN), a decrease in albuminuria, or an increase in glomerular filtration rate (GFR). For example, administration of exogenous NM-IL-12 can slow the progression of CKD, as compared to the progression observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Administration of exogenous IL-12 can be used in combination with a conventional treatment for CKD.

In another embodiment of the invention, the subject has a wound and administration of exogenous IL-12 results in facilitating migration of cells into tissue to aid in wound healing and tissue repair and therefore producing accelerated healing of the wound. The subject can be anyone with a wound, including but not limited to an elderly subject, diabetic subject, or subject with a surgical wound. In other embodiments, the subject is elderly and has a pressure ulcer, or the subject is diabetic and has a foot ulcer. Administration of exogenous NM-IL-12 can result in accelerating wound healing, as compared to the rate of healing observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Administration of exogenous IL-12 can be used in combination with a conventional treatment for a wound.

In one embodiment, the subject has age-related macular degeneration (AMD) and administration of exogenous IL-12 results in slowing or reversing AMD progression. For example, progression of AMD can be slowed or reversed by IL-12's effects of (i) reducing neovascularization because IL-12 has broad anti-angiogenic effects against multiple angiogenic factors; and/or (ii) restoring immune balance by replenishment of senescent macrophages. Administration of exogenous IL-12 can be used in combination with a conventional treatment for AMD. In one embodiment, administration of exogenous IL-12 results in slowing or reversing AMD progression, as compared to that observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In another embodiment, IL-12 can be administered (i) via any route; (ii) via any route other than intraocular, (iii) via subcutaneous injection, or (iv) via intraocular injection.

In another embodiment, the subject suffers from osteoporosis and administration of exogenous IL-12 results in triggering hematopoietic stem cells to regenerate and mobilize cells in the bone marrow. Administration of exogenous IL-12 can result in reducing bone loss and/or decreasing osteoclast formation. For example, administration of exogenous IL-12 can result in reducing bone loss and/or reducing osteoclast formation, as compared to that observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. Administration of exogenous IL-12 can be used in combination with a conventional treatment for osteoporosis.

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction. Additional embodiments may be disclosed in the Detailed Description below.

BRIEF DESCRIPTION OF THE FIGURES

FIGS. 12A-F show hematological changes with 12 μg NM-IL-12 (48 subjects) or placebo (12 subjects) in healthy volunteers, with FIG. 12A=reticulocytes, FIG. 12B=platelets, FIG. 12C=CD34+ cells, FIG. 12D=lymphocytes, FIG. 12E=neutrophils, and FIG. 12F=NK cells.

FIG. 18A shows a picture of a wound following topical application of vehicle, while FIG. 18B, showing remarkable healing of the wound, depicts the results obtained with SC rMuIL-12 (20 ng, generated from the data of FIG. 17).

FIGS. 22A-F depict photos which represent corneas of either vehicle-treated (control) C57 BL/6 mice (FIG. 22A), SCID mice (FIG. 22B), and beige mice (FIG. 22C) or 12-treated C57BL/6 mice (FIG. 22D), SCID mice (FIG. 22E), and beige mice (FIG. 22F), 5 days after implantation of the basic fibroblast growth factor pellet (P). The figure shows that rMuIL-12 is an inhibitor of angiogenesis.

FIG. 24B=0.1 ng IL-12; FIG. 24C=0.1 ng IL-12; and FIG. 24D=1 ng IL-12).

FIG. 31 shows TRAP Counts—Rib, e.g., TRAP fraction of total rib area for two treatment groups (0 ng/kg and 250 IL-12 ng/kg) in non-human primates. SC administration of NM-IL-12 resulted in significantly decreasing osteoclast formation measured in rib. Statistical analysis by Students' t test, *p≤0.05 compared to vehicle.

As shown in FIG. 35A, all pre-dose IL-12 levels for 110 subject were Below the Limit of Quantitation (BLQ) (LLOQ=0.367 pg/ml). As shown in FIG. 35B, almost all IFN-gamma levels were quantifiable above the LLOQ (LLOQ=1.08 pg/ml), most in low pg/ml range. Five high end outliers showed baseline levels of IFN-gamma>23 pg/ml, including subject 1033 and 1055.

DETAILED DESCRIPTION

I. NM-IL-12: A Replacement Immunotherapeutic

Figure 6:
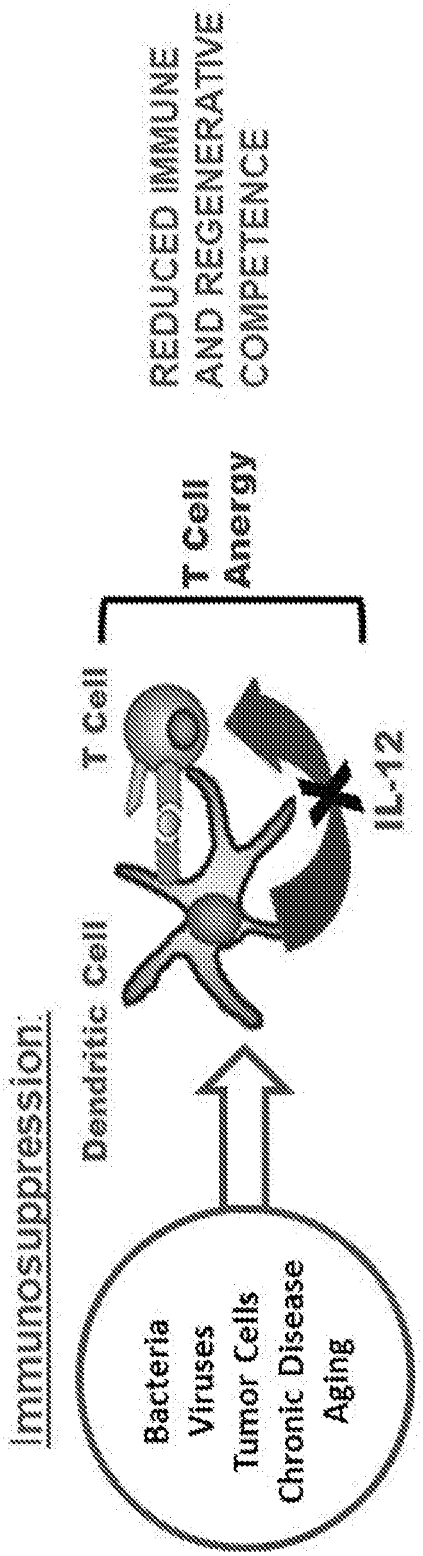
FIG. 6: Graphically depicts how chronic disease or aging suppresses key immune cells, i.e., antigen presenting/dendritic cells, inhibits IL-12 production thereby reducing immune competence.
Figure 7:
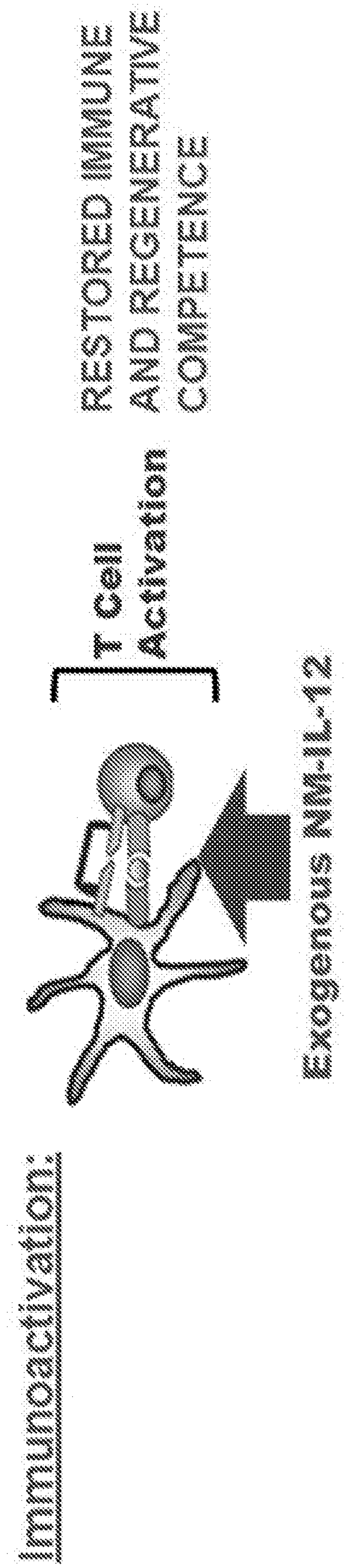
FIG. 7: Graphically shows the solution to the problem presented in FIG. 6, which is the use of IL-12, as exogenous NM-IL-12 reignites pleiotropic reparative, anti-infective and anti-tumor responses by restoring key immune competence and thereby improving outcomes for patients with chronic disease, cancer, infections and aging.
Figure 8:
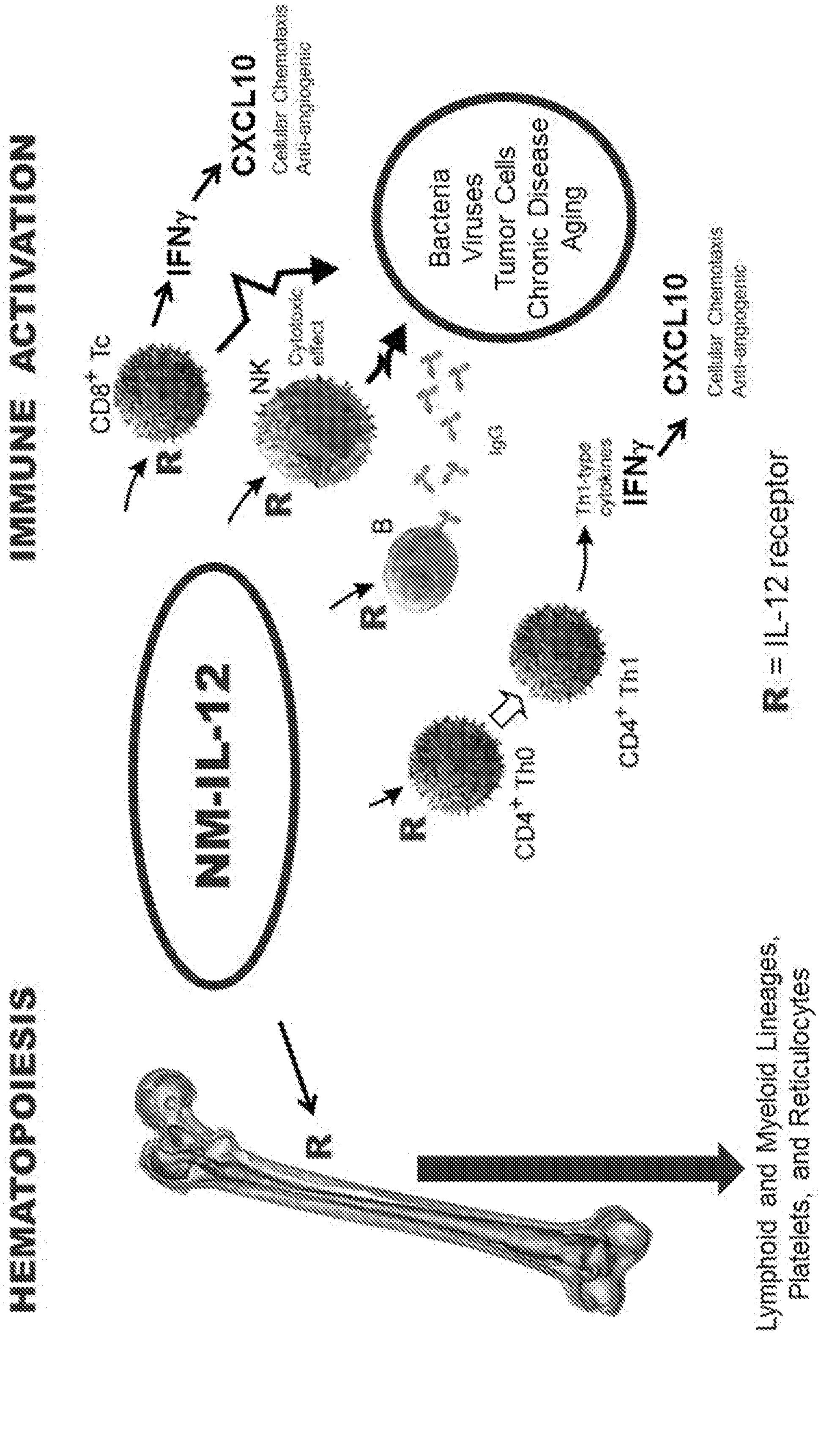
FIG. 8: Visually depicts how NM-IL-12 as a replacement immunotherapeutic restores endogenous IL-12 pleiotropic immune and hematopoietic effects (adapted from Lasek et al., *Cancer Immunol. Immunother.,* 63:419 (2014) via interaction with the unique IL-12 receptor found on all key mature immune effector cells and on immature progenitor and stem cells of the bone marrow.

The problem present prior to the this invention was the failure to recognize that seemingly varied conditions correlated with disease such as chronic disease, injuries or wounds, aging, infectious disease and cancer were related in that the conditions resulted in suppression of IL-12 expression, which thereby resulted in myriad undesirable effects. It was surprisingly discovered that the undesirable effects associated with a lack of production of endogenous IL-12 can be addressed by administering a physiological dose of IL-12. Specifically, disease such as chronic disease, injuries or wounds, and aging suppress key immune cells, i.e., antigen presenting/dendritic cells, and inhibit IL-12 production. FIG. 6. The solution to this problem is the administration of a physiological dose of exogenous IL-12, as a physiological dose of exogenous NM-IL-12 reignites pleiotropic reparative, anti-infective and anti-tumor responses thus restoring key immune effects and thereby improving outcomes for patients with disease and wounds. FIG. 7. See also FIG. 8, which visually depicts how NM-IL-12 as a replacement immunotherapeutic restores endogenous IL-12 pleiotropic immune and hematopoietic effects. In sum, NM-IL-12 is a replacement immunotherapeutic that gives back what they body was able to deliver when it was healthy. Many disease states, injuries, and aging cause the cells that produce endogenous IL-12 to become dysfunctional and are no longer able to produce IL-12. The present invention relates to the discovery of IL-12 as a key factor that can serve as a replacement immunotherapeutic in many varied disease states.

In one aspect of the invention, prior to administration of one or more physiological doses of exogenous IL-12, a patient population to be treated has IL-12 expression levels of less than about 5 pg/ml, less than about 4 pg/ml, less than about 3 pg/ml, less than about 2 pg/ml, or less than about 1 pg/ml. Generally the patient population would have IL-12 levels that are below the limit of detection or quantitation (LLPQ). Such IL-12 expression levels in a patient population having a disease, such as a chronic disease, or a wound, are indicative of a subject failing to produce desired or necessary levels of endogenous IL-12.

Landmark protein drugs that serve as replacements for endogenous factors include insulin (introduced in the 1960s), human growth hormone (HGH) (introduced in the 1980s), and EPO (introduced in the 1990s). It is envisioned that NM-IL-12 will serve this same role in the 2020s, either as a standalone treatment or in combination with standard of care treatment for chronic disease, injuries and aging.

Repair, regeneration, and eradication: Several model indications can function to demonstrate the breadth of IL-12 in repair, regeneration, and eradication and as a useful replacement immunotherapeutic. In particular, repair and regeneration can be demonstrated by the effectiveness of IL-12 in treating age-related macular degeneration (AMD), chronic kidney disease (CKD), wound healing, and osteoporosis (detailed below). Dendritic cells are the main producers of IL-12 in the body, but these cells become dysfunctional and no longer release IL-12, or release it in insufficient amounts, in certain disease states. Exogenous IL-12 can replace endogenous IL-12 (e.g., "a replacement immunotherapeutic") to stimulate repair and regeneration in conditions suffering from a lack of in vivo IL-12 production, such as a therapeutic in AMD, wound healing, osteoporosis, and CKD.

Safety: IL-12 is a unique cytokine. Recombinant human IL-12 (also referred to herein as "NM-IL-12", "IL-12", and HemaMax™ (rHuIL-12)) has been demonstrated to be safe. For example, safety of IL-12 has been demonstrated in >200 healthy volunteers in three studies and in patients in several clinical trials. See e.g., (i) ClinicalTrials.gov Identifier No. NCT02542124 for "NM-IL-12 in Cutaneous T-Cell Lymphoma (CTCL) Undergoing Total Skin Electron Beam Therapy (TSEBT) (on-going clinical trial); (ii) ClinicalTrials.gov Identifier No. NCT02544061 for "NM-IL-12 (rHuIL-12) in Subjects with Open Surgical Wounds (on-going clinical trial); (iii) ClinicalTrials.gov Identifier No. NCT02343133 for "Safety Study of HemaMax™ (rHuIL-12) to Treat Acute Radiation Syndrome" (completed clinical trial); and (iv) ClinicalTrials.gov Identifier No. NCT01742221 for "Safety and Tolerability of HemaMax™ (rHuIL-12) as Radiation Countermeasure" (completed clinical trial). NM-IL-12 is the only molecule proven to have potent effects on pancytopenia, significantly enhancing survival following bone marrow ablation via bone marrow regeneration. Further, IL-12 has been shown to reduce infections and bleeding, provide a survival benefit over Neupogen® in a head to head study, and is now in Phase 3 clinical studies. Efficacy studies have been completed for US Biologics License Application (BLA) approval.

Although NM-IL-12 is safe and well-tolerated, conventional wisdom in the pharmaceutical field has been that IL-12 is toxic. This is largely due to errors in a Phase 2 trial design which resulted in two patient deaths, while the Phase 1 trial which determined maximum tolerated dose and dosing schedule for NM-IL-12 was successfully completed. Early pharmaceutical researchers did not understand IL-12 biology, which lead to the error in the trial design. Subsequently, IL-12 has been evaluated in investigators in over 40 clinical trials and found to be well-tolerated (1389 patients).

Novel effects in injury/repair/regeneration: IL-12 is a master regulator of immunity and hematopoiesis. Because it is a master regulator, IL-12 is not constitutively produced in the body. IL-12 is only produced when it is needed upon injury, thus IL-12 is highly regulated in the body. However, aging, injuries, and many disease states, such as cancer and infectious diseases, and especially chronic disease states, affect the cells that produce IL-12 and inhibit its production. Thus, in chronic diseases, injuries, and in the aged, such as CKD, osteoporosis, AMD and diabetic wound healing, exogenous IL-12 can function as a replacement for the endogenous factor to repair injured tissue.

Figure 2:
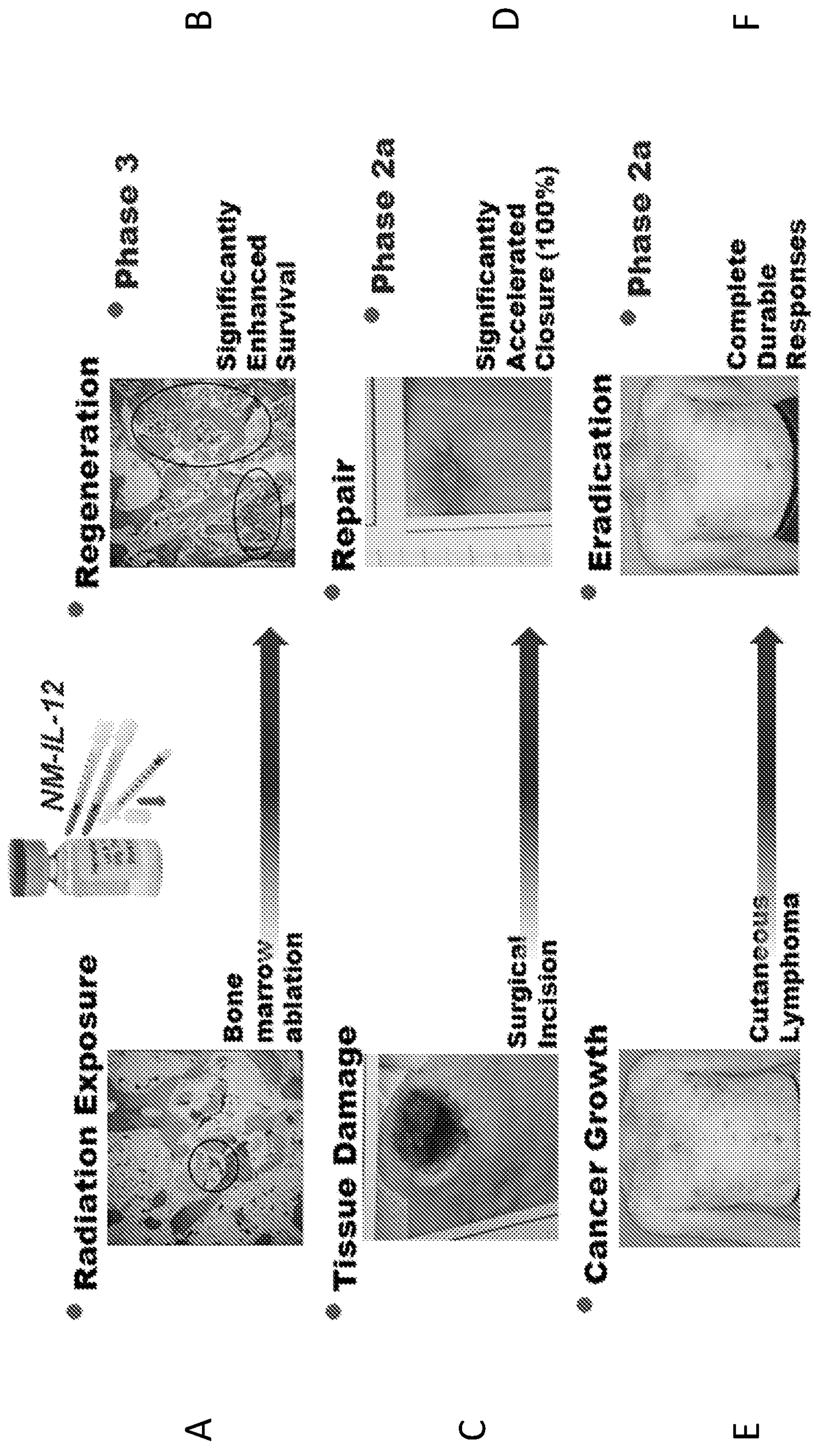
FIG. 2: Shows pictures of a non-clinical study in non-human primates evaluating NM-IL-12 after radiation exposure (e.g., bone marrow ablation) (FIG. 2A), demonstrating significantly enhanced cell regeneration (FIG. 2B). Further, NM-IL-12 has had clinical success in stoma takedown patients in demonstrating repair of tissue damage (FIG. 2C), with the molecule demonstrating significantly accelerated closure (100%) of tissue damage caused by surgical incisions (FIG. 2D). Finally, NM-IL-12 has shown clinical success in eradicating tumor growth, with IL-12 used to treat cutaneous T cell lymphoma patients (FIG. 2E) resulting in eradication and complete durable responses (FIG. 2F).

NM-IL-12 has had clinical success in radiation exposure (e.g., bone marrow ablation), demonstrating significantly enhanced survival (FIG. 2). Further, NM-IL-12 has had clinical success in demonstrating repair of tissue damage, with the molecule demonstrating significantly accelerated closure (100%) of tissue damage caused by surgical incisions (FIG. 2). Finally, NM-IL-12 has shown clinical success in eradicating cancer growth, with IL-12 used to treat cutaneous lymphoma resulting in eradication and complete durable responses (FIG. 2).

NM-IL-12 has unique mechanisms of action. Specifically, IL-12 acts at the level of hematopoietic stem cells to regenerate cells in the bone marrow and mobilize these progenitor and stem cells from the bone marrow to the peripheral blood and into injured tissues and organs. Further, the molecule proliferates and activates key cytotoxic immune cells, CD8+ and NK cells, to fight pathological invaders, such as infections and cancer. Therefore, NM-IL-12 uniquely provides potent anti-infectivity and anti-tumor effects along with hematopoietic regeneration of the bone marrow. Further, the fact that the unique IL-12 receptor is on both mature, immune effector cells, CD8+, CD4+, NK and B cells, and on immature bone marrow progenitor and stems cells, underscores its importance in the body to allow for new precursor cells to come forth from the bone marrow to lead to mature effector cells for repeated rounds of immune activity.

Figure 1:
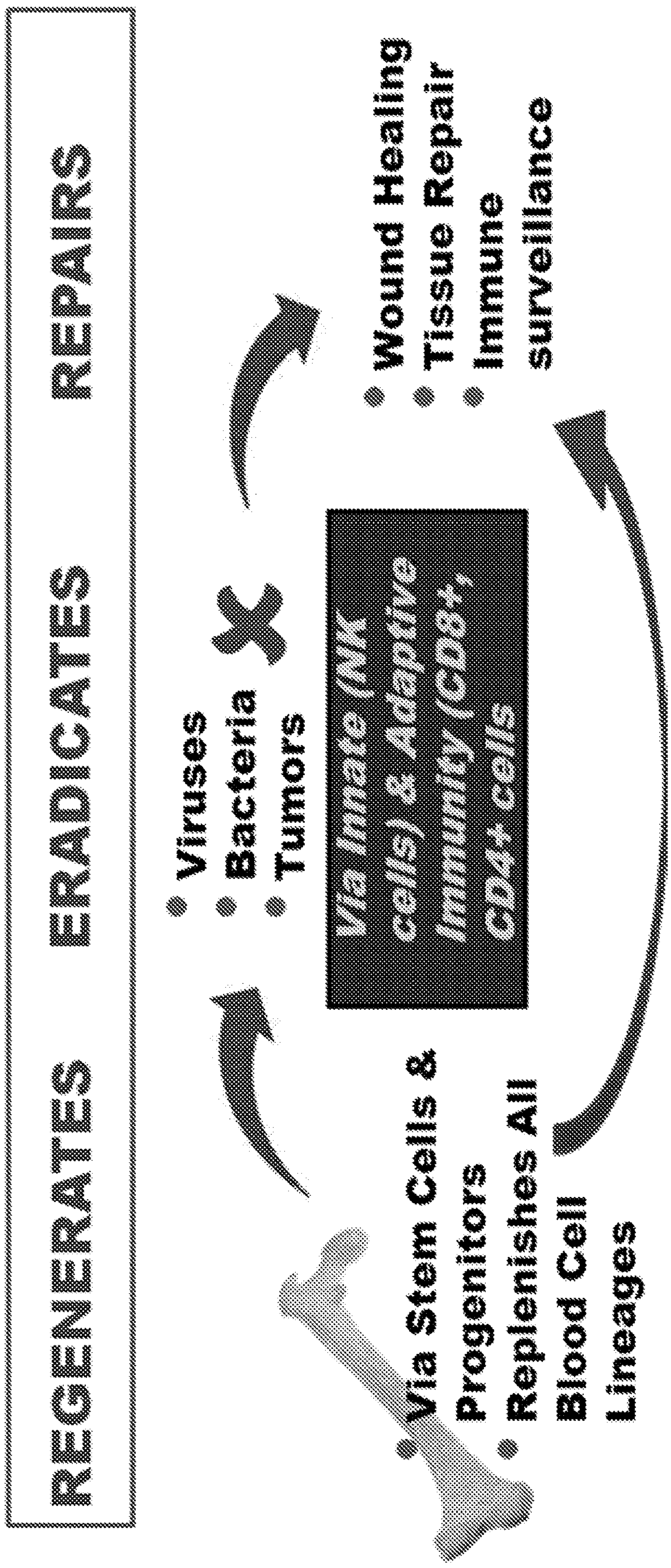
FIG. 1: Graphically demonstrates that NM-IL-12 is a stem cell, hematopoietic and immune cell factor which regenerates (via stem cells and progenitors, functioning to replenish all blood cell lineages), eradicates (viruses, bacteria, and tumors via innate (NK cells) and adaptive immunity (CD8+ and CD4+ cells), and repairs (wound healing, tissue repair, and immune surveillance.
Figure 3:
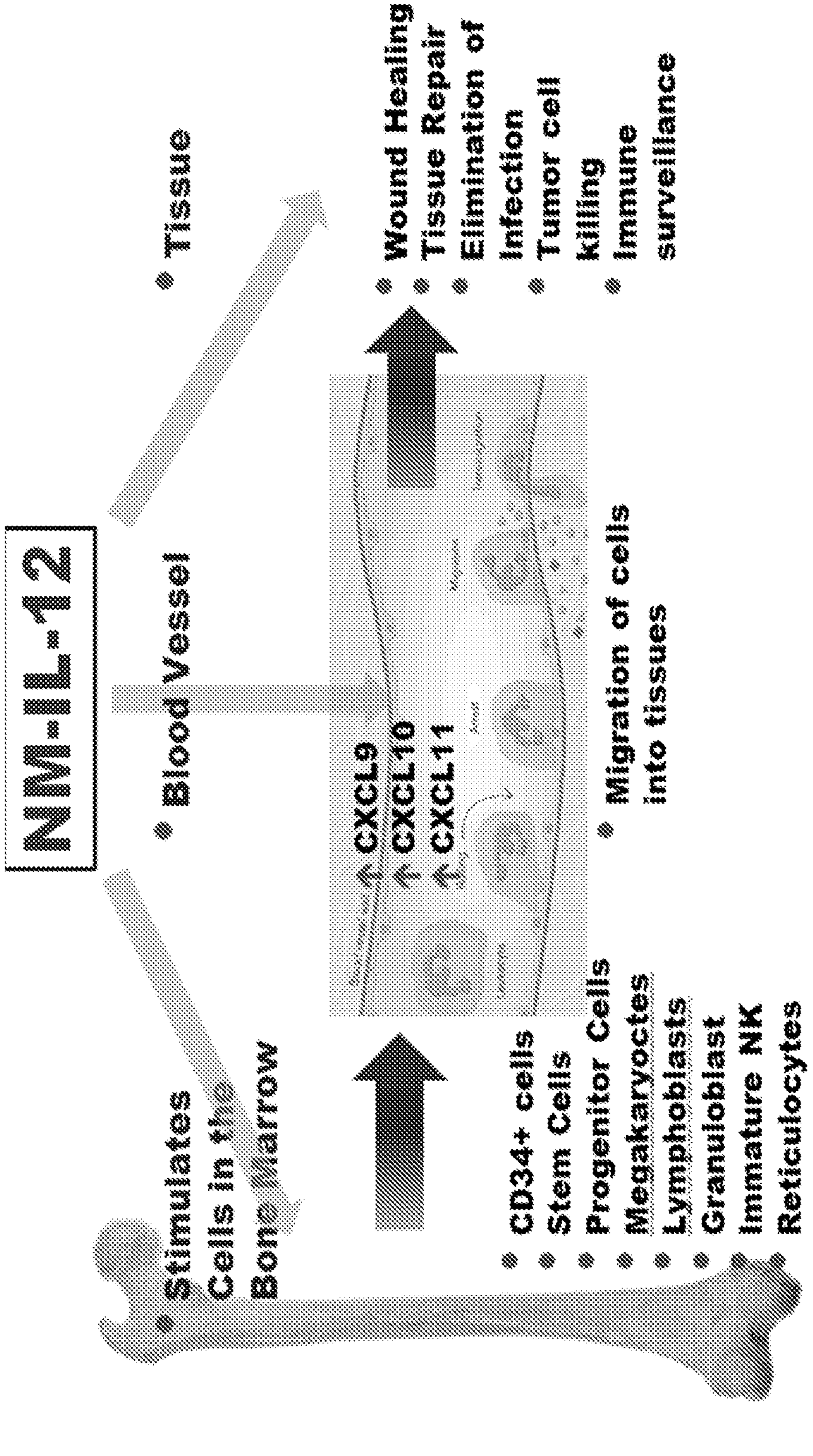
FIG. 3: Graphically depicts how NM-IL-12 stimulates hematopoiesis by stimulating cells in the bone marrow, such as CD34+ cells, stem cells, progenitor cells, megakaryocytes, lymphoblasts, granuloblasts, immature NK cells, and reticulocytes. NM-IL-12 also facilitates migration of cells from the blood into tissues, to aid in wound healing and tissue repair.

As shown in FIG. 1, NM-IL-12 is a stem cell, hematopoietic and immune cell factor which regenerates (via stem cells and progenitors, functioning to replenish all blood cell lineages), eradicates (viruses, bacteria, and tumors via innate (NK cells) and adaptive immunity (CD8+ and CD4+ cells), and repairs (wound healing, tissue repair, and immune surveillance. Accordingly, NM-IL-12 stimulates hematopoiesis by stimulating cells in the bone marrow, such as CD34+ cells, stem cells, progenitor cells, megakaryocytes, lymphoblasts, granuloblasts, immature NK cells, and reticulocytes. NM-IL-12 also facilitates migration of cells into tissue, to aid in wound healing and tissue repair. See FIG. 3.

Figure 4:
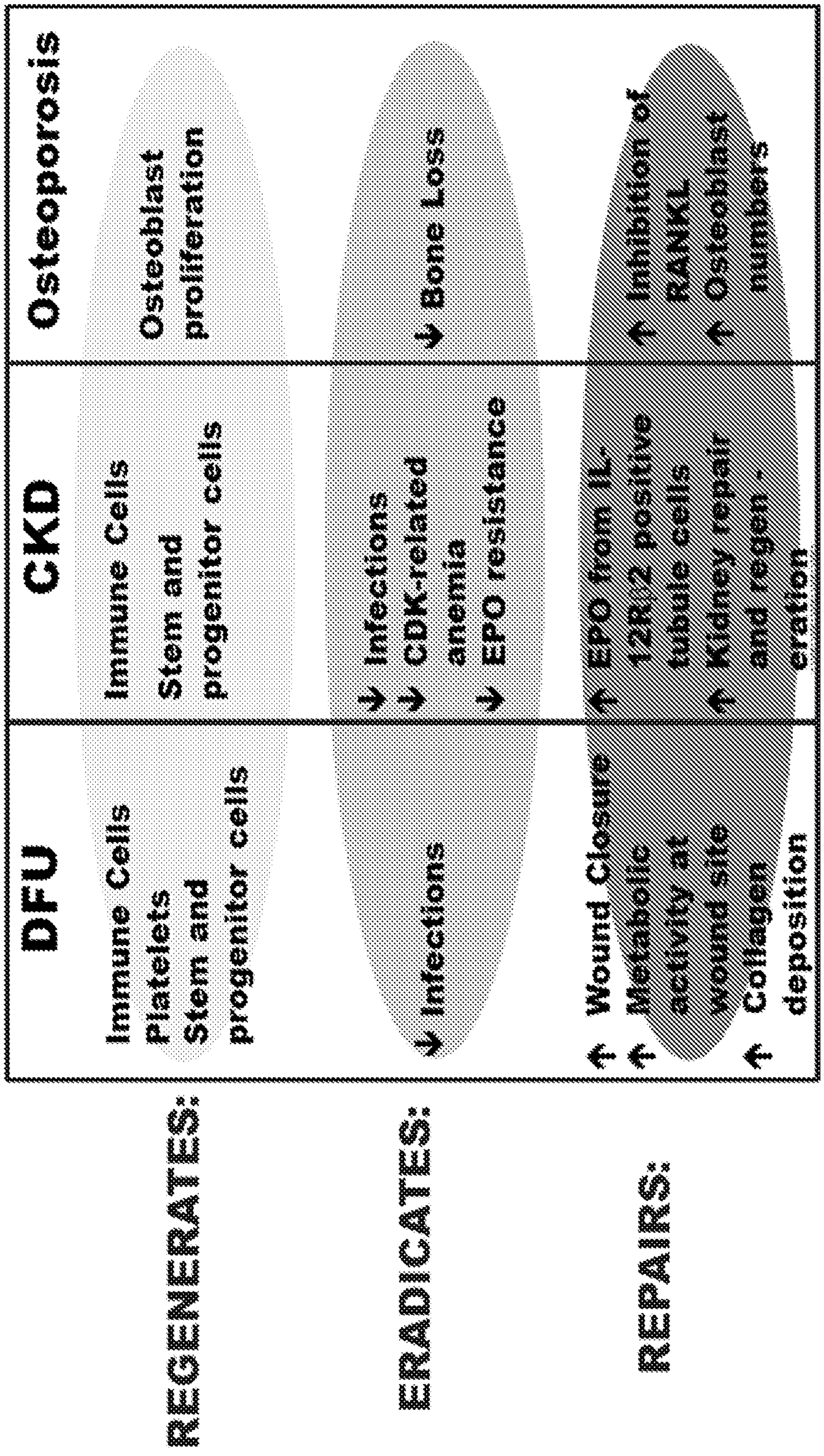
FIG. 4: Graphically shows the effects of NM-IL-12 when inducing regeneration, eradication, and repair in three exemplary disease conditions: diabetic foot ulcers (DFU), chronic kidney disease (CKD), and osteoporosis.

As examples of the effectiveness of IL-12 as a replacement immunotherapeutic, NM-IL-12 has been found to accelerate wound healing in diabetic foot ulcers (DFU), slow progression of chronic kidney disease (CKD), and reduce bone loss in osteoporosis. Specifically, in DFU NM-IL-12 has been found to (i) regenerate immune cells, platelets, stem cells and progenitor cells (e.g., regenerate), (ii) decrease infections (e.g., eradicate), and (iii) improve wound closures, increase metabolic activity at wound side, and increase collagen deposition (e.g., repair). Similarly, in CKD NM-IL-12 has been found to (i) regenerate immune cells, stem cells, and progenitor cells (e.g., regenerate), (ii) decrease CKD-related anemia, and decrease EPO resistance (e.g., eradicate), and (iii) increase EPO from IL-12Rbeta2 positive tubule cells and increase kidney repair and regenerate (e.g., repair). Finally, in treating osteoporosis, NM-IL-12 has been found to (i) trigger osteoblast proliferation (e.g., regeneration); (ii) decrease bone loss (e.g., eradicate), and (iii) increase inhibition of NF-kappaB ligand (RANKL) and increase osteoblast numbers. See FIG. 4.

Figure 5:
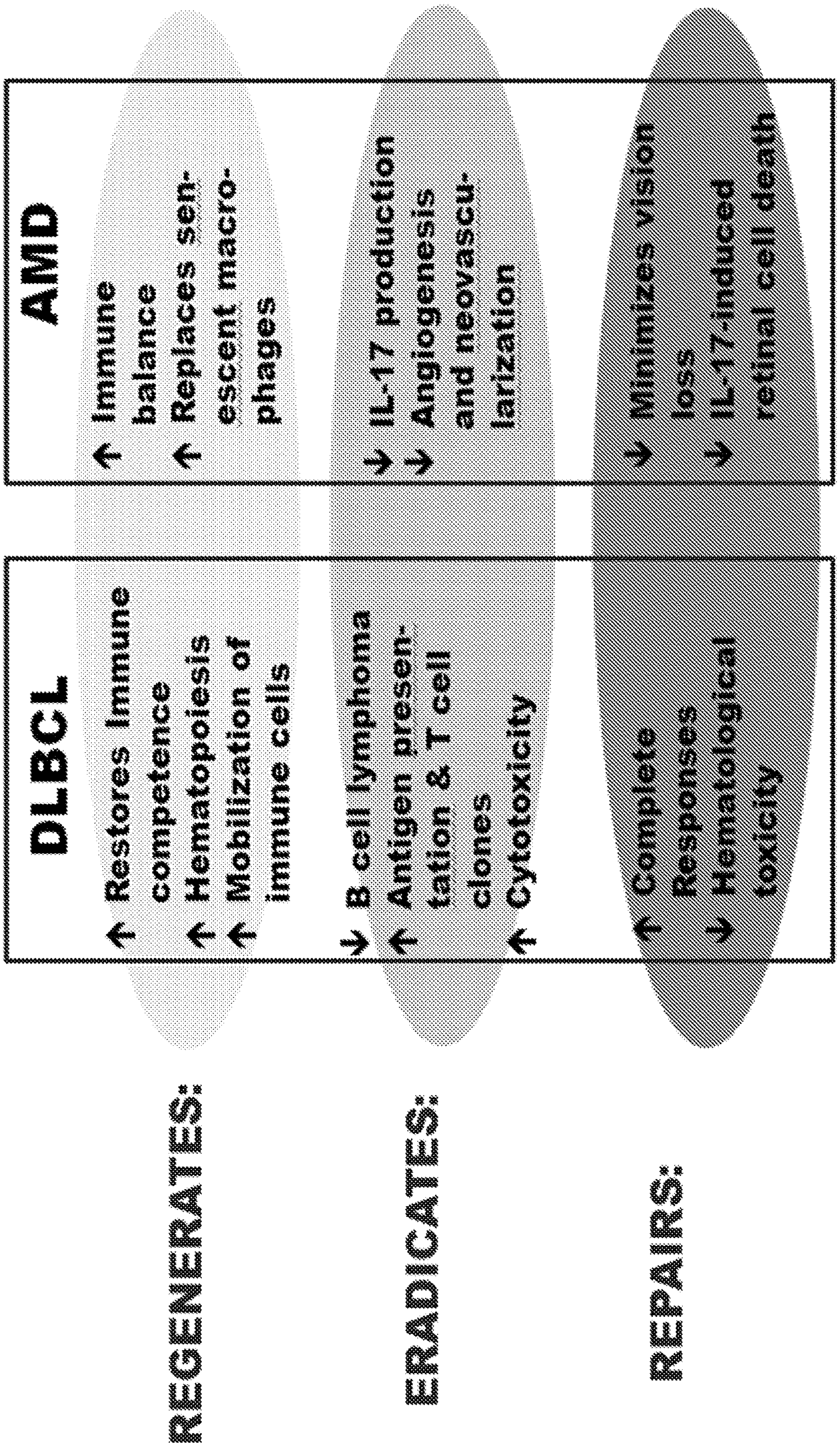
FIG. 5: Graphically shows the effects of NM-IL-12 when inducing regeneration, eradication, and repair NM-IL-12 in two exemplary disease conditions: Diffuse large B-cell lymphoma (DLBCL) and age-related macular degeneration (AMD).

NM-IL-12 has also been found to increase cure rates and lower chemotherapy-related toxicity in Diffuse large B-cell lymphoma (DLBCL or DLBL) and to inhibit progression of age-related macular degeneration (AMD). Specifically, in DLBCL, IL-12 has been found to (i) restore immune competence, increase hematopoiesis, and mobilize immune cells (e.g., regenerate); (ii) decrease B cell lymphoma, increase antigen presentation and T cell clones, and increase cytotoxicity (e.g., eradiate); and (iii) increase complete responses and decrease hematological toxicity (e.g., repair). Further, with respect to AMD, NM-IL-12 has been found to (i) increase immune balance and increase replacement of senescent macrophage (e.g., regenerate); (ii) decrease IL-17 production and decrease angiogenesis and neovascularlization (e.g., eradicate); and (iii) minimize vision loss and decrease IL-17-induced retinal cell death (e.g., repair). See FIG. 5.

Thus, NM-IL-12 provides a revolutionary regenerative approach, with three main effects: regeneration, eradication and repair. In hematology, NM-IL-12 can treat for example pancytopenia, neutropenia, anemia, thrombocytopenia, and/or lymphopenia (simultaneously or any combination thereof). Not only does IL-12 mitigate the hematological toxicity caused by a primary therapy, but IL-12 also provides synergistic, eradication (anti-tumor) responses in oncology patients. Patients also receive additional benefits, with little or no toxicity over the primary therapy when used a combination treatment. Treatment with NM-IL-12 is predicted to yield a survival benefit over the primary therapy alone. No other factor is known to have these revolutionary effects.

Administration of exogenous IL-12 as a replacement immunotherapeutic can be combined with any conventional treatment for the condition to be treated. The combination treatment can comprise sequential administration, simultaneous administration, or co-administration separated by any desirable time period, including hours, days, weeks, or months.

A. Chronic Kidney Disease

As noted above, CKD is a model indication demonstrating the usefulness of IL-12 as a replacement immunotherapeutic. To date, there are no drugs in the CKD market or pipeline that can actually slow progression of CKD. NM-IL-12 thus serves an unmet need in the art. NM-IL-12 induces endogenous EPO production, increases reticulocytes and red blood cells in normal humans and monkeys, and increases reticulocytes and red blood cells following lethal radiation in non-human primates. But NM-IL-12 does more than deliver EPO to increase the red blood cell population—NM-IL-12's pleiotropic effects also are expected to lead to repair and regeneration of the kidney, thereby slowing progression of CKD. Preliminary data indicate that NM-IL-12 is a novel treatment for renal anemia in CKD patients, particularly early stage patients, where it may slow progression of CKD. NM-IL-12's pleiotropic effects in CKD are anticipated to slow CKD progression, especially due to its stem cell activity in the bone marrow and its ability to mobilize stem cells, such as CD34+ and mesenchymal cells from the bone marrow to peripheral tissues for repair and regeneration. NM-IL-12 also induces EPO release from IL-12Rbeta2+ve kidney tubule cells and reduces CKD-related anemia. Further, NM-IL-12 mobilizes hematopoietic progenitor and stem cells and mature immune cells, leading to kidney repair and regeneration. Finally, NM-IL-12 restores immune balance, reduces EPO resistance, and decreases infection rates.

A measureable endpoint for successful treatment of CKD using NM-IL-12 is slowed CKD progression. Alternatively, generation of EPO and its associated change in blood parameters, such as hemoglobin levels, is also an available as a clinical endpoint. The slowing of progression of CKD can be demonstrated by, for example, one or more in the subject of the following: a decrease in creatinine, a decrease in blood urea nitrogen (BUN), a decrease in albuminuria, or an increase in glomerular filtration rate (GFR). In one embodiment of the invention, treatment with NM-IL-12 slows progression of CKD, e.g., by measurement of kidney function, creatinine measurements, hemoglobin levels, generation of EPO, BUN, GFR, albuminuria—or any combination thereof—by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Table 1 below details the five stages of chronic kidney disease, including the amount of kidney function remaining at each stage, as well as a description and symptoms associated with each stage.

TABLE 1

The five stages of chronic kidney disease

| | STAGE 1 | STAGE 2 | STAGE 3 | STAGE 4 | STAGE 5 |
|---|---|---|---|---|---|
| Amount of kidney function remaining at each state | More than 90% | 60 to 89% | 30 to 59% | 15 to 29% | Less than 15% |
| Description of each stage | Early kidney damage with normal or even increased function. | Worse kidney damage with reduced function. | Even worse kidney damage with less function. | Kidney damage is so severe with such poor function that the kidneys are barely able to keep the person alive. | End-stage Renal Disease; kidney function is severely impaired. The kidneys are not working well enough to keep the person alive. |
| Symptoms | No symptoms observed. Urea and creatinine levels are normal | No symptoms observed. Urea and creatinine levels are normal, or mildly elevated. | Early symptoms occur and may include tiredness, poor appetite, and itching. Creatinine level | Tiredness, poor appetite, and itching may get worse | Symptoms may include poor sleeping at night, difficulty breathing, itchiness, and frequent |

TABLE 1-continued

| The five stages of chronic kidney disease | | | | | |
|---|---|---|---|---|---|
| | STAGE 1 | STAGE 2 | STAGE 3 | STAGE 4 | STAGE 5 |
| | | | rises, excess urea is present, and anemia may begin to occur. | | vomiting. High levels of creatinine and urea are present. |
| eGFR (estimated Glomerular Filtration Rate) | 90 ml/min or more | 60-89 ml/min | 30-59 ml/min | 15-29 ml/min | 15 ml/min or less |
| Treatment options* | Identify course and try to reverse it. | Monitor creatinine level, blood pressure, and general health and well-being. Try to stop or slow the worsening kidney function. | Continue to try to stop or slow the worsening kidney function. Patient learns more about the disease and treatment options. | Plan and create access site for dialysis. Receive assessment for possible transplant. | Start renal replacement therapy; dialysis or transplantation. |

As noted above, the slowing of progression of CKD can be demonstrated, for example, by one or more in the subject of a decrease of creatinine, decrease of blood urea nitrogen (BUN), decrease in albuminuria, or an increase in glomerular filtration rate (GFR). Table 2 below details the prognosis for CKD as determined by GFR and albuminuria categories.

TABLE 2

| Prognosis of CKD by GFR and Albuminuria Categories | | | | Albuminuria categories Description and range | | |
|---|---|---|---|---|---|---|
| | | | | A1 Normal to mildly increased <30 mg/g <3 mg/mmol | A2 Moderately increased 30-299 mg/g 3-29 mg/mmol | A3 Severely increased >300 mg/g >30 mg/mmol |
| GFR categories ($ml/min/1.73\ m^2$ | G1 | Normal or high | >90 | Low risk | Moderately increased risk | High risk |
| | G2 | Mildly decreased | 60-90 | Low risk | Moderately increased risk | High risk |
| Description and range | G3a | Mildly to moderately decreased | 45-59 | Moderately increased risk | High risk | Very high risk |
| | G3b | Moderately to severely decreased | 30-44 | High risk | Very high risk | Very high risk |
| | G4 | Severely decreased | 15-29 | Very high risk | Very high risk | Very high risk |
| | G5 | Kidney failure | <15 | Very high risk | Very high risk | Very high risk |

Green: low risk (if no other markers of kidney disease, no CKD); Yellow: moderately increased risk; Orange: high risk; Red, very high risk.
KDIGO 2012

Figure 9:
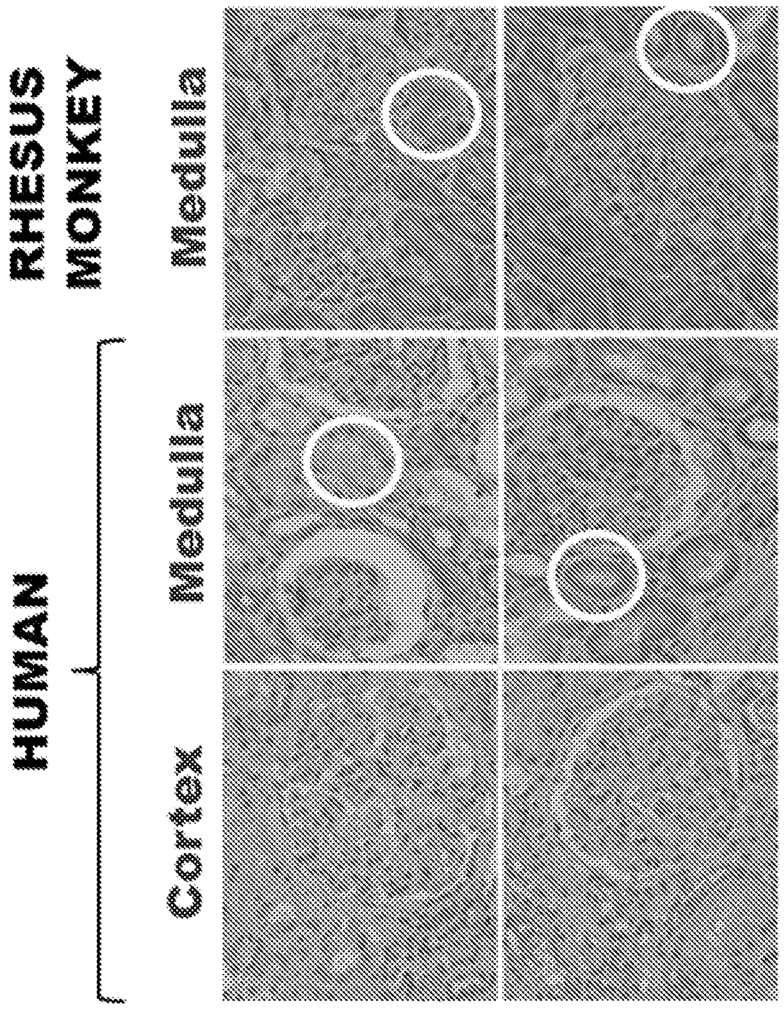
FIG. 9: Shows that the expression of EPO is indicated to arise from kidney medullary tubules. Slides from human cortex and medulla are shown, along with slides from Rhesus monkey medulla, and illustrate expression of IL-12Rbeta2 in medullary, tubules in humans and Rhesus monkeys, but not in the human cortical tubules.
Figure 10:
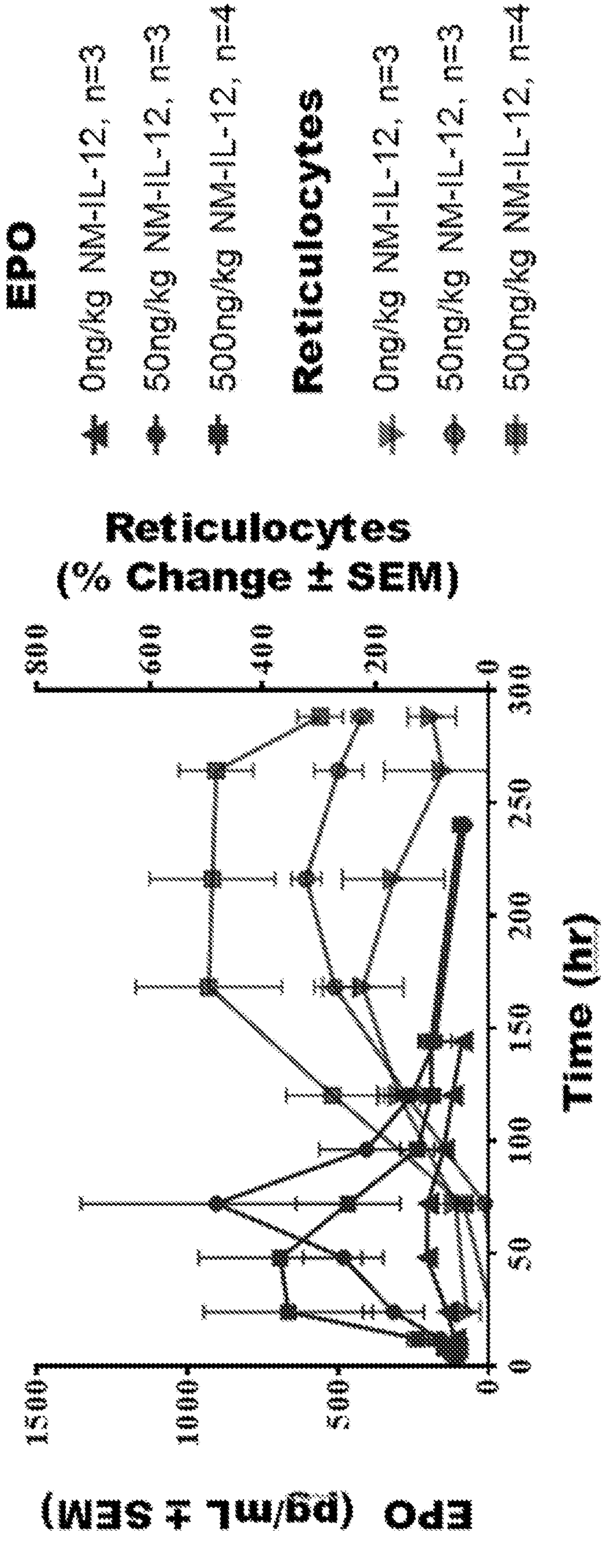
FIG. 10: Shows that a single, low dose of NM-IL-12 induces EPO in Rhesus monkeys and leads to increases in reticulocytes, the precursors of red blood cells. EPG (pg/mL) vs time is shown for 3 treatment groups: Group 1=0 ng/kg NM-IL-12 (n=3); Group 2=50 ng/kg NM-IL-12 (n=3); and Group 3=500 ng/kg NM-IL-12 (n=4). Also shown in the figure is a graph of reticulocytes (% change) vs time for the same 3 treatment groups.

The unique subunit of the IL-12 receptor (IL-12Rb2) is expressed on kidney medullary tubule cells in humans and Rhesus monkeys. IL-12Rbeta2 is heavily stained in medullary tubule cells (but not cortical kidney tubules) comprising the nephron. This is significant in that the expression of EPO is indicated to arise from kidney medullary tubules. FIG. 9. A single, low dose of NM-IL-12 induces EPO in Rhesus monkeys and leads to increases in reticulocytes, the precursors of red blood cells. FIG. 10. Further, a single, low dose of NM-IL-12 significantly reduces the nadir of major blood cell types following myeloablation (lethal radiation) in monkeys in the absence of supportive care. NM-IL-12 shows a unique, multilineage regenerative effect via activity on hematopoietic stem cells, and a positive effect on erythropoiesis. See Table 3.

TABLE 3

| Cell Type | NM-IL-12 vs. Control |
|---|---|
| Reticulocytes | 0.056* |
| Red Blood Cells | 0.012** |
| Platelets | 0.012** |
| White Blood Cells | 0.022** |
| Lymphocytes | 0.068* |
| Neutrophils | 0.028** |

Figure 11:
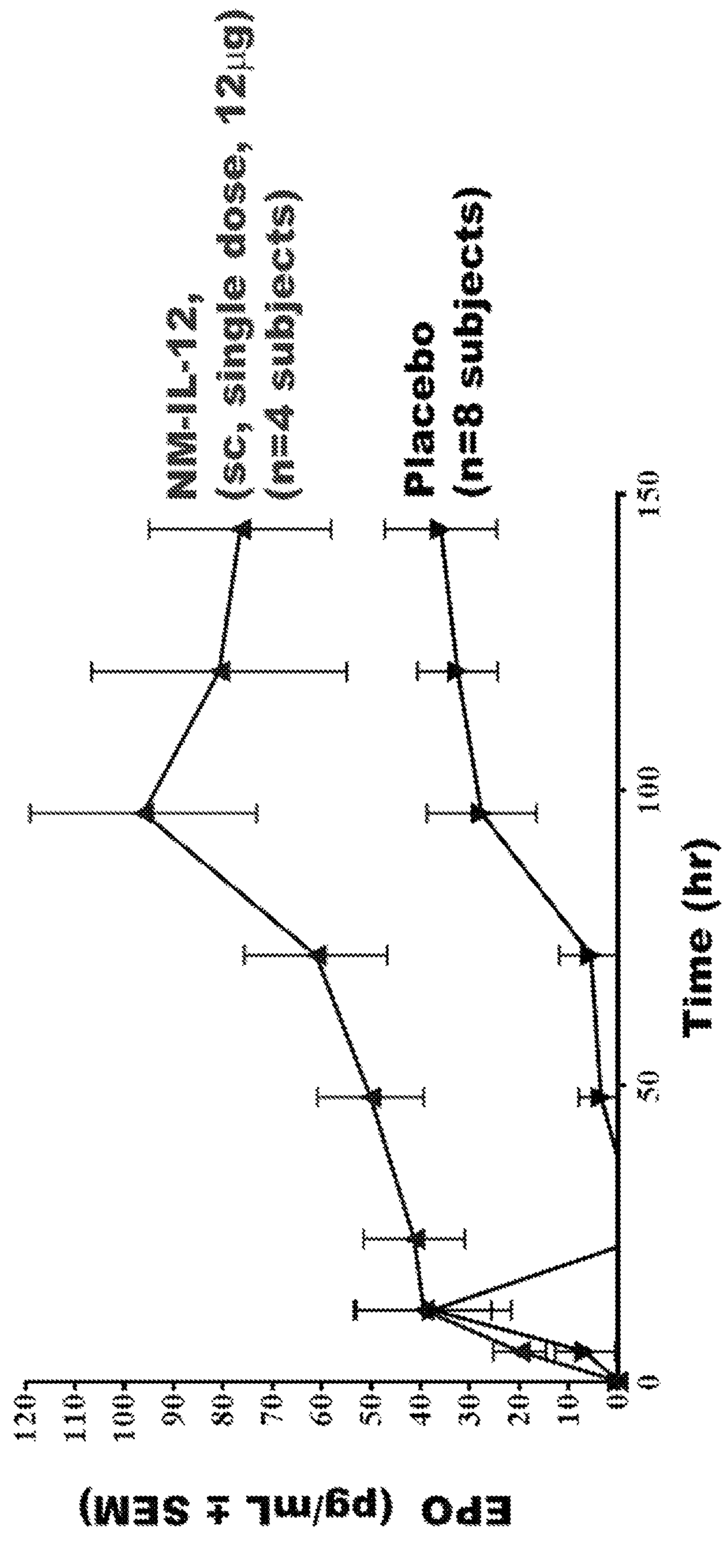
FIG. 11: Shows that a single low dose of NM-IL-12 (12 μg) directly induces EPO in humans. The graph depicted shows EPO (pg/mL) over time for two treatment groups: Group 1=NM-IL-12 administered SC, single dose at 12 μg, with n=4 subjects; and Group 2=placebo, with n=8 subjects.
Figure 12:
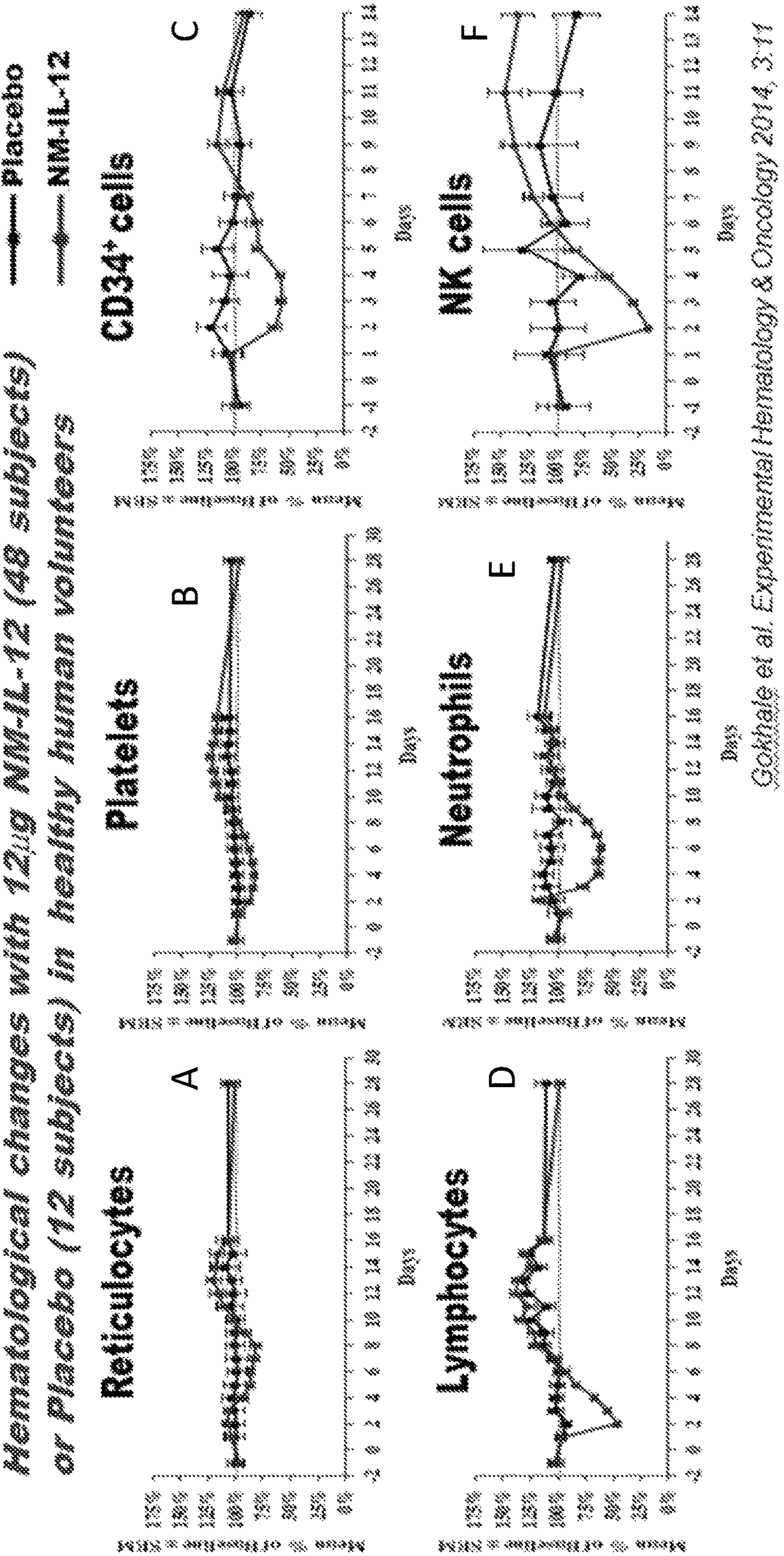
FIG. 12: Shows that a single, low dose SC injection of NM-IL-12 was found to mobilize circulating mature peripheral blood cells and immature CD34+ hematopoietic progenitor cells for tissue repair and regeneration, as needed in the body.

Statistical evaluation by Wilcoxon Rank-sum Test.
**Statistically significant
*Trend toward significance Moreover, a single low dose of NM-IL-12 (12 mg) directly induces EPO in humans. FIG. 11. A single, low dose SC injection of NM-IL-12 was found to mobilize all mature peripheral blood cells and immature CD34+ hematopoietic progenitor cells for tissue repair and regeneration, as needed in the body. FIG. 12. These results demonstrate a unique multipotent and consistent mobilization effect for NM-IL-12. Thus, while EPO is the current standard treatment for CKD, NM-IL-12 offers broad and unique pleiotropic benefits over EPO in CKD. Table 4.

TABLE 4

| | NM-IL-12 | EPO |
|---|---|---|
| Enhances EPO levels | ✓ | ✓ |
| Increases Reticulocytes and Red Blood | ✓ | ✓ |
| Cells | ✓ | x |
| Promotes Hematopoletic Progenitors, | ✓ | x |
| Stem Cells and Immune Cells | ✓ | x |
| Mobilizes Cells to the Kidney | ✓ | x |
| Promotes Kidney Repair and | ✓ | x |
| Regeneration | ✓ | x |
| Restores Immune Balance | ✓ | x |
| Reduces EPO resistance | ✓ | x |
| Decreases Infection Rate | ✓ | x |

In one embodiment of the invention, NM-IL-12 is used in combination with a conventional treatment for CKD, such as EPO.

Exemplary literature support demonstrating IL-12 activity as detailed herein includes, e.g., (1) publications teaching that IL-12 and EPO are in a endogenous feedback loop, and there is a negative correlation between low IL-12 levels and EPO resistance, including "Erythropoietin enhances immunostimulatory properties of immature dendritic cells," *Clin. and Exp. Immunology,* 165: 202-210 (2011); and "Role of cytokines in response to erythropoietin in hemodialysis patients," *Kidney International,* 54:1337-43 (1998); (2) publications teaching that uremic toxicity impairs adaptive and innate immune response and release of IL-12, leading to immune dysfunction, including "Characteristics and causes of immune dysfunction related to uremia and dialysis." Proceedings Of The 3rd Asian Chapter Meeting Of The ISPD, 28(3) June 2008, and *Kidney International,* 54:1337-43 (1998); and (3) publications teaching that dialysis patients that can express endogenous IL-12 have longer survival, including "Cytokine patterns and survival in haemodialysis patients," Nephrol. Dial. Transplant, 25: 1239-1243 (2010).

B. Wound Immunotherapy

Figure 13:
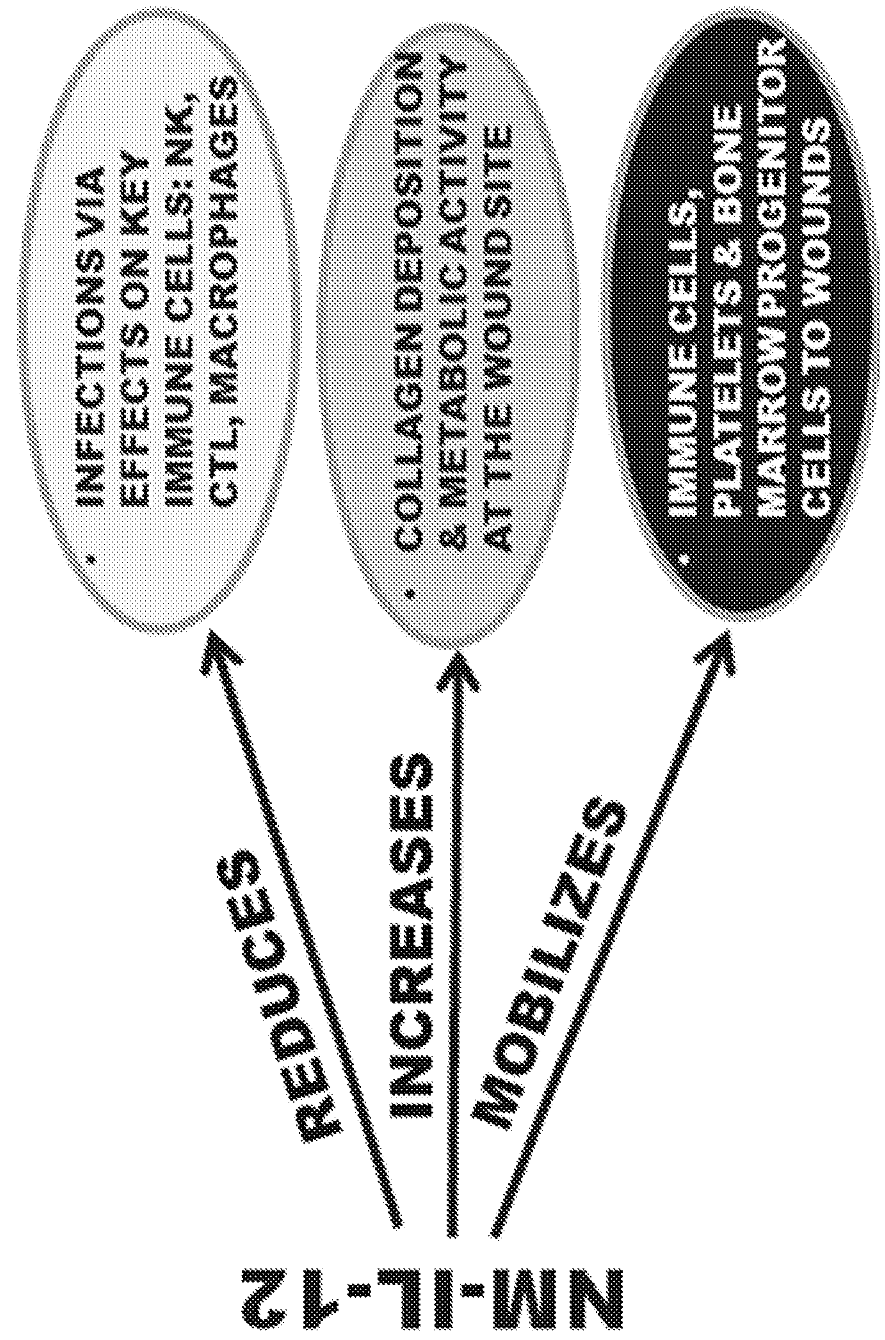
FIG. 13: Visually depicts the anticipated usefulness of IL-12 in accelerating closure of slow healing wounds in diabetic patients and in the elderly with non-healing wounds.

IL-12 is also useful in tissue repair, and in particular to aid and improve wound healing. A model injury used to demonstrate the usefulness of IL-12 in tissue repair are wounds in diabetic and elderly patients, which can be particularly difficult to treat. In other embodiments, the subject is elderly and has a pressure ulcer, or the subject is diabetic and has a foot ulcer. To date, there are no drugs that significantly improve slow healing wounds in diabetic and elderly patients. The novel findings described herein show that the IL-12 receptor is found in progenitor cells of the skin and that this receptor is upregulated in the wound surface, and that murine IL-12 accelerates wound closure in immunocompromised and diabetic murine models. These findings pave the way for the use of NM-IL-12 in wound immunotherapy generally, and particularly in slow healing wounds found in diabetics and the elderly. See e.g., FIG. 13, which visually depicts the anticipated usefulness of IL-12 in accelerating closure of slow healing wounds in diabetic patients and in the elderly. In particular, IL-12 is anticipated to (i) reduce infections via key effects on immune cells such as NK cells, cytotoxic T cell (CTLs), and macrophages; (ii) increase collagen deposition and metabolic activity at the wound site; and (iii) mobilize immune cells, platelets, and bone marrow progenitor and stem cells to wounds.

Accelerated wound healing following surgery in stoma takedown patients represents proof-of concept for the effect of NM-IL-12 in wound immunotherapy, which can pave the way for a Phase 2b trial in diabetic foot ulcer patients (DFU). There are no drugs available that can effectively prevent or treat diabetic foot ulcers. A clinical endpoint of improved wound closure in DFU patients would be eligible for an accelerated, conditional approval given the high unmet need.

In one embodiment of the invention, administration of exogenous IL-12 results in accelerating wound healing, as compared to the rate of healing observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Scientific Support In Wound Immunotherapy: The IL-12 receptor is expressed in progenitor cells in the dermis and sebaceous glands, and is upregulated in the wound surface after wounding and radiation. A previously unidentified role for IL-12 in the stimulation of wound healing is demonstrated in normal FIG. 14A and wounded, irradiated skin tissue (FIGS. 14B and 14C). In normal, uninjured skin, the IL-12 receptor is found to be highly expressed on progenitor cells in the basement membrane (BM) of the dermis and in sebaceous (SE) glands underlying hair follicles. These progenitor cells are the primary mediators of re-epithelialization following cutaneous injury. Following full-thickness injury, which is equivalent to a third degree burn, the IL-12 receptor is seen to be highly upregulated in expression at the wound surface. These data provide the basis for stimulation of wound healing by NM-IL-12 following cutaneous injury.

Figure 15:
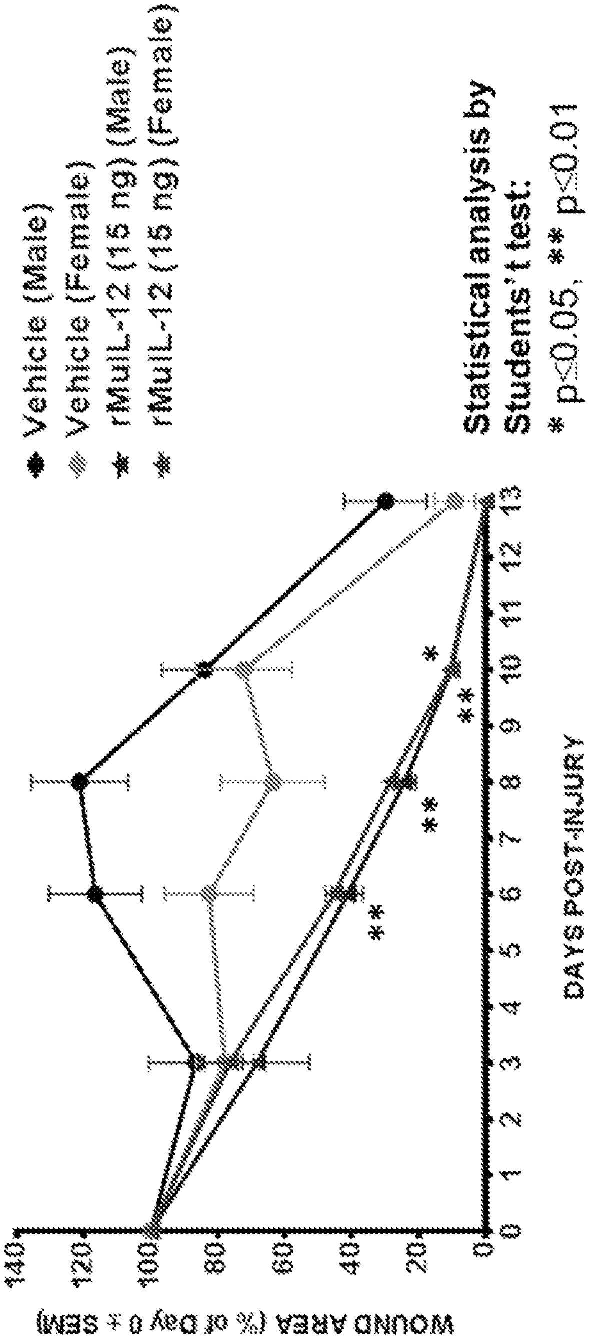
FIG. 15: Shows a graph of wound area (expressed as a % of day 0) vs days post-injury, with a comparison between results obtain with topical administration of a vehicle or recombinant murine IL-12 (at 15 ng), to both male and female mice. Administration of recombinant murine IL-12 (rMuIL-12, 15 ng, topically) to male and female mice given total body irradiation (TBI, 500 cGy) and a full thickness cutaneous injury, at the time of injury and on days 3 and 6 after injury, significantly accelerated wound healing and gave full wound closure, as compared with vehicle-treated mice. Statistical analysis by Students' t test, $*p \leq 0.05$, $**p \leq 0.01$.

Further, topical NM-IL-12 has been found to accelerate wound healing in a full-thickness, immunosuppressed murine model. See FIG. 15. In particular, FIG. 15 shows a graph of would area (% of day 0) vs days post-injury, with a comparison between results obtain with topical administration of a vehicle (male and female) and recombinant murine IL-12 (at 15 ng), for both male and female mice. Administration of rMuIL-12 (15 ng, topically) to male and female mice given TBI (500 cGy) and a full thickness cutaneous injury, at the time of injury and on days 3 and 6 after injury, accelerated wound healing and gave full wound closure, as compared with vehicle-treated mice.

Figure 16:
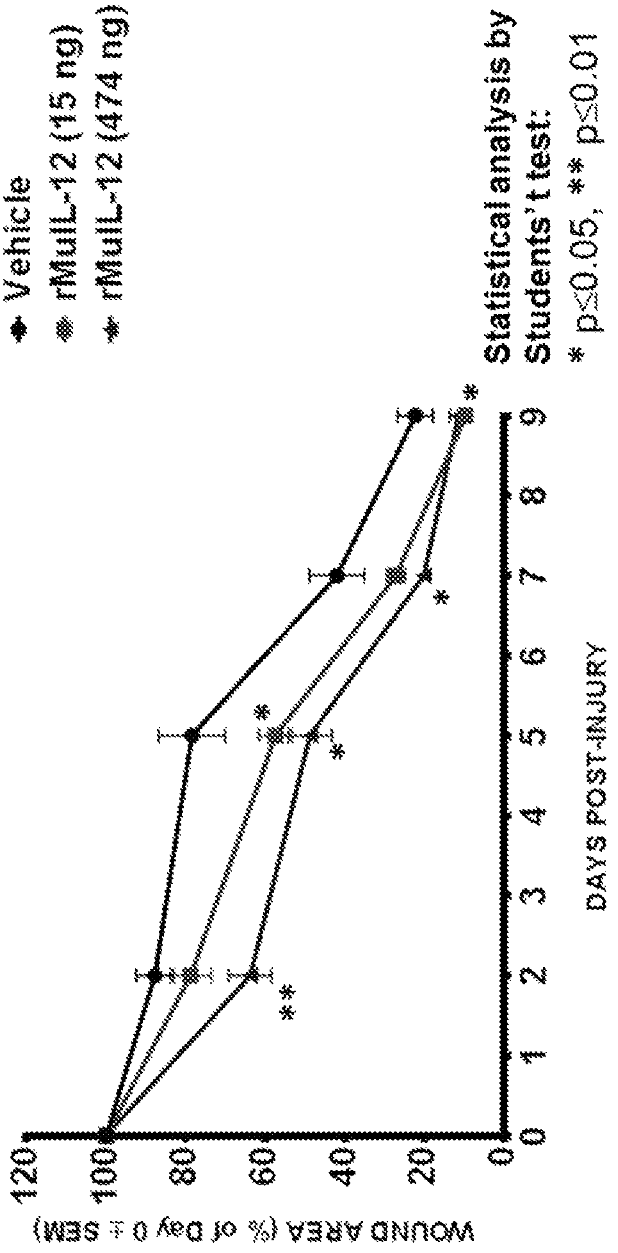
FIG. 16: Shows a graph of wound area (expressed as a % of day 0) vs days post-injury, with a comparison between results obtain with topical administration of a vehicle and two different dosages of recombinant murine IL-12 (rMuIL-12, 15 and 474 ng, topically), in Zucker rats with a diabetic background. A single administration of rMuIL-12 significantly accelerated healing of the full-thickness injury. Statistical analysis by Students' t test, $*p \leq 0.05$, $**p \leq 0.01$.

Additional data showed that topical NM-IL-12 accelerates wound healing in a full-thickness, diabetic murine model. Specifically, as shown in FIG. 16, administration of rMuIL-12 (15 ng and 474 ng, topically.) to diabetic rats with a full thickness cutaneous injury, at the time of injury, accelerated wound healing compared with vehicle-treated rats. (FIG. 16 shows a graph of would area (% of day 0) vs days post-injury, with a comparison between results obtain with topical administration of a vehicle and two different dosages of recombinant murine IL-12.)

Figure 17:
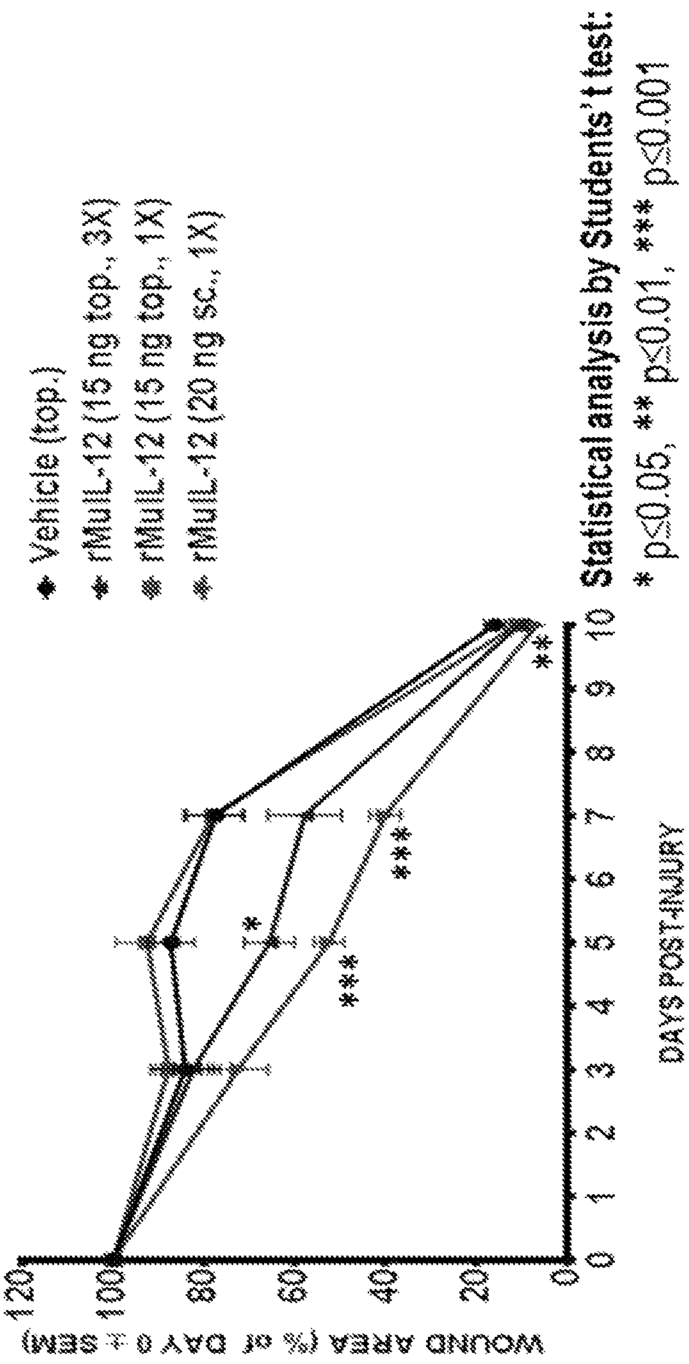
FIG. 17: Shows a graph of wound area (expressed as a % of day 0) vs days post injury for 4 treatment groups: vehicle (topical), 15 ng rMuIL-12 topical 3×/day, 15 ng rMuIL-12 topical 1×/day, and 20 ng rMuIL-12 subcutaneously (SC) 1×/day. Animals receiving 20 ng rMuIL-12 SC 1×/day showed significantly the fastest wound healing, with animals receiving 15 ng rMuIL-12 topical 3×/day having the next fastest healing rate. Statistical analysis by Students' t test, $*p \leq 0.05$, $p \leq 0.01$, $*p \leq 0.001$.
Figure 18:
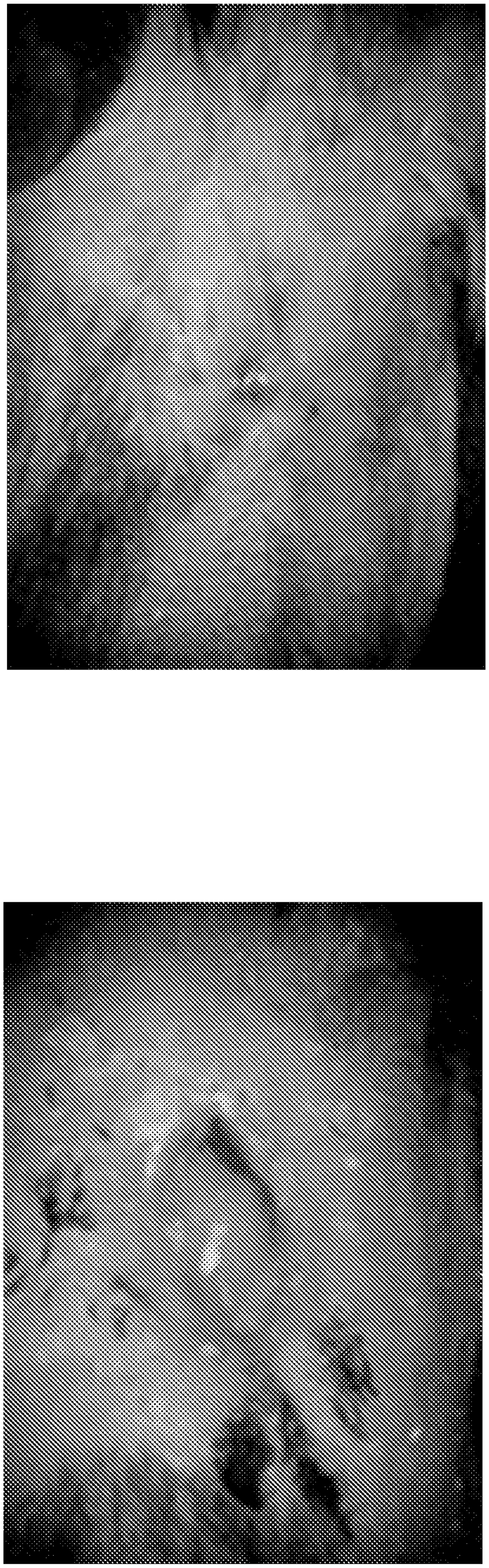
FIG. 18.

Wound healing data is not limited to topical administration. In particular, a single SC injection of murine NM-IL-12 was found to accelerate wound healing in a full-thickness murine model and is superior to topical administrations. See e.g., FIGS. 17 and 18. A single administration (sc) of rMuIL-12 (20 ng) 24 hr after a full thickness cutaneous injury administration or three administrations (topical) of rMuIL-12 (15 ng, 24 hrs, day 3, and day 5 after injury), accelerated wound healing as compared with a single administration (topical) of vehicle. FIG. 17 shows a graph of would area (% of day 0) vs days post injury for 4 groups: vehicle, 15 ng rMuIL-12 topical 3×/day, 15 ng rMuIL-12 topical 1×/day, and 20 ng rMuIL-12 SC 1×/day. Animals receiving 20 ng rMuIL-12 SC 1×/day showed the fastest wound healing, with animals receiving 15 ng rMuIL-12 topical 3×/day having the next fastest healing rate. FIG. 18A shows a picture of a wound following topical application of vehicle, while FIG. 18B, showing remarkable healing of the wound, depicts the results obtained with SC rMuIL-12.

Figure 19:
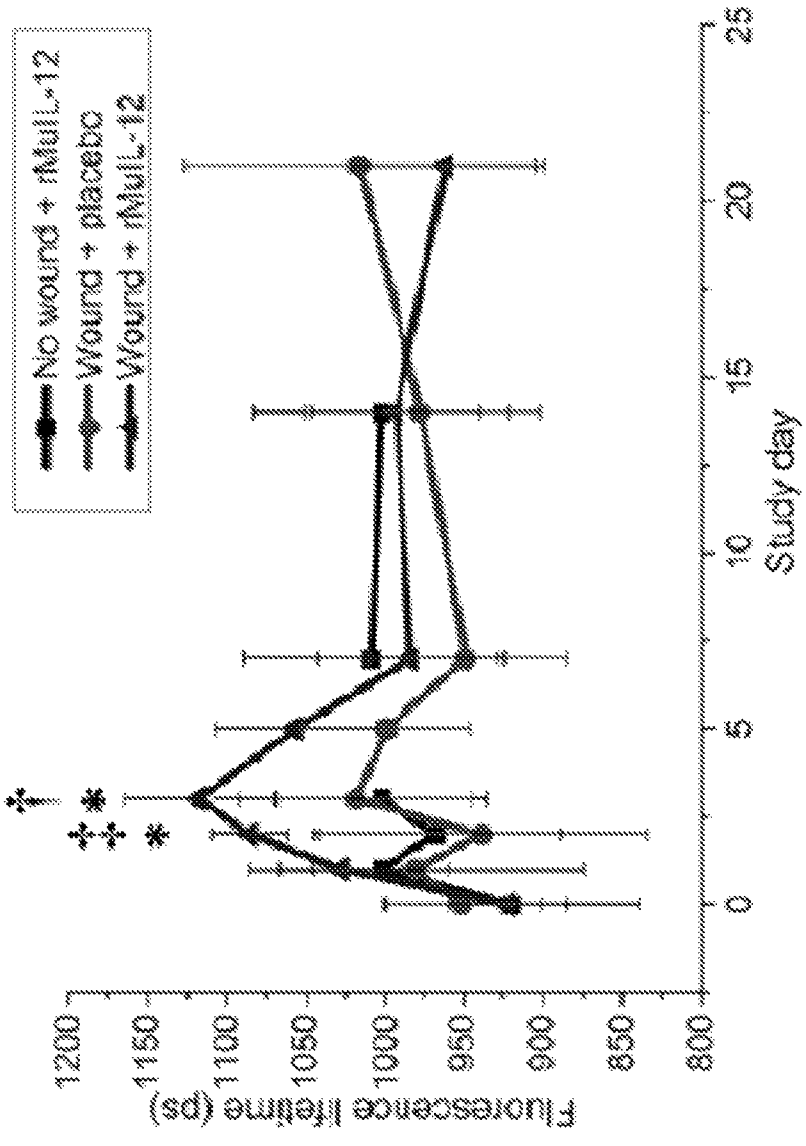
FIG. 19: Shows the dynamics of the metabolic activity in wounded skin during healing using fluorescence lifetime microscopy. The graph of fluorescence lifetime (ps) vs study day, shows the dynamics of the metabolic activity in wounded skin during healing. The SC rMuIL-12+wound group has a significantly longer fluorescence lifetime as compared to the wounded placebo group on day 2 (‡, $p<0.05$). SC rMuIL-12+wound group has a significantly longer fluorescence lifetime compared to the non-wounded group on day 3 (‡, $p<0.05$). Finally, rMuIL-12+wound group has significantly longer fluorescence lifetimes on days 2 and 3 as compared to day 0 (*, $p<0.05$).

It was also found that a single injection of murine NM-IL-12 triggers a significantly more rapid and greater metabolic response in a full-thickness murine excisional wound. FIG. 19, which shows a graph of fluorescence lifetime (ps) vs study day, shows the dynamics of the metabolic activity in wounded skin during healing. (‡) rMuIL-12+wound group has a significantly longer fluorescence lifetime as compared to the wounded placebo group on day 2 ($p<0.05$). (†)rMuIL-12+wound group has a significantly longer fluorescence lifetime compared to the non-wounded group on day 3 ($p<0.05$). Finally, (*)rMuIL-12+wound group has significantly longer fluorescence lifetimes on days 2 and 3 as compared to day 0 ($p<0.05$). See e.g., Li et al., *Biomedical Optics Express,* 6:243477 (2015).

Figure 20:
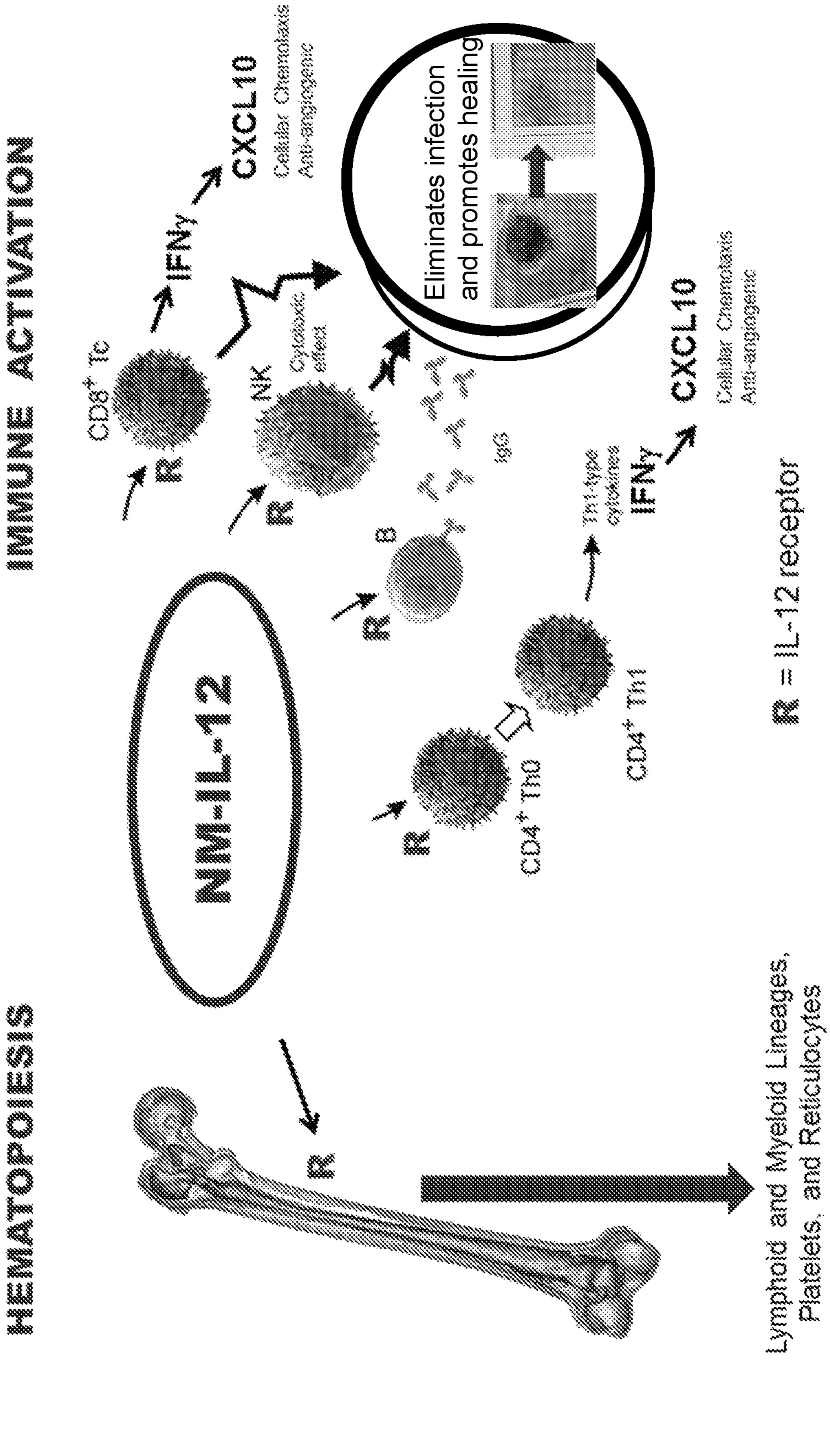
FIG. 20: Graphically depicts how NM-IL-12, as a replacement immunotherapeutic, restores endogenous IL-12's pleiotropic immune and hematopoietic effects to fight infection and heal wounds (adapted from Lasek et al., *Cancer Immunol. Immunother.,* 63:419 (2014).

Currently a Phase 2a, Proof-of-Concept study in patients with open surgical wounds following colostomy takedown is being conducted. In subjects with open surgical wounds following colostomy takedown allowed to heal by secondary intention. The study utilizes a single 12 μg unit SC administered 24-36 hours post-operatively. The secondary endpoint is the median time to greater than 50% surgical stoma site (wound) closure. FIG. 20 graphically depicts how NM-IL-12, as a replacement immunotherapeutic, restores endogenous IL-12's pleiotropic immune and hematopoietic effects to heal wounds (adapted from Lasek et al., *Cancer Immunol. Immunother.,* 63:419 (2014).

Other research supports the analysis and conclusions regarding the usefulness and effectiveness of IL-12 in aiding and accelerating wound healing, in particular for slow healing wounds. See e.g., (1) references detailing that IL-12 has potent anti-infective effects, including "Interleukin-12 in infectious diseases," ('lin. Microbiology Rev., 10(4):611-36 (1997); (ii) references detailing that NM-IL-12 is unique in that it mobilizes all major peripheral blood cells to tissues, including CD34+ bone marrow cells, including "Single low-dose rHuIL-12 safely triggers multilineage hematopoietic and immune-mediated effects," *Exp. Hematology & Oncology,* 3:11 (2014); (iii) references detailing that G-CSF mobilization does not affect infections or wound healing, but shows a reduction in lower extremity surgical interventions in DFU, including "Granulocyte-colony stimulating factors as adjunctive therapy for diabetic foot infections," *Cochrane Database of Systematic Reviews*, Issue 8. Art. No.: CD006810. DOI: 10.1002/14651858.CD006810.pub3 (2013); (iv) references detailing that NM-IL-12 shows potent effects in regenerating bone marrow following lethal radiation exposure, including "Recombinant interleukin-12, but not G-CSF, improves survival in lethally irradiated nonhuman primates in the absence of supportive care," 22 May 2014 in Wiley Online Library (wileyonlinelibrary.com) DOI: 10.1002/ajh.23770; and (v) references detailing that murine IL-12 shows increased metabolic activity and collagen deposition following a full-thickness wound, including "Effect of rIL-12 on murine skin regeneration and cell dynamics using in vivo multimodal microscopy," *Biomedical Optics Express,* 6(11) (November 2015) DOI:10.1364/BOE.6.004277.

C. Age-Related Macular Degeneration

Age-Related Macular Degeneration (AMD), particularly wet AMD, is thought to be brought about by abnormal growth of blood vessels (angiogenesis) in aging eyes. The current approved products in wet AMD are anti-VEGF antibodies (Lucentis, Eyelea). These drugs have been shown to have limited efficacy and leave one third of the treated population with poor outcomes and declining sight. Follow-on wet AMD products in development are also targeting a related anti-angiogenic factor, namely PDGF with an anti-PDGF antibody.

Figure 21:
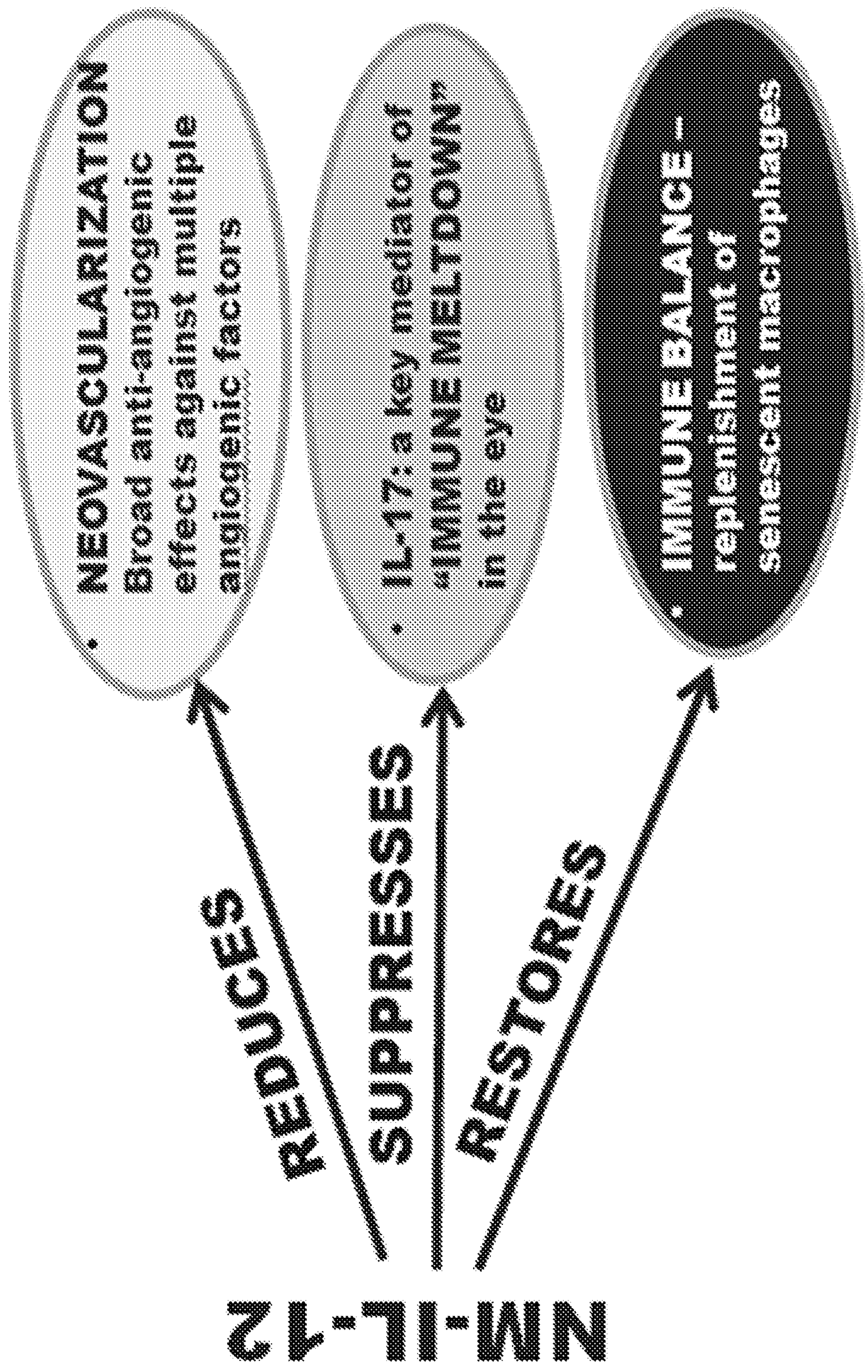
FIG. 21: Graphically depicts how NM-IL-12's pleiotropic effects in AMD are predicted to reverse progression by (i) reducing neovascularization because IL-12 has broad anti-angiogenic effects against multiple angiogenic factors; (ii) suppressing IL-17, which is a key mediator of "immune meltdown" in the eye; and (iii) restoring immune balance by replenishment of senescent macrophages.
Figure 22:
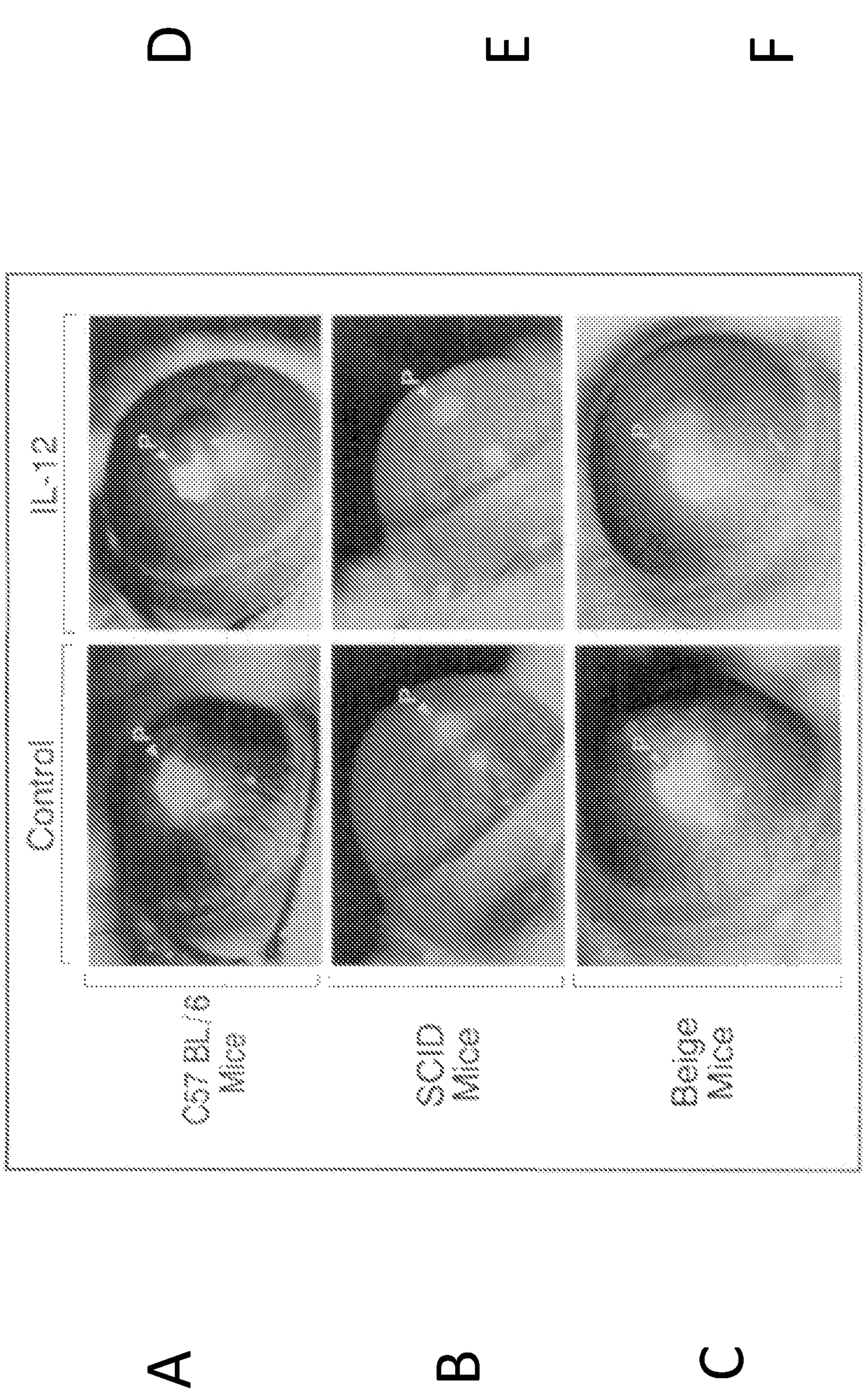
FIG. 22: Shows the effect of recombinant murine IL-12 on basic fibroblast growth factor-induced (pellet P) mouse corneal neovascularization.

IL-12 has potent anti-angiogenic effects shown to be active in reducing angiogenesis in cancer models and in cancer patients (decreasing VEGF and related factors), and in reducing corneal neovascularization (wet AMD) in several model systems. There are also reports that immune dysfunction may be at the core of AMD, with senescent macrophages declining in the production of IL-12. Thus, NM-IL-12 is an attractive new drug that brings additional mechanisms to treat AMD patients either as a single agent or in combination with other drugs. As visually depicted in FIG. 21, NM-IL-12's pleiotropic effects in AMD are predicted to slow or reverse progression by (i) reducing neovascularization because IL-12 has broad anti-angiogenic effects against multiple angiogenic factors; and (ii) restore immune balance by replenishment of senescent macrophages.

In one embodiment of the invention, administration of exogenous IL-12 results in slowing or reversing AMD progression, as compared to that observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In other embodiment, IL-12 can be administered (i) via any route other than intraocular, (ii) via subcutaneous injection, or (iii) via intraocular injection.

There is a significant need for improved treatments for AMD. Specifically, long-term assessment, after ~7 years om ranibizumab therapy, revealed that one third of the patients had poor outcomes. Also compared with baseline, although about half of eyes were stable, one third declined by 15 letters or more. "Seven-Year Outcomes in Ranibizumab-Treated Patients in ANCHOR, MARINA, and HORIZON." *Ophthalmology,* 1e8 (2013). Thus, even at a late stage in the therapeutic course, exudative AMD patients remain at risk for substantial visual decline. Currently approved drugs for wet AMD target angiogenesis via inhibition of VEGF. Clearly, this approach does not help in all patients, leaving a large unmet need for novel drugs. NM-IL-12 offers a new direction and a unique and novel mechanism of action in the treatment of wet AMD, providing anti-angiogenic effects along with pleiotropic immune and hematopoietic effects; these total effects are outside the mechanistic reach of VEGF inhibitors, or any single target therapy.

Figure 23:
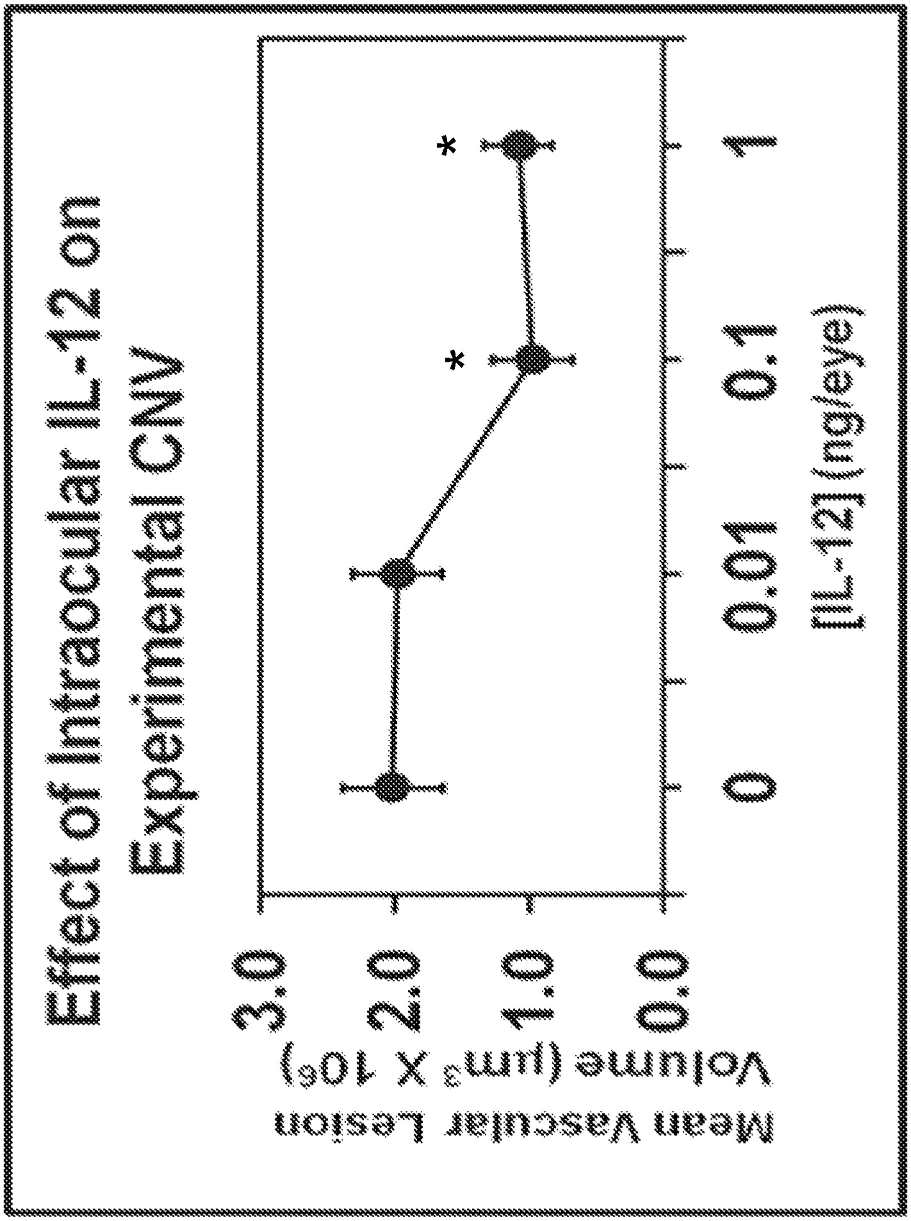
FIG. 23: Shows the dose response for intraocular recombinant murine IL-12 on mean lesion volume in a laser-induced eye injury model (experimental choroidal neovascularization). rMuIL-12 at 0.1 and 1 ng/eye significantly reduced the mean vascular lesion volume (determined from the analysis of fluorescently labelled anti-collagen IV antibody staining). Statistical analysis by Students' t test, *p≤0.02 compared to vehicle alone for both 0.1 and 1 ng/eye rMuIL-12.
Figure 24:
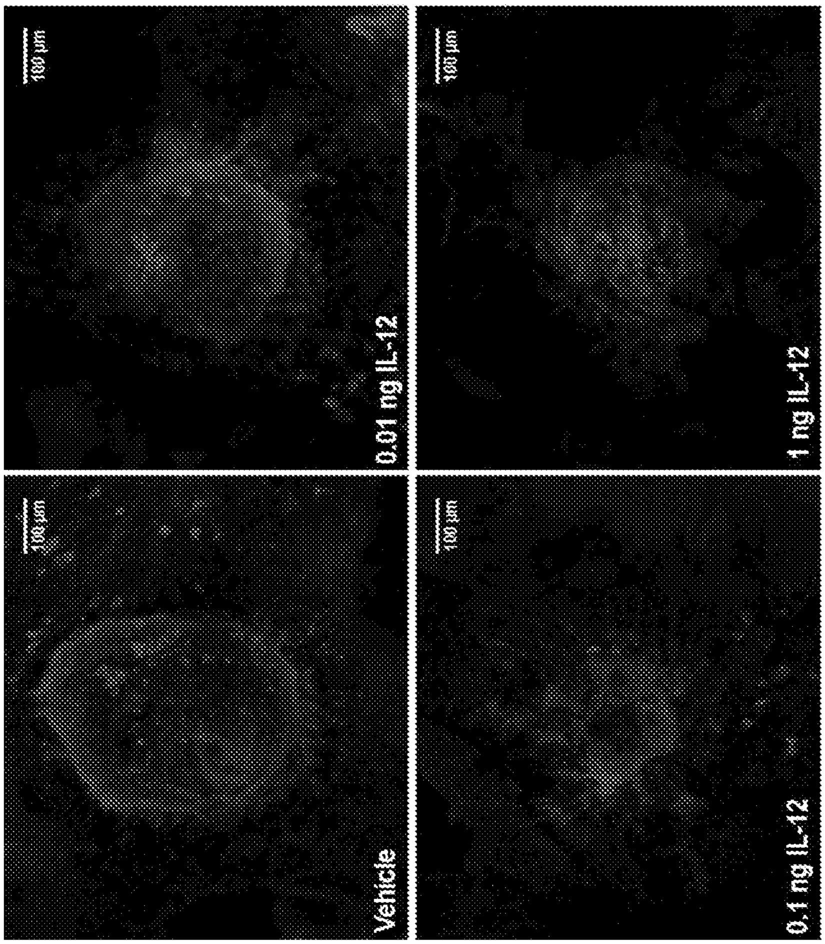
FIG. 24: Shows the visualization of the fluorescent vascular lesions following intraocular administration of vehicle or doses of recombinant murine IL-12, in the laser-induced eye injury model (FIG. 24A=vehicle.

Other data supports the analysis and conclusions presented herein that IL-12 is useful in treating and ameliorating AMD. Specifically, Judah Folkman, who first elucidated the role of angiogenesis in cancer, provided evidence that IL-12 is a potent inhibitor of angiogenesis in a corneal neovascularization model in 1995. See FIG. 22A-F, which show the effect of recombinant murine IL-12 on basic fibroblast growth factor-induced mouse corneal neovascularization. FIGS. 22A-F depict photos which represent corneas of either vehicle-treated (control) C57 BL/6 mice (FIG. 22A), SCID mice (FIG. 22B), and beige mice (FIG. 22C) or 12-treated C57BL/6 mice (FIG. 22D), SCID mice (FIG. 22E), and beige mice (FIG. 22F), 5 days after implantation of the basic fibroblast growth factor pellet (P). There are prominent new vessels in the control corneas, whereas almost no vascular response is seen after treatment with IL-12. *J. of the National Can. Institute,* 87(8) (Apr. 19, 1995). Nearly 20 years later, the present invention shows that murine IL-12 can protect against laser-induced eye injury (experimental choroidal neovascularization) using a single low dose of 0.1 ng per eye. FIG. 23 shows the dose response for murine IL-12 on mean lesion volume. FIGS. 24A-D shows the visualization of lesions at given doses of murine IL-12 (*p<0.02 against 0 ng IL-12 for both 0.1 and 1 ng) (FIG. 24A=vehicle; FIG. 24B=0.1 ng IL-12; FIG. 24C=0.1 ng IL-12; and FIG. 24D=1 ng IL-12).

Figure 25:
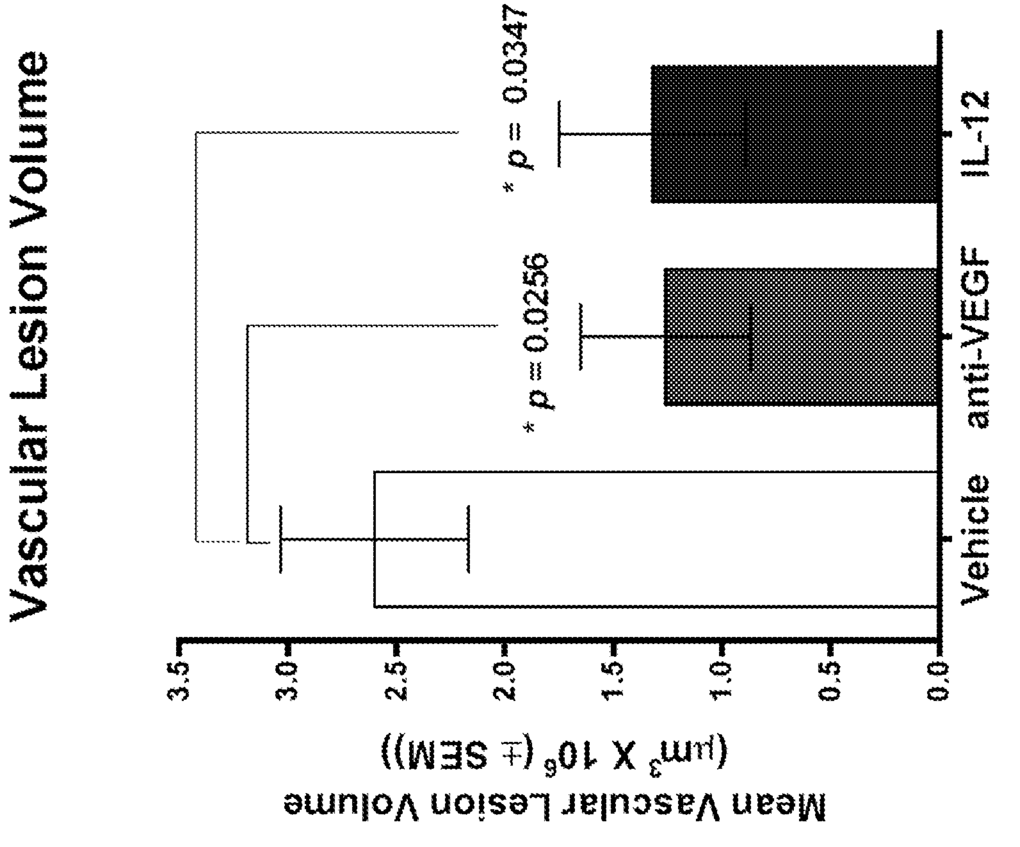
FIG. 25: Shows a graph of mean vascular lesion volume (μm3×106) following treatment with vehicle (about 2.6), anti-VEGF antibody (about 1.7), and rMuIL-12 (about 1.75), in the laser-induced eye injury model. rMuIL-12 and anti-VEGF antibody gave similar significant inhibition of angiogenesis. Statistical analysis by Students' t test, *p≤0.05 compared to vehicle alone.
Figure 26:
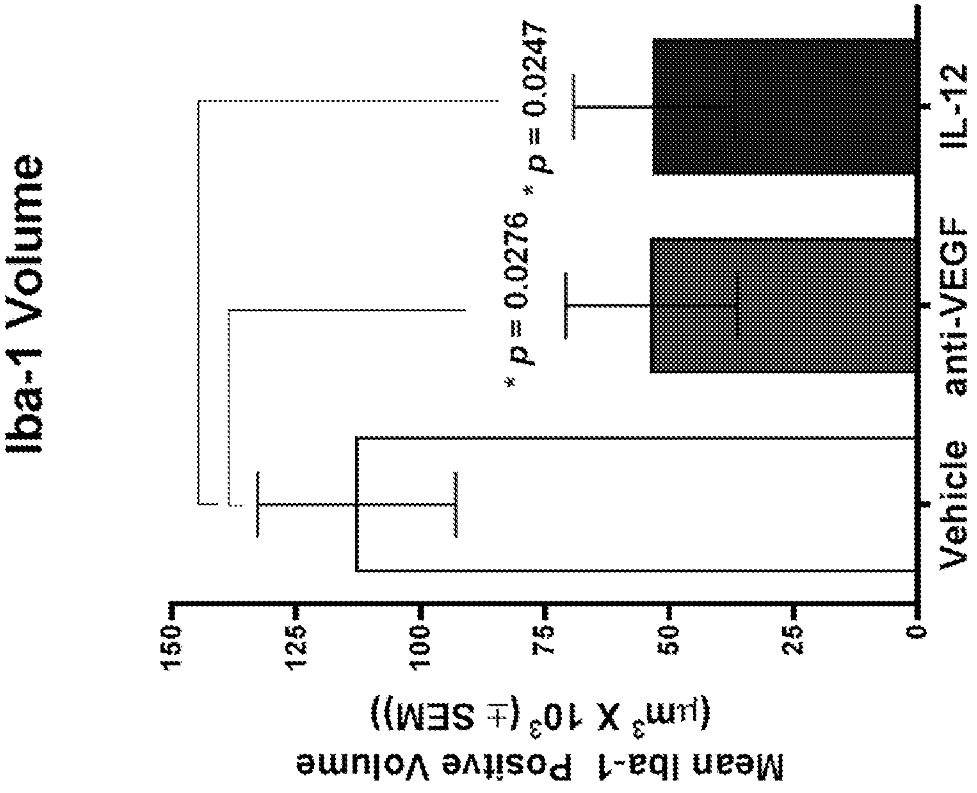
FIG. 26: Shows a graph of mean Iba-1 Positive Volume (μm3×103) following treatment with vehicle (about 112), anti-VEGF (about 60), and IL-12 (about 60), in the laser-induced eye injury model. rMuIL-12 and anti-VEGF antibody gave similar significant inhibition of angiogenesis. Statistical analysis by Students' t test, *p≤0.05 compared to vehicle alone.

The inventors show that murine IL-12 (0.1 ng per eye) can reduce the effects of laser-induced eye damage equal to anti-VEGF (15 mcg per eye) in an experimental choroidal neovascularization murine model. The combination of NM-IL-12 with conventional AMD treatments such as Lucentis® (ranibizumab injection) or Eylea® (aflibercept) is anticipated to provide synergistic effects or at least additive effects. See e.g., FIG. 25, which shows a graph of mean vascular lesion volume ($\mu m^3 \times 10^6$) following treatment with vehicle (about 2.6), anti-VEGF (about 1.7), and IL-12 (about 1.75). See also FIG. 26, which shows a graph of mean Iba-1 Positive Volume ($\mu m^3 \times 10^3$) following treatment with vehicle (about 112), anti-VEGF (about 60), and IL-12 (about 60).

Figure 27:
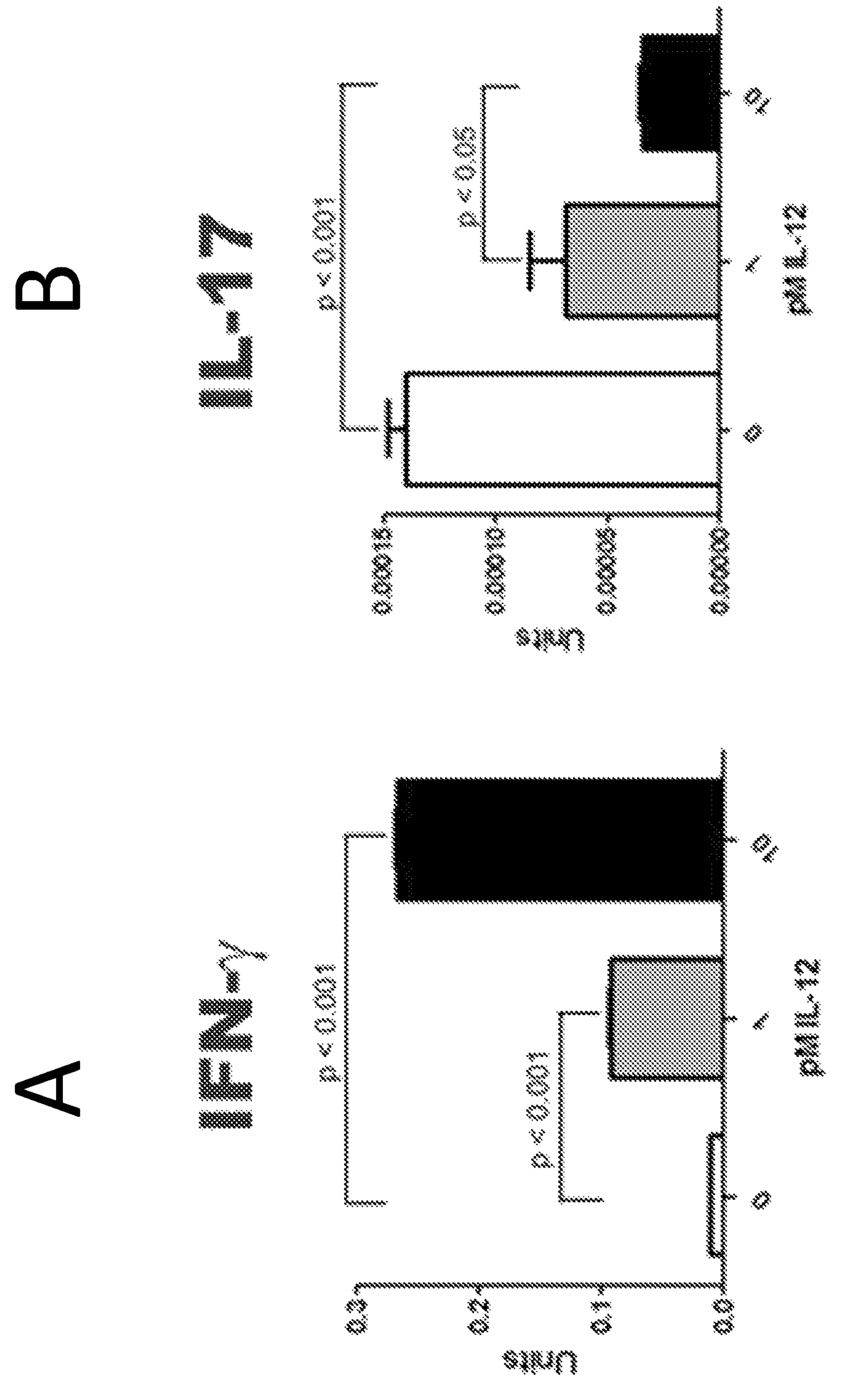
FIG. 27: NM-IL-12 significantly suppresses IL-17 in vitro. NM-IL-12 added to PBMCs is effective in limiting the pathogenic Th17/IL-17 response. In this study, human PBMCs were cultured with 0, 1 and 10 pM of NM-IL-12 for 2 days. Lysates were prepared and probed (PCR) for mRNA for IFN-γ and IL-17. Data are mean±SEM and p values are Student's t test. As predicted the IL-12 treatment is shown to significantly increase the anti-angiogenic IFN-γ (FIG. 27A), and to significantly decrease the destructive IL-17 (FIG. 27B).

NM-IL-12 significantly suppresses IL-17 in vitro. NM-IL-12 added to PBMCs is effective in limiting the pathogenic Th17/IL-17 response. In this study, human PBMCs were cultured with 0, 1 and 10 pM of NM-IL-12 for 2 days. Lysates were prepared and probed (PCR) for mRNA for IFN-γ and IL-17. Data are mean±SEM and p values are Student's t test. As predicted the IL-12 treatment is shown to significantly increase the anti-angiogenic IFN-γ (FIG. 27A), and to significantly decrease the destructive IL-17 (FIG. 27B); these effects are anticipated to decrease angiogenesis and restore immune balance in vivo.

Figure 28:
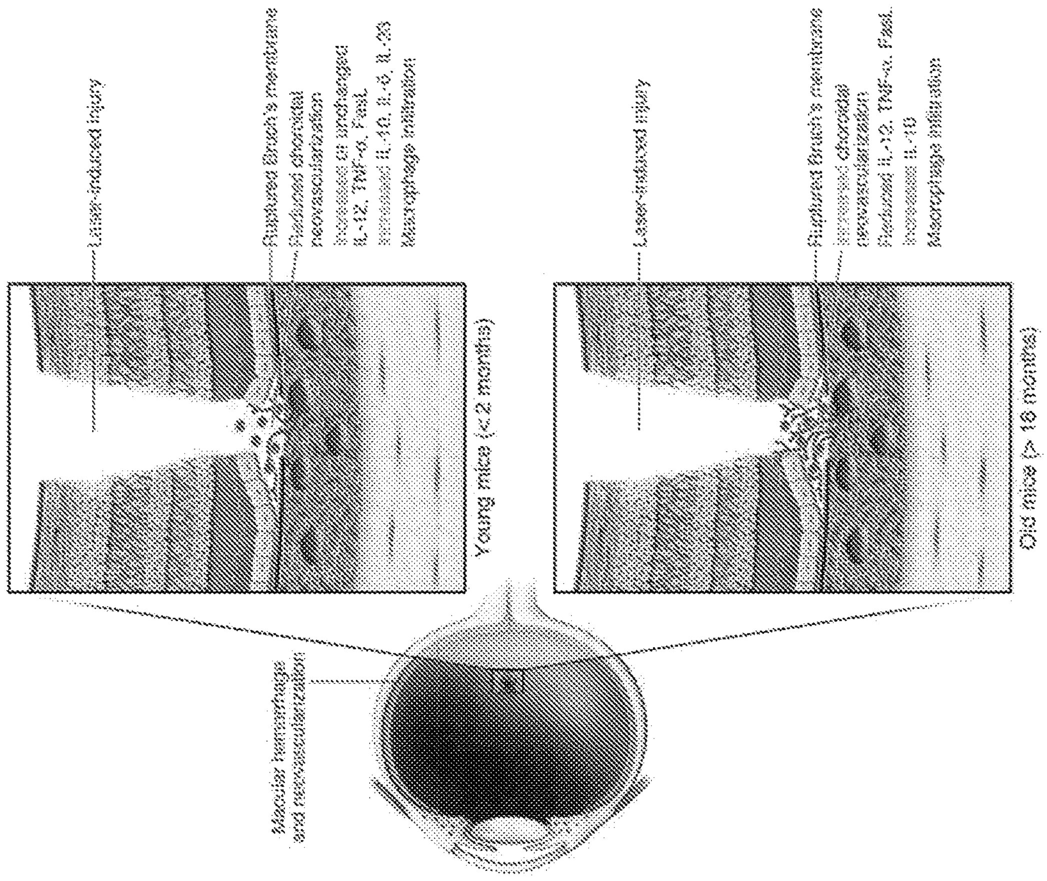
FIG. 28: Shows the role of normal versus senescent macrophages in ocular neovascularization. Following laser-induced injury of the retina, macrophage infiltration occurs in both young (<2 months) and old (>18 months) mice. In the aged mice the reduced IL-12 and increased IL-10 limits the ability to reduce injury-induced neovascularization in the eye.

Thus, IL-12 is a "missing link" in the aged eye; restoration of immune balance by exogenous NM-IL-12 addresses problems encountered with prior art AMD treatments. FIG. 28 shows the role of normal versus senescent macrophages in ocular neovascularization. Following laser-induced injury of the retina, macrophage infiltration occurs in both young (<2 months) and old (>18 months) mice. However, this macrophage infiltration is associated with neovascularization in older mice only. RT-PCR analyses of macrophages isolated from the retinae of older mice revealed lower expression levels of IL-12, TNF-α, FasL and IL-6 than in macrophages in the retinae of younger mice. An increase in IL-10 expression was observed in the retinae of all mice, although baseline levels were higher in old mice. These data suggest that as the mice age, increased IL-10 expression and altered cytokine expression limits the ability of senescent macrophages to regulate injury-induced neovascularization in the eye. As summarized in Table 5 below, NM-IL-12 offers broad & unique mechanistic benefits in AMD as compared to currently marketed products.

TABLE 5

| | NM-IL-12 | Lucentis/Eylea |
|---|---|---|
| Anti-angiogenic (anti-VEGF) | ✓ | ✓ |
| Anti-angiogenic (anti-FGFs) | ✓ | x |
| Anti-angiogenic (anti-PDGF) | ✓ | x |
| Down-regulates IL-17 | ✓ | x |
| Restores immune balance | ✓ | x |
| Regenerates macrophages | ✓ | x |

D. Osteoporosis

Cancer treatments, i.e., radiation, chemotherapy and steroids, can lead to decreased bone density. In addition, other patient populations, such as the elderly and subjects that take certain medications, can suffer from decreased bone density and osteoporosis. The inventors have shown that a single injection of low dose NM-IL-12 can significantly decrease osteoclast levels in monkey bone following high dose total body irradiation (TBI), and that after TBI in mice, the IL-12 receptor was found on osteoblasts in the bone marrow, suggestive of a regenerative effect. IL-12 has been reported to increase osteoblast formation and be a strong inhibitor osteoclast formation, thereby suggesting that IL-12 might be a key regulator of bone formation. However, the effects of aging and life-long exposure to antigens and oxidative stress impairs the physiological counter regulatory immune process that allow for release of IL-12 to inhibit bone resorption. The inventors' data suggest use of NM-IL-12 in patients undergoing treatments for cancer, as well as in patients having a deficiency in bone mass due to aging or other factors.

In one embodiment of the invention, administration of exogenous IL-12 results in reducing bone loss and/or decreasing osteoclast formation, as compared to that observed in the absence of administration of exogenous IL-12, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Figure 29:
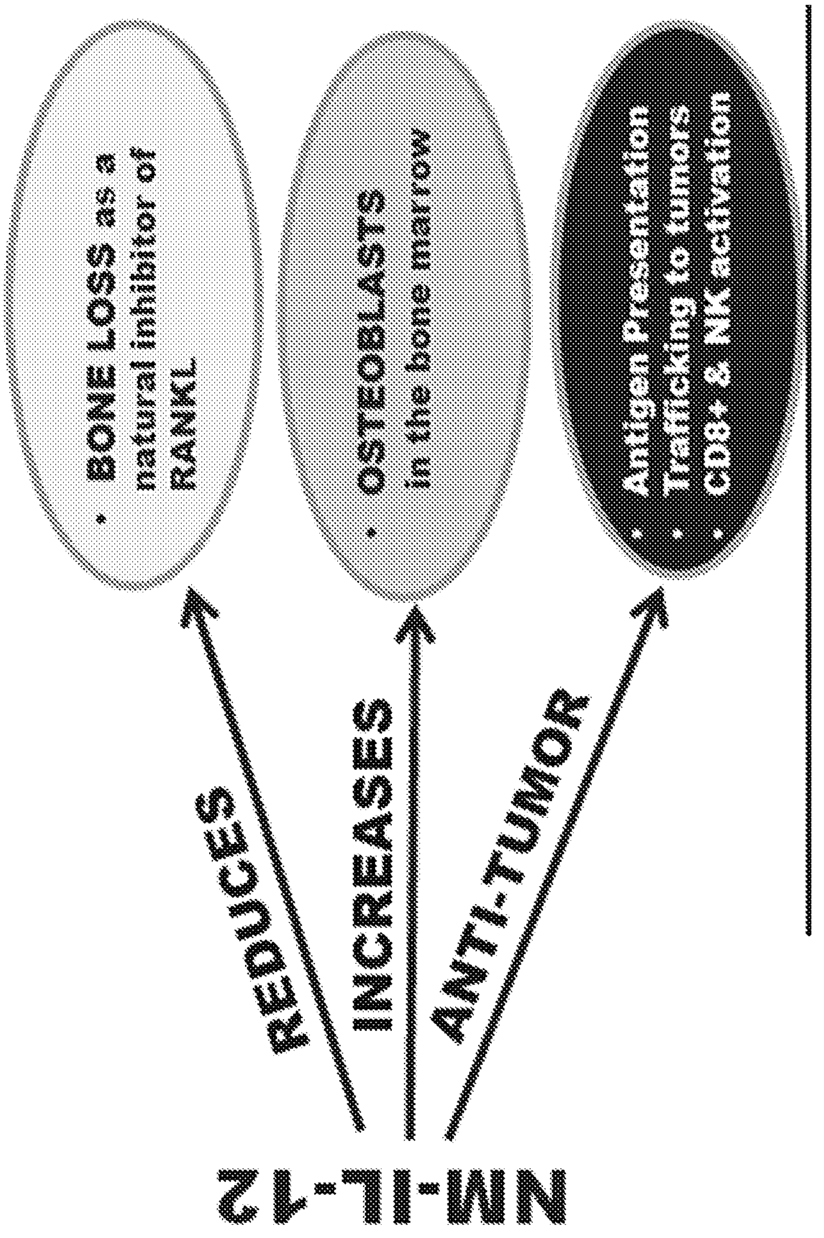
FIG. 29: Graphically depicts how NM-IL-12 reduces bone loss as a natural inhibitor of RANKL, increases osteoblasts in the bone marrow, and has anti-tumor effects by facilitating antigen presentation and enhancing cellular trafficking to tumors, as well as activating CD8+ and NK cells.

As graphically depicted in FIG. 29, NM-IL-12 reduces bone loss as a natural inhibitor of RANKL, increases osteoblasts in the bone marrow, and has anti-tumor effects in antigen presentation and trafficking to tumors, as well as CD8+ and NK activation.

Cancer patients experience higher bone loss rates due cancer treatments, i.e., radiation, chemotherapy and steroids, as well as the underlying disease. NM-IL-12 is predicted to have dual benefits in cancer patients receiving cancer treatments: (1) reduce bone loss and fractures, while (2) providing synergistic anti-tumor mechanisms with the cancer treatment, i.e., radiation or chemotherapy. A clinical endpoint of decreased bone loss in cancer patients receiving radiation to the pelvic region, as a surrogate endpoint for reduced fracture rate, can be eligible for accelerated, conditional approval. The unmet need for a drug that can provide the dual benefits of reduced bone loss with concomitant anti-tumor effects in cancer predicts a relatively short path to market may be available for NM-IL-12.

Figure 30:
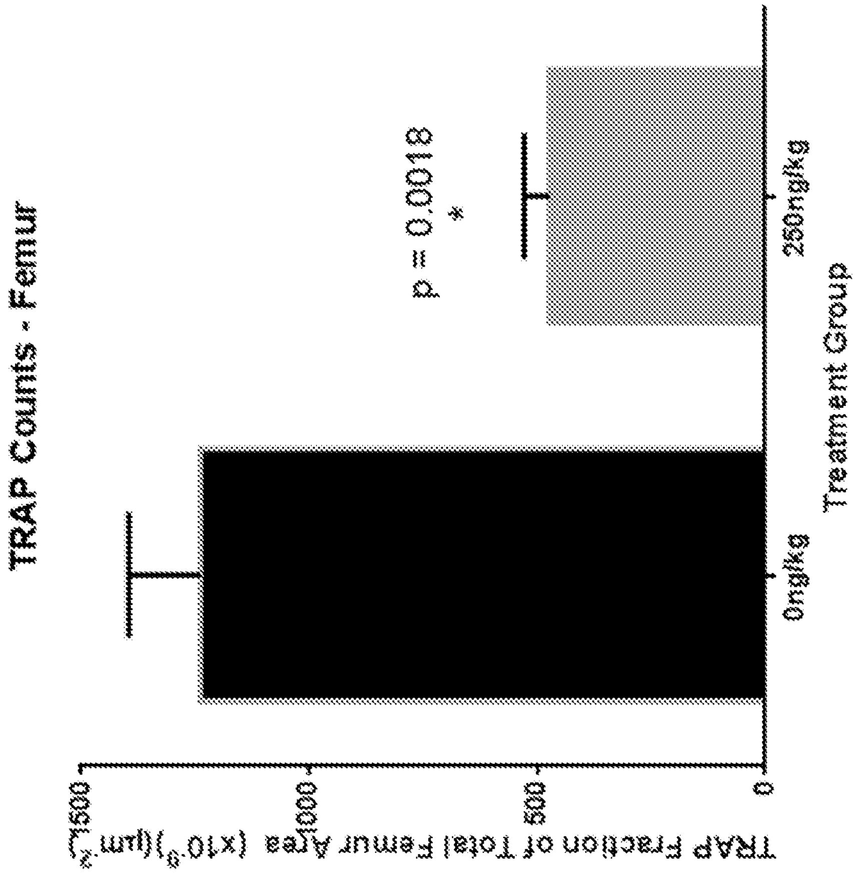
FIG. 30: Shows TRAP Counts—Femur, e.g., TRAP (tartrate resistant acid phosphatase) fraction of total femur area for two treatment groups (0 ng/kg and 250 NM-IL-12 ng/kg) in non-human primates. SC administration of NM-IL-12 resulted in significantly decreasing osteoclast formation measured in femur. Statistical analysis by Students' t test, *p≤0.01 compared to vehicle.
Figure 31:
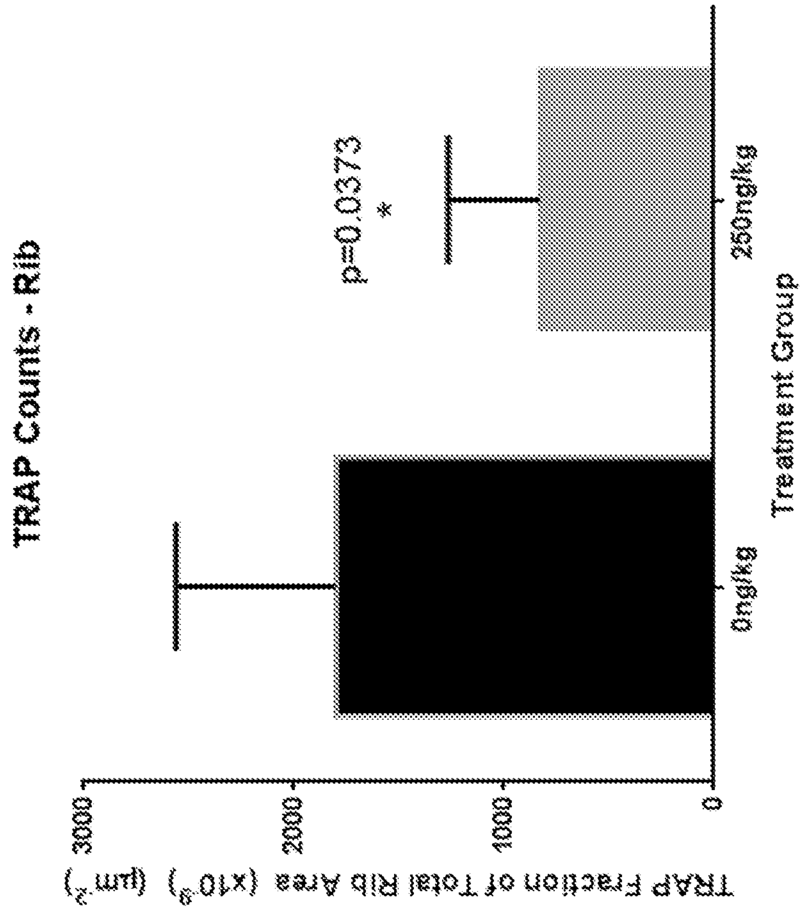
FIG. 31: Similarly.

Radiation induces osteoclast formation. A single SQ injection of low dose NM-IL-12 decreases osteoclast formation following bone damaging doses of TBI in monkeys, as compared to controls. See FIG. 30, which shows TRAP Counts—Femur, e.g., TRAP (tartrate resistant acid phosphatase) fraction of total femur area for two treatment groups (0 ng/kg and 250 IL-12 ng/kg). TRAP is an enzyme marker of osteoclasts. Similarly, FIG. 31 shows TRAP Counts—Rib, e.g., TRAP fraction of total rib area for two treatment groups (0 ng/kg and 250 IL-12 ng/kg). Administration of IL-12 resulted in significantly decreasing osteoclast formation measured in both femur and rib (FIGS. 30 and 31).

Figure 32:
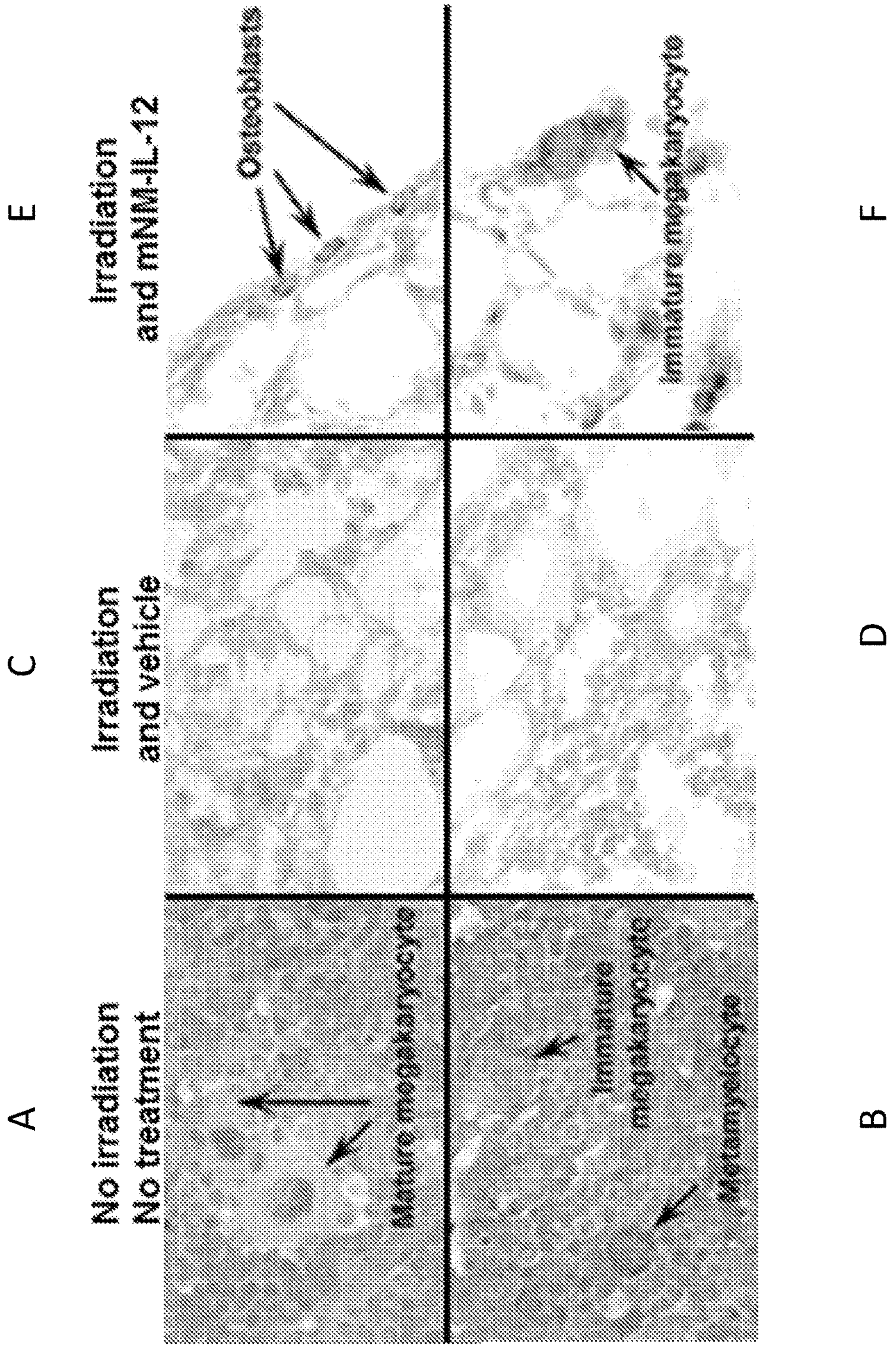
FIG. 32: Murine IL-12 Promotes Hematopoietic Recovery in Irradiated Mice. Representative sections of femoral bone marrow from non-irradiated, untreated mice that were stained for IL-12Rβ2 are shown in FIGS. 32A and 32B. Animals were subjected to TBI (8.0 Gy) and subsequently received vehicle (FIGS. 32C and 32D) or rMuIL-12 (20 ng/mouse) subcutaneously (FIG. 32E and FIG. 32F) at the indicated times post irradiation. Femoral bone marrow was immunohistochemically stained for IL-12Rβ2 (orange color) 12 days after irradiation. While bone marrow from mice treated with vehicle (FIGS. 32C and D) lacked IL-12Rβ2-expressing cells and showed no signs of hematopoietic regeneration, mice treated with rMuIL-12 (FIGS. 32E and F) showed hematopoietic reconstitution and the presence of IL-12Rβ2-expressing megakaryocytes, myeloid progenitors, and osteoblasts. Magnification=100×.

The IL-12Rbeta2 is found on normal murine osteoblasts in the bone marrow and the receptor is present following lethal radiation; however, the receptor is absent in control mice receiving radiation, suggesting that following radiation, NM-IL-12 can activate/proliferate osteoblasts via its receptor. See e.g., FIG. 32, which shows representative sections of femoral bone marrow stained for IL-12Rbeta2. FIG. 32 shows that mNM-IL-12 promotes hematopoietic recovery in irradiated mice. Specifically, FIGS. 32A and B shows normal femoral bone sections with no irradiation and no treatment, with mature and immature megakaryocytes, along with metamyelocytes, visible. FIGS. 32C and 32D show femoral bone sections following irradiation and treatment with vehicle. Finally, FIGS. 32E and 32F show femoral bone sections following irradiation and treatment with mNM-IL-2. Osteoblasts are clearly visible in FIG. 32E. With irradiated mice, mNM-IL-12 gave hematopoietic reconstitution and the presence of IL-12Rbeta2+ve megakaryocytes, progenitors and osteoblasts.

Figure 33:
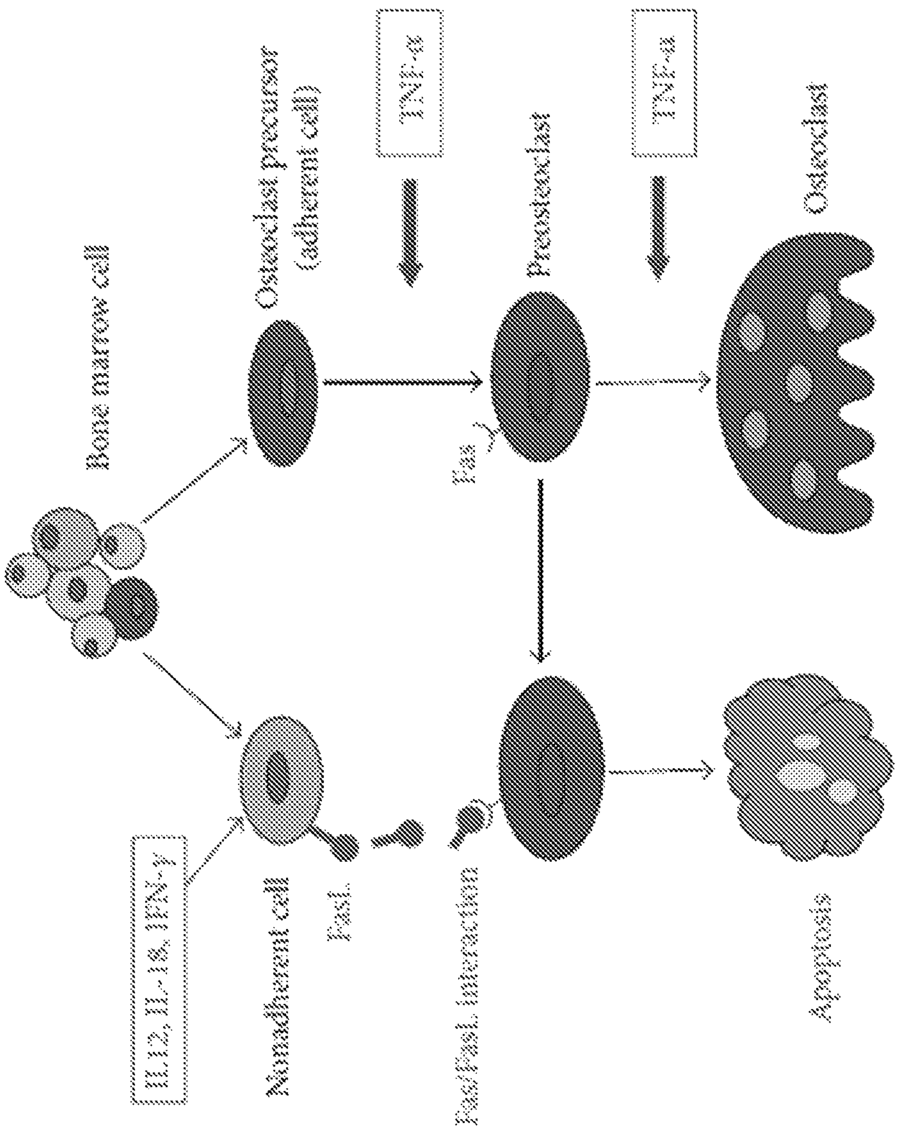
FIG. 33: Visually depicts the mechanism of IL-12, IFN-gamma and IL-18-induced osteoclast apoptosis in bone marrow, thereby reducing bone loss.
Figure 34:
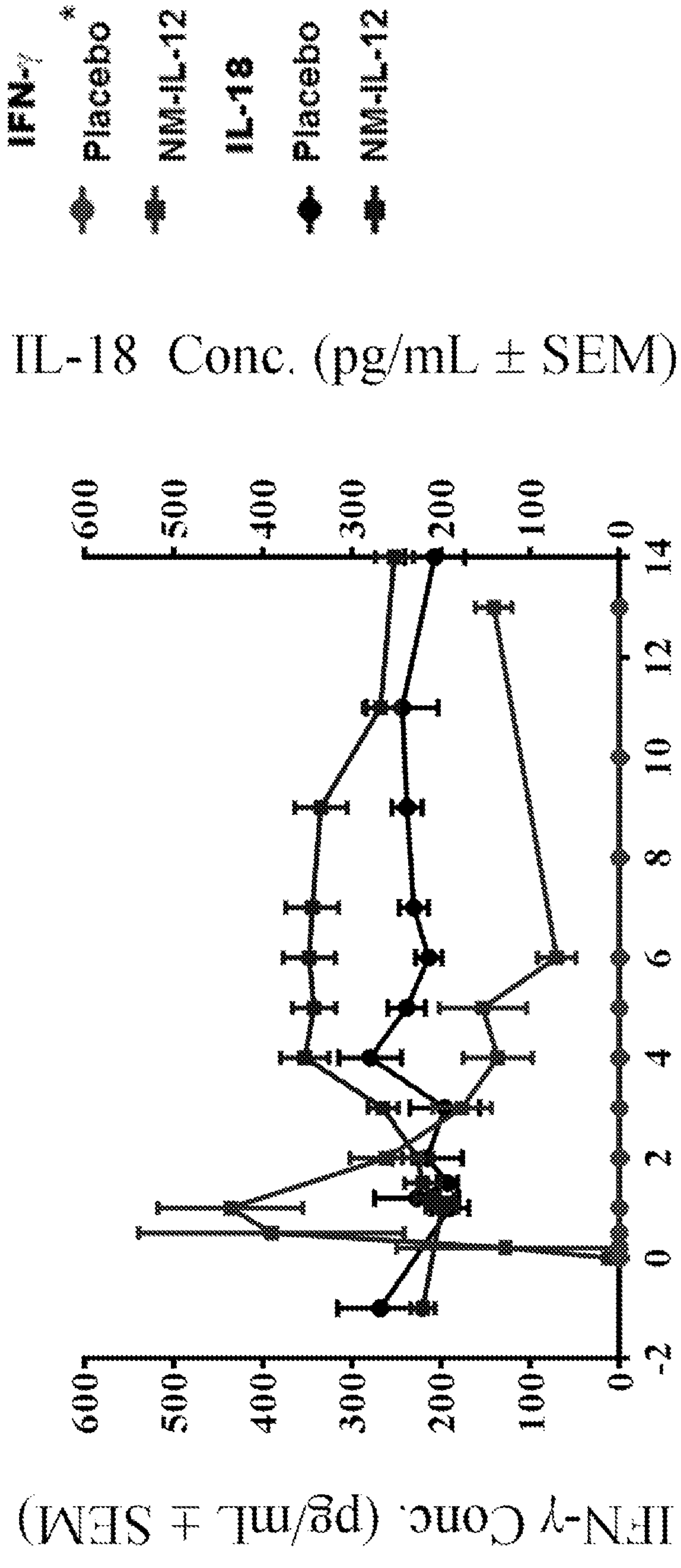
FIG. 34: Shows a graph of the circulating levels of both IFN-gamma and IL-18 vs time, following the SC administration of NM_IL-12 or placebo to healthy human subjects. IL-12 and its induced downstream factors, IFN-gamma and IL-12, are natural inhibitors of RANKL, thereby reducing bone loss. * circulating levels of IFN-gamma in placebo treated subjects were below the limit of quantitation.

IL-12 and its induced downstream factors, IFN-gamma and IL-18, are natural inhibitors of RANKL. FIG. 33 visually depicts the mechanism of IL-12, IFNgamma and IL-18-induced osteoclast apoptosis in bone marrow. A single, SQ injection of NM-IL-12 (12 mg) in healthy humans can induce both INF-gamma and IL-18, thus only IL-12 is needed to inhibit RANKL. See FIG. 34, which shows a graph of IFN-gamma vs time for the following treatment groups: placebo and NM-IL-12, and IL-12 vs time for the same treatment groups. Thus, as summarized in Table 6, NM-IL-12 uniquely offers the dual benefits of bone preservation with concomitant anti-tumor effects in cancer patients. Also in a subject that is not undergoing cancer treatments, IL-12 can be given to prevent or reduce bone loss in those who are in early to late stages of osteoporosis.

TABLE 6

| | NM-IL-12 | Denosumab |
|---|---|---|
| Inhibition of RANKL | ✓ | ✓ |
| Inhibition of Osteoclasts | ✓ | ✓ |
| Proliferation of Osteoblasts | ✓ | x |
| Anti-Tumor Effects: | | |
| Tumor Antigen Presentation | ✓ | x |
| Lymphocyte Migration | ✓ | x |
| Cytotoxicity of NK cells | ✓ | x |
| Cytotoxicity of CD8+/TILs | ✓ | x |
| Anti-angiogenic | ✓ | x |

II. NM-IL-12

NM-IL-12 (also known as HemaMax™ (rHuIL-12)) is a heterodimeric protein consisting of two subunits linked by disulfide bonds. The two subunits are an A and B subunit referred to as p35 and p40, respectively. Heterodimeric IL-12 contains 503 amino acids. The protein can be produced by the recombinant protein production technology in Chines Hamster Ovary (CHO) cells with a total molecular weight of about 75.0 kDa and, like endogenous IL-12, is a glycoprotein in its final form. The glycosylation pattern of NM-IL-12 is different from endogenous IL-12. NM-IL-12 potently elicits the pharmacodynamic response (interferon-γ [IFN-γ]) in human immune cells in vitro and in non-human primates (rhesus monkeys) both in vitro and in vivo. Table 7 provides Investigational product dosage/administration of NM-IL-12.

TABLE 7

| | |
|---|---|
| Product Name | NM-IL-12 |
| Formulation description | The NM-IL-12 (rHuIL-12) Drug Product vial contains 0.65 mL of 20 μg/mL rHuIL-12 protein in 10 mM sodium phosphate, 150 mM sodium chloride, pH 6.0 with 0.1% (w/v) Poloxamer 188 (withdrawal volume of 0.50 mL). |
| Dosage form | Vials |
| Unit dose strength(s)/ dosage levels | 20 μg/mL in 2 mL clear vials |
| Physical description | Solution is clear and colorless |
| Route/duration | Subcutaneously |

NM-IL-12 (rHuIL-12)): NM-IL-12 has demonstrated excellent blood cell recovery, including platelet recovery, recovery following myelosuppressive or myeloablative therapies in murine models, as well as in a non-human primate (NHP) model following myeloablative treatment. In fact, in a proof-of-concept, lethal radiation NHP study, 80% of vehicle-treated monkeys required a platelet transfusion, whereas only 25% of NM-IL-12-treated monkey required a platelet transfusion ($p<0.007$, chi square analysis). NM-IL-12's mechanism of action (MOA) involves regenerating hematopoiesis at the level of hematopoietic stem cells (HSC). In support of this MOA, Neumedicines has found the IL-12 receptor on several key subpopulations of human HSC, as it is co-expressed along with known stem cell markers, such as CD34, c-Kit and KDR.

There is no overlap between HemaMax's mechanism of action and that of the well-known hematopoeitic growth factors. HemaMax's mechanism of action involves activation of hematopoietic stem cells upstream of the activity of other hematopoietic factors. Consequently, HemaMax can replenish and regenerate the hematopoietic and immune systems following ablation, whereas these downstream acting factors cannot, as they target precursor cells to yield a single blood cell type. Via this early-acting (upstream) mechanism, HemaMax's activation of primitive hematopoietic stem cells can restore all major blood cell types.

Figure 14:
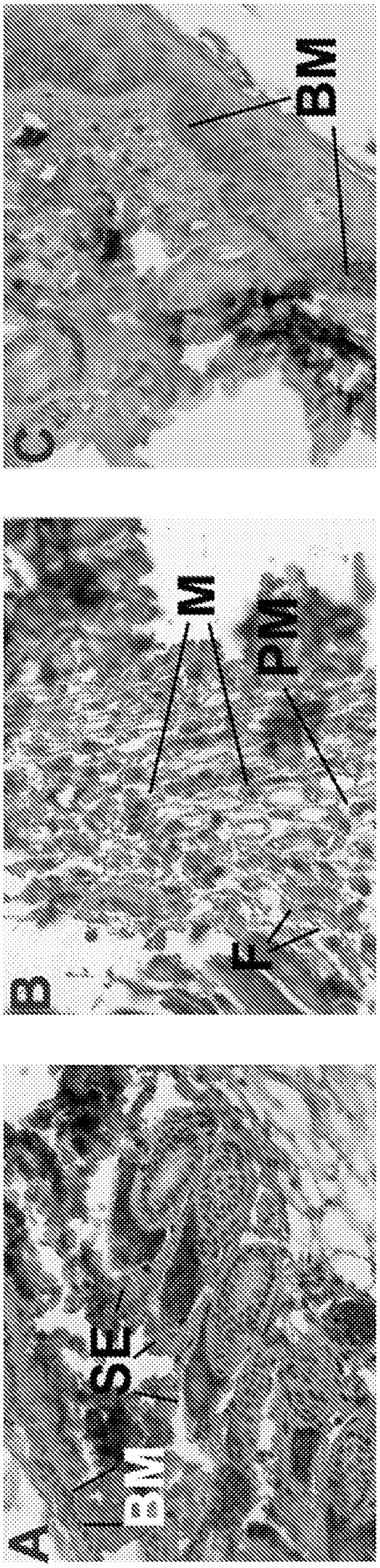
FIG. 14: A previously unidentified role for IL-12 in the stimulation of wound healing is demonstrated in normal FIG. 14A and wounded, irradiated skin tissue (FIGS. 14B and 14C). In irradiated skin, the IL-12Rbeta2 receptor is found to be highly expressed on progenitor cells in the basement membrane (BM) of the dermis and in sebaceous (SE) glands underlying hair follicles.

The unique IL-12 receptor is on progenitor and stem cells of the bone marrow, and is also on mature immune effector cells, such as CD8+, CD4+, NK, and B cells and other cells such as eosinophils. This unique receptor is also on the cells of many tissues, and will be present upon damage of the tissues and organs, such as what was observed in the wound healing context as depicted in FIG. 14. The role of the unique IL-12 receptor interacting with exogenous IL-12 is at the core of the IL-12 as a replacement immunotherapeutic. Overall the upregulation of the IL-12 receptor upon need in the body, such as an following injury or during disease, coupled with exogenous delivery of IL-12 for eradication, repair and regeneration, as needed in the body, is the basis for the present invention In one aspect, the murine counterpart to HemaMax (rMuIL-12) promotes full lineage blood cell recovery including white and red blood cells and platelets in both normal and tumor-bearing mice exposed to sublethal or lethal Total Body Irradiation (TBI). The activity of HemaMax is initiated at the level of primitive cells (hematopoietic and non-hematopoietic stem cells) residing in the bone marrow compartment. Activation of these primitive cells leads to regeneration of the bone marrow compartment following myeloablation or myelosuppression caused by radiation or chemotherapy.

"Interleukin-12 (IL-12)" refers to IL-12 molecule that yields at least one of the hematopoietic properties disclosed herein, including native IL-12 molecules, variant 11-12 molecules and covalently modified IL-12 molecules, now known or to be developed in the future, produced in any manner known in the art now or to be developed in the future.

The IL-12 molecule may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 80%, 85%, or 90%, including, for example, at least about 95%, at least about 98% or at least about 99% of the peptide or dry mass of the preparation.

Generally, the amino acid sequences of the IL-12 molecule used in embodiments of the invention are derived from the specific mammal to be treated by the methods of the invention. Thus, for the sake of illustration, for humans, generally human IL-12, or recombinant human IL-12, would be administered to a human in the methods of the invention, and similarly, for felines, for example, the feline IL-12, or recombinant feline IL-12, would be administered to a feline in the methods of the invention.

Also included in the invention, however, are certain embodiments where the IL-12 molecule does not derive its amino acid sequence from the mammal that is the subject of the therapeutic methods of the invention. For the sake of illustration, human IL-12 or recombinant human IL-12 may be utilized in a feline mammal. Still other embodiments of the invention include IL-12 molecules where the native amino acid sequence of IL-12 is altered from the native sequence, but the IL-12 molecule functions to yield the hematopoietic properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong S R, et al., *Proc. Natl. Acad. Sci., USA.*, 100 (3): 1163-8 (2003)), where the variant IL-12 molecule is produced by a DNA shuffling method. Also included are modified IL-12 molecules are also included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. No. 4,640,835; 4,496,689; 4,301,144; 4,670,417; 4,791,192 or 4,179,337. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Both native sequence IL-12 and amino acid sequence variants of IL-12 may be covalently modified. Also as referred to herein, the IL-12 molecule can be produced by various methods known in the art, including recombinant methods. Other IL-12 variants included in the present disclosure are those where the canonical sequence is post-translationally-modified, for example, glycosylated. In certain embodiments, the IL-12 is expressed in a mammalian expression system or cell line. In one embodiment, the IL-12 is produced by expression in Chinese Hamster Ovary (CHO) cells.

Since it is often difficult to predict in advance the characteristics of a variant IL-12 polypeptide, it will be appreciated that some screening of the recovered variant will be needed to select the optimal variant. A preferred method of assessing a change in the hematological stimulating or enhancing properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

Generally the production of IL-12 stimulates the production of INF-γ, which, in turn, enhances the production of IL-12, thus forming a positive feedback loop. In in vitro systems, it has been reported that IL-12 can synergize with other cytokines (IL-3 and SCF for example) to stimulate the proliferation and differentiation of early hematopoietic progenitors (Jacobsen S E, et al., 1993, J. Exp Med 2: 413-8; Ploemacher R E, et al., 1993, Leukemia 7: 1381-8; Hirao A, et al., 1995, Stem Cells 13: 47-53).

Methods of Administration of NM-IL-12

The present disclosure provides methods of treatment by administration to a subject of one or more physiological dose(s) of IL-12 for a duration to achieve the desired therapeutic effect. The subject is preferably a mammal, including, but not limited to, animals such as cows, pigs, horses, chickens, cats, dogs, etc., and is most preferably human.

A "physiological dose" of NM-IL-12 is a dose that, regardless of the route of administration, yields a range of NM-IL-12 in peripheral blood that is greater than about 1 picogram per ml, but preferably is between about 10 to about 100 picograms per ml measured by a standard ELISA for IL-12 p70. In other embodiments of the invention, the exogenous physiological dose of IL-12 yields an amount of NM-IL-12 in peripheral blood of greater than about 1 picogram per ml, or greater than about 10 pg/ml, and less than about 100, less than about 95, less than about 90, less than 85, less than about 80, less than about 75, less than about 70, less than about 65, less than about 60, less than about 55, less than about 50, less than about 45, less than about 40, less than about 35, less than about 30, less than about 25, less than about 20, less than about 15, less than about 10, or less than about 5 picograms per ml, or any combination thereof, e.g., greater than about 1 pg/ml and less than about 50 pg/ml; or greater than about 1 pg/ml and less than about 15 pg/ml; or greater than about 1 pg/ml and less than about 10 pg/ml; or greater than about 10 pg/ml and less than about 50 pg/ml; or greater than about 10 pg/ml and less than about 20 pg/ml, etc.

Various delivery systems are known and can be used to administer IL-12 in accordance with the methods of the invention, e.g., encapsulation in liposomes, microparticles, microcapsules, recombinant cells capable of expressing IL-12, receptor-mediated endocytosis (see, e.g., Wu and Wu, 1987, J. Biol. Chem. 262:4429-4432), construction of nucleic acid comprising a gene for IL-12 as part of a retroviral or other vector, etc. Methods of introduction include but are not limited to intradermal, intramuscular, intraperitoneal, intravenous, subcutaneous, intranasal, epidural, and oral routes.

IL-12 can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. An example of local delivery is ocular delivery in the example of AMD. In addition, it may be desirable to introduce pharmaceutical compositions comprising IL-12 into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising IL-12 locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

Other modes of IL-12 administration involve delivery in a vesicle, in particular a liposome (see Langer, Science 249:1527-1533 (1990): Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

Still other modes of administration of IL-12 involve delivery in a controlled release system. In certain embodiments, a pump may be used (see Langer, supra; Sefton, CRC Crit. Ref. Biomed. Eng. 14:201 (1987); Buchwald et al., Surgery 88:507 (1980); Saudek et al., *N. Engl. J. Med.* 321:574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley. N.Y. (1984); Ranger and Peppas, J. Macromol. Sci. Rev. Macromol. Chem. 23:61 (1983; see also Levy et al., Science 228:190 (1985); During et al., Ann. Neurol. 25:351 (1989); Howard et al., J. Neurosurg. 71:105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (Science 249:1527-1533 (1990)).

In one aspect, the one or more effective doses of IL-12 are administered topically, subcutaneously, intradermally, intravenously, intraperitoneally, intramuscularly, epidurally, parenterally, intraocularly, intranasally, and/or intracranially.

Forms and Dosages of NM-IL-12

Suitable dosage forms of NM-IL-12 for use in embodiments of the present invention encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of IL-12 polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nanocapsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and gamma ethyl-L-glutamate (Sidman et al, supra), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated IL-12 polypeptides remain in the body for a long time, they may denature or aggregate as a result of exposure to moisture at 37 degree C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release IL-12 containing compositions also include liposomally entrapped polypeptides. Liposomes containing a IL-12 polypeptide are prepared by methods known in the art, such as described in Eppstein et al., Proc. Natl. Acad. Sci. USA 82:3688-3692 (1985); Hwang et al., Proc. Natl. Acad. Sci. USA 77:4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal Wnt polypeptide therapy. Liposomes with enhanced circulation time are disclosed in U.S. Pat. No. 5,013,556.

For the treatment of disease, the appropriate dosage of a IL-12 polypeptide will depend on the type of disease to be treated, as defined above, the severity and course of the disease, previous therapy, the patient's clinical history and response to the IL-12 therapeutic methods disclosed herein, and the discretion of the attending physician. In accordance with the invention, IL-12 is suitably administered to the patient at one time or over a series of treatments.

Weight-based or fixed NM-IL-2 dosing: Depending on the type and severity of the disease, about 10 ng/kg to 2000 ng/kg of IL-12 is an initial candidate dosage for administration to the patient, whether, for example, by one or more separate administrations, or by continuous infusion. Alternatively, a fixed dose of NM-IL-12 can be utilized, such as about 40 μg, about 35 μg, about 30 μg, about 25 μg, about 20 μg, about 19 μg, about 18 μg, about 17 μg, about 16 μg, about 15 μg, about 14 μg, about 13 μg, about 12 μg, about 11 μg, about 10 μg, about 9 μg, about 8 μg, about 7 μg, about 6 μg, about 5 μg, about 4 μg, about 3 μg, about 2 μg, or about 1 μg. Exemplary dosing ranges include but are not limited to (i) greater than about 1 μg and less than about 20 μg; (ii) about 8 μg up to about 15 μg; and (iii) about 10 μg to about 12 μg. An exemplary maintenance dose of NM-IL-12, following initial administration is about 5 μg to about 10 μg, although any dosage described herein can be used for an initial or maintenance dose. Humans can safely tolerate a repeated dosages of about 500 ng/kg, but single dosages of up to about 200 ng/kg should not produce toxic side effects. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

Another aspect of the invention is directed to a method of identifying subjects in need of exogenous IL-12 as a replacement immunotherapeutic. Subjects who have an identified need for either eradication, repair or regeneration of cells, tissues or organs in the body are suitable to receive exogenous IL-12 as described herein. However, subjects in need have baseline levels of IL-12 expression of less than about 5 pg/ml, or less than about 3 pg/ml, or less than about 1 pg/ml. Generally subjects in need have baseline levels that are below the limit of detection using a validated assay, as described herein, for the detection of IL-12 p70. Thus, the present invention identified specific patient populations that benefit from the methods described herein.

In one aspect of the invention, methods of treatment comprise using two physiological dose levels of IL-12, which can be different or the same, for (i) a treatment dose of IL-12 and a (ii) maintenance dose of IL-12. In one embodiment, the treatment dose of IL-12 is greater than about 1 μg and less than about 20 μg, although any IL-12 dose described herein can be used as a treatment IL-12 dose. In another embodiment, the maintenance dose of IL-12 is greater than about 1 μg and less than about 10 μg, although any IL-12 dose described herein can be used as a maintenance IL-12 dose. In an exemplary embodiment, the treatment doses of IL-12 can be given periodically at the initiation of administration of exogenous IL-12, such as about once a week, about every 2 weeks, about every 3 weeks, about every 4 weeks, about every 5 weeks, or about every 6 weeks. In an exemplary embodiment, the maintenance doses of IL-12 can be given following completion of the initial administration period, and are given at frequencies such as about every 1 month, about every 2 months, about every 3 months, about every 4 months, about every 5 months, or about every 6 months.

In another aspect of the invention, the exogenous physiological dose of IL-12 administered to a subject in need yields a range of NM-IL-12 in peripheral blood that is greater than about 1 picogram per ml and less than about 200 picograms per ml, as measured by a standard ELISA for IL-12 p70. It is noteworthy that levels beyond 200 pg/ml of IL-12 p70 in peripheral blood may not be beneficial. In other embodiments, the range of NM-IL-12 in peripheral blood can be greater than about 1 pg/ml and less than about 200 pg/ml, less than about 175 pg/ml, less than about 150 pg/ml, less than about 125 pg/ml, less than about 100 pg/ml, less than about 75 pg/ml, less than about 50 pg/ml, less than about 25 pg/ml, less than about 15 pg/ml, or less than about 10 pg/ml. In yet another aspect of the invention, following administration of IL-12, in addition to the measurable levels of IL-12 in the peripheral blood of the subject, there will also be a concomitant increase in IFN-gamma in peripheral blood; and/or the measurable levels of IL-12 in the peripheral blood of the subject also show an increase in IFN-g in peripheral blood, wherein the concomitant levels of IFN-gamma following IL-12 dosing are in a range of about 20 pg/ml to about 1000 pg/ml. In other aspects, the range of IFN-gamma following IL-12 dosing can be about 1000 pg/ml or less, about 900 pg/ml or less, about 800 pg/ml or less, about 700 pg/ml or less, about 600 pg/ml or less, about 500 pg/ml or less, about 400 pg/ml or less, about 300 pg/ml or less, about 200 pg/ml or less, about 100 pg/ml or less, about 75 pg/ml or less, or about 50 pg/ml or less.

Another aspect of the invention is that concomitant levels of both IL-12p70 and IFN-gamma in peripheral blood can be considered markers of efficacy as a replacement immunotherapeutic. If the levels of either of the factors decreases substantially from the initial levels in the blood following dosing with NM-IL-12, then the replacement efficacy might be less therapeutic. In this case, subsequent dose of NM-IL-12 can be reduced.

Table 8 below shows ranges of IL-12 amounts observed in patient's blood following a single IL-12 dose of 12 μg. (This was part of a pharmacokinetic/pharmacodynamics analysis conducted in healthy subjects.)

TABLE 8

| | Pharmacokenetic | | | | | | | | Pharmacodynamic IFn-γ Concentration in pg/mL | |
|---|---|---|---|---|---|---|---|---|---|---|
| | HemaMax Concentration in pg/mL | | | | | | | | | Phase 2 Study |
| | Phase 1b Study 2012-002 | | | Phase 2 Study 2014-003 | | | | | Phase 1b Study | 2014-003 |
| | All Subjects | Age: 40+ | Age: 50+ | All Subjects* | Age: 40+ | Age: 50+ | Age: 60+ | Age: 70+ | 2012-002 All | All Subjects* |
| N | 32 | 1 | 0 | 83 | 48 | 26 | 11 | 2 | 28 | 83 |
| Mean | 57.67 | 54.7 | 0 | 18.92 | 16.52 | 15.33 | 14.21 | 15.50 | 722.16 | 327.00 |
| Min | 9.53 | 54.7 | 0 | 3.84 | 4.27 | 4.27 | 5.15 | 7.60 | 120.20 | 24.50 |
| Max | 246.60 | 54.7 | 0 | 73.60 | 73.60 | 73.60 | 26.70 | 23.40 | 4992 | 1050 |
| No. of Subjects with PK ≥ 100 pg/mL | 5 | 0 | 0 | 0 | 0 | 0 | 0 | 0 | | |

*Subject 1186 appears to have received an IV dose of HemaMax and was excluded.

Any conventional assay can be used to determine the concentration of IL-12 in human plasma. As examples, and not intended to be limiting, the concentration of IL-12 (e.g., NM-IL-12), in human plasma can be deterred by Enzyme Linked Immunosorbent Assay (ELISA) or by Electrochemiluminescence Immunoassay (MSD). ELISA: This method utilizes a quantitative sandwich enzyme linked immunosorbent assay (ELISA) to measure the concentration of NM-IL-12 in Human K2 EDTA plasma. Standards, controls and test samples containing NM-IL-12 are incubated with a 96 well plate that has been pre-coated with IL-12 capture antibody. After incubation, unbound material is then washed away, and NM-IL-12 is detected with Human IL-12 Detection Antibody Conjugate. After incubation, unbound material is then washed away, and a substrate solution is added to the wells. Finally, an amplifier solution is added to all the wells and color develops in proportion to the amount of NM-IL-12 bound in the initial step. The color development is stopped and the intensity of the color is measured at 490 nm with a wavelength correction set to 650 nm. MSD: In an exemplary assay, fifty microliters of standards and validation samples were added to the appropriate wells on Meso Scale Discovery V-PLEX Human IL-12p70 plates. The plates were covered with a lid and incubated at room temperature for approximately 2 hours on a plate shaker (setting 2-4). The plates were then washed three times with approximately 300 μL per well of MSD Wash Buffer. Twenty-five microliters of detection antibody were added to the plates. The plates were covered with a lid and incubated at room temperature for approximately 2 hours on a plate shaker (setting 2-4). After incubation with the detection antibody, the plates were washed three times with approximately 300 μL per well of MSD Wash Buffer, and 2× Read Buffer T will be dispensed into each well of the plates. The plates were read immediately on a Sector Imager 6000 (Meso Scale Discovery) plate reader. The standard curve was generated using a 4-parameter logistic curve fit of log 10-transformed data (Gen5 Secure software, BioTek Instruments).

Further any conventional assay can be used in the methods of the invention to measure levels of IFN-gamma. An example is as follows: IFN-γ Detection by Electrochemiluminescence Immunoassay (MSD). Fifty microliters of standards and human plasma samples were added to the appropriate wells on Meso Scale Discovery Proinflammatory Panel 1 (human) plates. The plates were covered with a lid and incubated at room temperature for approximately 2 hours on a plate shaker (setting 2-4). The plates were then washed three 4826-8902-1259.1 times with approximately 300 μL per well of MSD Wash Buffer. Twenty-five microliters of SULFO-TAG Anti-hu-IFN-γ Antibody detection antibody were added to the plates. The plates were covered with a lid and incubated at room temperature for approximately 2 hours on a plate shaker (setting 2-4). After incubation with the detection antibody, the plates were washed three times with approximately 300 μL per well of MSD Wash Buffer, and 2× Read Buffer T will be dispensed into each well of the plates. The plates were read immediately on a Sector Imager 6000 (Meso Scale Discovery) plate reader. The standard curve was generated using a 4-parameter logistic curve fit of log 10-transformed data (Gen5 Secure software, BioTek Instruments).

IL-12 may be administered along with other cytokines, either by direct co-administration or sequential administration. When one or more cytokines are co-administered with IL-12, lesser doses of IL-12 may be employed. Suitable doses of other cytokines, i.e. other than IL-12, are from about 1 μg/kg to about 15 mg/kg of cytokine. For example, the dose may be the same as that for other cytokines such as G-CSF, GM-CSF and EPO. The other cytokine(s) may be administered prior to, simultaneously with, or following administration of IL-12. The cytokine(s) and IL-12 may be combined to form a pharmaceutically composition for simultaneous administration to the mammal. In certain embodiments, the amounts of IL-12 and cytokine are such that a synergistic repopulation of blood cells (or synergistic increase in proliferation and/or differentiation of hematopoietic cells) occurs in the mammal upon administration of IL-12 and other cytokine thereto. In other words, the coordinated action of the two or more agents (i.e. the IL-12 and one or more cytokine(s)) with respect to repopulation of blood cells (or proliferation/differentiation of hematopoietic cells) is greater than the sum of the individual effects of these molecules.

Therapeutic formulations of IL-12 are prepared for storage by mixing IL-12 having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or non-ionic surfactants such as Tween®, Pluronics™ or polyethylene glycol (PEG).

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers include but are not limited to histidine-buffers, citrate-buffers, succinate-buffers, acetate-buffers, phosphate-buffers, arginine-buffers or mixtures thereof. The abovementioned buffers are generally used in an amount of about 1 mM to about 100 mM, of about 5 mM to about 50 mM and of about 10-20 mM. The pH of the buffered solution can be at least 4.0, at least 4.5, at least 5.0, at least 5.5 or at least 6.0. The pH of the buffered solution can be less than 7.5, less than 7.0, or less than 6.5. The pH of the buffered solution can be about 4.0 to about 7.5, about 5.5 to about 7.5, about 5.0 to about 6.5, and about 5.5 to about 6.5 with an acid or a base known in the art, e.g. hydrochloric acid, acetic acid, phosphoric acid, sulfuric acid and citric acid, sodium hydroxide and potassium hydroxide. As used herein when describing pH, "about" means plus or minus 0.2 pH units.

As used herein, the term "surfactant" can include a pharmaceutically acceptable excipient which is used to protect protein formulations against mechanical stresses like agitation and shearing. Examples of pharmaceutically acceptable surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esters are sold under the tradename Triton-X. When polysorbate 20 (Tween 20®) and polysorbate 80 (Tween 80®) are used they are generally used in a concentration range of about 0.001 to about 1%, of about 0.005 to about 0.2% and of about 0.01% to about 0.1% w/v (weight/volume).

As used herein, the term "stabilizer" can include a pharmaceutical acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., Crit. Rev. Ther. Drug Carrier Syst., 70(4):307-77 (1993); Wang, Int. J. Pharm., 7S5(2): 129-88 (1999); Wang, Int. J. Pharm., 203(1-2): 1-60 (2000); and Chi et al, Pharm. Res., 20(9): 1325-36 (2003). Stabilizers include but are not limited to sugars, amino acids, polyols, cyclodextrines, e.g. hydroxypropyl-beta-cyclodextrine, sulfobutylethyl-beta-cyclodextrin, beta-cyclodextrin, polyethylenglycols, e.g. PEG 3000, PEG 3350, PEG 4000, PEG 6000, albumine, human serum albumin (HSA), bovine serum albumin (BSA), salts, e.g. sodium chloride, magnesium chloride, calcium chloride, chelators, e.g. EDTA as hereafter defined. As mentioned hereinabove, stabilizers can be present in the formulation in an amount of about 10 to about 500 mM, an amount of about 10 to about 300 mM, or in an amount of about 100 mM to about 300 mM. In some embodiments, exemplary IL-12 can be dissolved in an appropriate pharmaceutical formulation wherein it is stable.

IL-12 also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

IL-12 to be used for in vivo administration must be sterile. This is readily accomplished by filtration through sterile filtration membranes, prior to or following lyophilization and reconstitution. IL-12 is stored in lyophilized form or in solution. Therapeutic IL-12 compositions generally are placed into a container having a sterile access port, for example, an intravenous solution bag or vial having a stopper pierceable by a hypodermic injection needle.

When applied topically, IL-12 is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, IL-12 formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arable; tragacanth gum; and karaya gum; and derivatives and mixtures thereof. The preferred gelling agent herein is one that is inert to biological systems, nontoxic, simple to prepare, and not too runny or viscous, and will not destabilize the IL-12 molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and IL-12 is present in an amount of about 300-1000 mg per ml of gel.

An effective amount of IL-12 to be employed therapeutically will depend, for example, upon the therapeutic objectives, the route of administration, and the condition of the patient. Accordingly, it is necessary for the therapist to titer the dosage and modify the route of administration as required to obtain the optimal therapeutic effect. Typically, the clinician will administer IL-12 until a dosage is reached that achieves the desired effect. A typical dosage for systemic treatment might range from about 10 ng/kg to up to 2000 ng/kg or more, depending on the factors mentioned above. In some embodiments, the dose ranges can be from about 1, 2, 3, 4, 5, 6, 7, 8, 9, 10, 11, 12, 13, 14, 15, 16, 17, 18, 19 to about 20; to about 30; to about 50; to about 100, to about 200, to about 300 or to about 500 ng/kg. In one aspect, the dose is less than 500 ng/kg. In another aspect, the dose is less than 300 ng/kg. In another aspect, the dose is less than about 200 ng/kg. In another aspect, the dose is less than about 100 ng/kg. In another aspect, the dose is less than about 50 ng/kg. In other aspects, the dose can range from about 10 to 300 ng/kg, 20 to 40 ng/kg, 25 to 35 ng/kg, 50 to 100 ng/kg.

In one aspect, exemplary therapeutic compositions described herein can be administered in fractionated doses. In one embodiment, the therapeutically effective dose is given before each fraction. In one embodiment, the therapeutically effective dose is given at about the same time as the administration of each chemotherapeutic dose or dose fraction. In one embodiment, the therapeutically effective dose is given before each fraction, ranging from 5, 10, 15, 20, 25, 30, 35, 40, 50, or 60 minutes before each fraction; or 2, 3, 4, 5, 6, 7, 8, 9, 10, 11, 12 hours after each fraction; or 1, 2, 3, 4, 5, 6, 7 days before each fraction. In one embodiment, the therapeutically effective dose is given after each fraction, ranging from 5, 10, 15, 20, 25, 30, 35, 40, 50, or 60 minutes after each fraction; or 2, 3, 4, 5, 6, 7, 8, 9, 10, 11, 12 hours after each fraction; or 1, 2, 3, 4, 5, 6, 7 days after each fraction; or once, twice, three times, 4 times, 5 times, 6 time, 7 times weekly, biweekly, or bimonthly, during or after the chemotherapeutic and/or combination chemotherapeutic/radiation treatment. In another embodiment, one or more exemplary doses of IL-12 is administered (1 to 100 ng/kg) at about 5, 10, 15, 20, 30, 40, 50, 60 min, 1, 2, 3, 4, 5, 6, 7, 8, 9, 10, 11, 12, 13, 14, 15, 16, 17, 18, 19, 20, 21, 22, 23, 24 hours, 1 day, 2 days, 3 days, 4 days, 5 days, 6 days, 7 days both before and after each chemotherapeutic dose.

As an alternative general proposition, the IL-12 receptor is formulated and delivered to the target site or tissue at a dosage capable of establishing in the tissue an IL-12 level greater than about 0.1 ng/cc up to a maximum dose that is efficacious but not unduly toxic. This intra-tissue concentration should be maintained if possible by the administration regime, including by continuous infusion, sustained release, topical application, or injection at empirically determined frequencies. The progress of this therapy is easily monitored by conventional assays.

"Near the time of administration of the treatment" refers to the administration of IL-12 at any reasonable time period either before and/or after the administration of the treatment, such as about one month, about three weeks, about two weeks, about one week, several days, about 120 hours, about 96 hours, about 72 hours, about 48 hours, about 24 hours, about 20 hours, several hours, about one hour or minutes. Near the time of administration of the treatment may also refer to either the simultaneous or near simultaneous administration of the treatment and IL-12, i.e., within minutes to one day.

III. Definitions

For the purpose of the current disclosure, the following definitions shall in their entireties be used to define technical terms and to define the scope of the composition of matter for which protection is sought in the claims.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

"Bone marrow preservation" means the process whereby bone marrow that has been damaged by radiation, chemotherapy, disease or toxins is maintained at its normal, or near normal, state; "bone marrow recovery" means the process whereby bone marrow that has been damaged by radiation, chemotherapy, disease or toxins is restored to its normal, near normal state, or where any measurable improvement in bone marrow function are obtained; bone marrow function is the process whereby appropriate levels of the various blood cell types or lineages are produced from the hematopoietic (blood) stem cells.

"Bone marrow failure" is the pathologic process where bone marrow that has been damaged by radiation, chemotherapy, disease or toxins is not able to be restored to normal and, therefore, fails to produce sufficient blood cells to maintain proper hematopoiesis in the mammal.

"Chemotherapy" refers to any therapy that includes natural or synthetic agents now known or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil for patients with locally advanced squamous cell carcinoma of the head (Tsukuda, M. et al., Int J Clin Oncol. 2004 June; 9 (3): 161-6), and fludarabine and bendamustine in refractory and relapsed indolent lymphoma (Konigsmann M, et al., Leuk Lymphoma. 2004; 45 (9): 1821-1827).

"Radiation therapy" refers to any therapy where any form of radiation is used to treat the disease state. The instruments that produce the radiation for the radiation therapy are either those instruments currently available or to be available in the future.

As used herein, radiation therapy "treatment modality" can include both ionizing and non-ionizing radiation sources. Exemplary ionizing radiation treatment modality can include, for example, external beam radiotherapy; Intensity modulated radiation therapy (IMRT); Image Guided Radiotherapy (IGRT); X Irradiation (e.g. photon beam therapy); electron beam (e.g. beta irradiation); proton irradiation; high linear energy transfer (LET) particles; stereotactic radiosurgery; gamma knife; linear accelerator mediated frameless stereotactic radiosurgery; robot arm controlled x irradiation delivery system; radioisotope radiotherapy for organ specific or cancer cell specific uptake; radioisotope bound to monoclonal antibody for tumor targeted radiotherapy (or radioimmunotherapy, RIT); brachytherapy (interstitial or intracavity) high dose rate radiation source implantation; permanent radioactive seed implantation for organ specific dose delivery.

"Ameliorate the deficiency" refers to a reduction in the hematopoietic deficiency, i.e., an improvement in the deficiency, or a restoration, partially or complete, of the normal state as defined by current medical practice. Thus, amelioration of the hematopoietic deficiency refers to an increase in, a stimulation, an enhancement or promotion of, hematopoiesis generally or specifically. Amelioration of the hematopoietic deficiency can be observed to be general, i.e., to increase two or more hematopoietic cell types or lineages, or specific, i.e., to increase one hematopoietic cell type or lineages.

"Bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, supporting cells (stromal cells), including but not limited to the associated stem and/or progenitor cells for these and other cell types and lineages.

"Hematopoietic cell type" generally refers to differentiated hematopoietic cells of various types, but can also include the hematopoietic progenitor cells from which the particular hematopoietic cell types originate from, such as various blast cells referring to all the cell types related to blood cell production, including stem cells, progenitor cells, and various lineage cells, such as myeloid cells, lymphoid cell, etc.

"Hematopoietic cell lineage" generally refers to a particular lineage of differentiated hematopoietic cells, such as myeloid or lymphoid, but could also refer to more differentiated lineages such as dendritic, erythroid, etc.

"IL-12 facilitated proliferation" of cells refers to an increase, a stimulation, or an enhancement of hematopoiesis that at least partially attributed to an expansion, or increase, in cells that generally reside or home to the bone marrow of a mammal, such as hematopoietic progenitor and/or stem cells, but includes other cells that comprise the microenvironment of the bone marrow niche.

"Stimulation or enhancement of hematopoiesis" generally refers to an increase in one or more hematopoietic cell types or lineages, and especially relates to a stimulation or enhancement of one or more hematopoietic cell types or lineages in cases where a mammal has a deficiency in one or more hematopoietic cell types or lineages.

"Hematopoietic long-term repopulating cells" are generally the most primitive blood cells in the bone marrow; they are the blood stem cells that are responsible for providing life-long production of the various blood cell types and lineages.

"Hematopoietic stem cells" are generally the blood stem cells; there are two types: "long-term repopulating" as defined above, and "short-term repopulating" which can produce "progenitor cells" for a short period (weeks, months or even sometimes years depending on the mammal).

"Hematopoietic progenitor cells" are generally the first cells to differentiate from (i.e., mature from) blood stem cells; they then differentiate (mature) into the various blood cell types and lineages.

"Hematopoietic support cells" are the non-blood cells of the bone marrow; these cells provide "support" for blood cell production. These cells are also referred to as bone marrow stromal cells.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating or controlling.

As used herein, the term "treating" refers to both therapeutic treatment and prophylactic or preventative measures, or administering an agent suspected of having therapeutic potential.

The term "a pharmaceutically effective amount" as used herein means an amount of active compound or pharmaceutical agent that elicits the biological or medicinal response in a tissue, system, animal or human that is being sought by a researcher, veterinarian, medical doctor or other clinician, which includes alleviation or palliation of the symptoms of the disease being treated.

As used herein, an "effective amount" in reference to the pharmaceutical compositions of the present disclosure refers to the amount sufficient to have utility and provide desired therapeutic endpoint.

In one embodiment, the therapeutic modality/regimen is accelerated fractionation therapy. In the accelerated fractionation therapy, the dose per fraction is unchanged while the daily dose is increased, and the total time for the treatment is reduced.

Combination (sequential or concurrent) therapy can be co-administration or co-formulation.

EXAMPLES

The invention is now described with reference to the following Examples. These Examples are provided for the purpose of illustration only, and the invention is not limited to these Examples, but rather encompasses all variations that are evident as a result of the teaching provided herein.

Example 1

FIG. 32 describes Murine IL-12 Promotes Hematopoietic Recovery in Irradiated Mice. Representative sections of femoral bone marrow from non-irradiated, untreated mice that were stained for IL-12Rβ2 (orange color) are shown in FIGS. 32A and 32B. Animals were subjected to TBI (8.0 Gy) and subsequently received vehicle (FIGS. 32B and 32C) or rMuIL-12 (20 ng/mouse) (FIGS. 32D and 32E) subcutaneously at the indicated times post irradiation. Femoral bone marrow was immunohistochemically stained for IL-12Rβ2 (orange color) 12 days after irradiation. While bone marrow from mice treated with vehicle lacked IL-12Rβ2-expressing cells and showed no signs of hematopoietic regeneration (FIG. 32C), mice treated with rMuIL-12 showed hematopoietic reconstitution and the presence of IL-12Rβ2-expressing megakaryocytes, myeloid progenitors, and osteoblasts (FIGS. 32E and 32F).

Example 2

Summary and Design of an exemplary First-in-Human (FIH) Clinical Study

The study, entitled *A Phase* 1, *Double Blind, Placebo-Controlled, Single Ascending Dose Study of the Safety, Tolerability, Pharmacokinetics, and Pharmacodynamics of HemaMax*™ (*rHuIL*-12) *in Healthy Adult Volunteers* (IND 104,091), is designed to determine the safety and tolerability with secondary objectives to evaluate the pharmacokinetics and immunogenicity of single ascending subcutaneous (SC) dose of HemaMax™ in healthy adult subjects.

Up to 30 healthy male and female adult subjects aged 18-45 years are enrolled in 4 consecutive cohorts of 6 subjects each, and sentinel subjects are used at each dose level. A single SC injection of investigational product (either HemaMax™ or placebo) is administered in the abdomen at dose levels of 2, 5, 10, and 20 μg. Cohorts of 6 subjects is evaluated per dose level (n=2 for placebo and n=4 for HemaMax™) in double-blind fashion. An additional expansion cohort of n=6 subjects (2 placebo and 4 HemaMax™) may be enrolled to receive the highest dose (or placebo) administered in the ascending dose portion of the study.

Example 3: NM-IL-12

The pharmacist prepares the HemaMax™ dosing solution in the form of a filled syringe for injection into the subject. In this trial, the Investigational Product (IP) consists of the HemaMax (rHuIL-12) Drug Product in 2 mL clear vials. The HemaMax (rHuIL-12) Drug Product vial contains 0.65 mL of 20 μg/mL rHuIL-12 protein in 10 mM sodium phosphate, 150 mM sodium chloride, pH 6.0 with 0.1% (w/v) Poloxamer 188 (withdrawal volume of 0.50 mL). These solutions are clear and colorless.

Remove vials from refrigerator and allow to sit at room temperature for at least 15 minutes prior to preparation of doses. A BD syringe with polypropylene barrel with detached 25 G ⅝ needle or BD Tuberculin Syringe (catalog #305553, 27 g ½ needle attached) has been shown to be compatible. The syringe with the prepared solution can be kept at room temperature for 6 hours. If a longer storage time is desired the syringe can be stored at 2-8° C. for 24 hours. If a syringe with separate needle is used, overfill the dose syringe by approximately 0.1 mL, then remove the needle and replace with new needle, and gently expel until the appropriate dose is reached.

Example 4

IL-12 is not constitutively produced in the body, as demonstrated by this example. 110 subjects were tested and none were found to have levels of IL-12 above the Lower Limit of Quantification (LLOQ).

Figure 35:
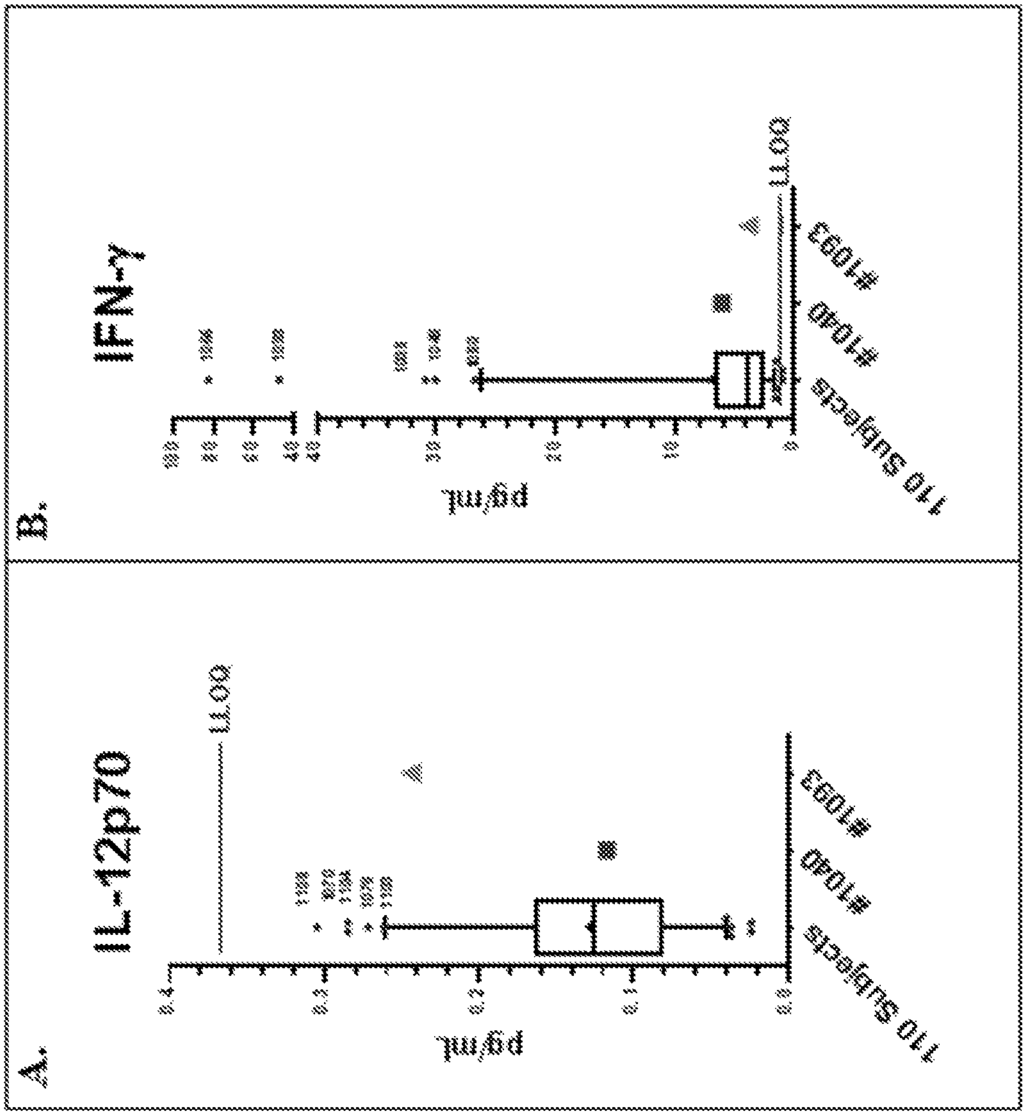
FIG. 35: Shows IL-12 and IFN-gamma Baseline Levels. A box-and-whiskers plot presented in FIGS. 35A and 35B describe IL-12 (35A) and IFN-gamma (35B) baseline levels of 110 subjects with whiskers covering 5-95 percentile of the baseline values. IL-12 baseline levels were defined using the kit standard curve.

IL-12 and IFN-gamma Baseline Levels: A box-and-whiskers plot presented in FIGS. 35A and 35B describe IL-12 and IFN-gamma baseline levels of 110 subjects with whiskers covering 5-95 percentile of the baseline values. IL-12 baseline levels were defined using the kit standard curve. As shown in FIG. 35A, all pre-dose IL-12 levels for 110 subject were Below the Limit of Quantitation (BLQ) (LLOQ=0.367 pg/ml). Almost all IFN-gamma levels were quantifiable above the LLOQ (LLOQ=1.08 pg/ml), most in low pg/ml range. Five high end outliers showed baseline levels of IFN-gamma>23 pg/ml, including subject 1033 and 1055.

While this invention has been disclosed with reference to specific embodiments, it is apparent that other embodiments and variations of this invention can be devised by those skilled in the art without departing from the true spirit and scope of the invention. The appended claims include all such embodiments and equivalent variations.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of treating a subject suffering from a disease selected from chronic kidney disease (CKD) or age-related macular degeneration (AMD), the method comprising: (a) identifying a subject having an endogenous IL-12 concentration in peripheral blood suppressed to level of less than 5 pg/ml±10%, and (b) administering exogenous IL-12 to the identified subject, wherein administering the exogenous IL-12 results in an increase of IL-12 in the peripheral blood of the identified subject, as measured by a standard ELISA for IL-12 p70.

2. The method of claim 1, wherein the identified subject has the endogenous IL-12 concentration of less than 3 pg/ml±10% or less than 1 pg/ml±10%.

3. The method of claim 1, wherein:

the identified subject also shows an increase in IFN-gamma concentration in peripheral blood.

4. The method of claim 1, wherein the exogenous IL-12 is administered at a dose from 1 μg±10%, to less than 20 μg±10%.

5. The method of claim 1, wherein the exogenous IL-12 is administered at a dose from 8 μg±10% to about 15 μg±10%.

6. The method of claim 1, wherein the exogenous IL-12 is administered at a dose from 10 μg±10% to 12 μg±10%.

7. The method of claim 1, wherein the identified subject is administered one or more treatment doses of exogenous IL-12 and one or more maintenance doses of exogenous IL-12.

8. The method of claim 7, wherein:

the treatment dose of exogenous IL-12 is from 1 μg±10% to 20 μg±10% and the maintenance dose of exogenous IL-12 is from 1 μg±10% to 10 μg±10%.

9. The method of claim 7, wherein:

the treatment doses of exogenous IL-12 are administered every 2 weeks, every 3 weeks, or every 4 weeks; and/or the maintenance doses of exogenous IL-12 are administered every 1 month, every 2 months, or every 3 months.

10. The method of claim 1, wherein:

the exogenous IL-12 is administered topically, subcutaneously, intravenously, intraperitoneally, intramuscularly, epidurally, or parenterally.

11. The method of claim 1, wherein the exogenous IL-12 is a rHuIL-12.

12. The method of claim 1, wherein: (a) the suppression of endogenous IL-12 expression results in suppression of immune cells in the identified subject; and/or (b) administering exogenous IL-12 restores endogenous IL-12 pleiotropic immune and hematopoietic effects in the identified subject.

13. The method of claim 1, where the identified subject has chronic kidney disease (CKD) and administering exogenous IL-12 results in repair and regeneration of the kidney, thereby slowing progression of CKD.

14. The method of claim 13, wherein: (a) the progression of CKD is slowed; and/or (b) slowing of progression of CKD is demonstrated in the identified subject by one or more of a decrease of creatinine, decrease of blood urea nitrogen (BUN), decrease in albuminuria, or an increase in glomerular filtration rate (GFR), and/or (c) exogenous IL-12 is administered in combination with a conventional treatment for CKD.

15. The method of claim 1, wherein the identified subject has age-related macular degeneration (AMD) and administering exogenous IL-12 results in slowing or reversing AMD progression.

16. The method of claim 15, wherein: (a) progression of AMD is slowed or reversed by IL-12's effects of (i) reducing neovascularization, and/or (ii) restoring immune balance by replenishment of senescent macrophages; and/or (b) administering exogenous IL-12 results in slowing or reversing AMD progression, as compared to that observed in the absence of administration of exogenous IL-12; and/or (c) exogenous IL-12 is administered in combination with a conventional treatment for AMD.

17. The method of claim 15, wherein: exogenous IL-12 is administered via subcutaneous injection or via intraocular injection.

* * * * *